(12) United States Patent
Filho et al.

(10) Patent No.: US 8,404,283 B2
(45) Date of Patent: Mar. 26, 2013

(54) STANDARDIZED PLANT EXTRACT, PROCESS FOR OBTAINING THE SAME AND USES THEREOF

(75) Inventors: Valdir Cechinel Filho, Itajai (BR); Tania Mari Belle Bresolim, Itajai (BR); Christiane Meire da Silva Bittencourt, Itajai (BR); Marcia Maria De Souza, Itajai (BR); Ruth Meri Lucinda, Itajai (BR); Nara Lins Meira Quintao, Itajai (BR); Ticiana Camila Mora, Itajai (BR); Carlos Picolli, Itajai (BR); Marcello Creado Pedreira, Sao Paulo (BR); Marcelo Eidi Nita, Sao Paulo (BR); Rodrigo Spricigo, Sao Paulo (BR)

(73) Assignees: Eurofarma Laboratorios Ltda, Sao Paulo-SP (BR); Fundaca O Universidade do Vale Do Itajai, Itajai SC (BR)

(*) Notice: Subject to any disclaimer, the term of this patent is extended or adjusted under 35 U.S.C. 154(b) by 6 days.

(21) Appl. No.: 12/739,921

(22) PCT Filed: Oct. 24, 2008

(86) PCT No.: PCT/BR2008/000319
§ 371 (c)(1),
(2), (4) Date: Aug. 20, 2010

(87) PCT Pub. No.: WO2009/052600
PCT Pub. Date: Apr. 30, 2009

(65) Prior Publication Data
US 2010/0303907 A1    Dec. 2, 2010

(30) Foreign Application Priority Data

Oct. 26, 2007    (BR) .................................... 0703947

(51) Int. Cl.
*A61K 36/00* (2006.01)
(52) U.S. Cl. ....................................................... 424/725
(58) Field of Classification Search ........................ None
See application file for complete search history.

(56) References Cited

PUBLICATIONS

Meyre-Silva et al. "Isolation of a C-Glycoside Flavonoid with Antinociceptive Action from *Aleurites moluccana* Leaves". Planta Med 65 (1999) 293-294.*
R. Agarwal et al., "Oil Rich Euphorbiaceae Seeds With High Contents of Linoleic Acid", Fat Sci Technol., Dec. 1995, p. 526-527.
C.P. Locher et al., "Anti-Microbial Activity and Anti-Complement Activity of Extracts Obtained From Selected Hawaiian Medicinal Plants", Journal of Ethno-Pharmacology 49, 1995, p. 23-32, vol. 49, Elsevier Science Ireland Ltd.
Luis M. Blanco-Colio et al., "Atorvastatin Decreased Elevated Soluble Cd40I in Subjects at High Cardiovascular Risk. Atorvastatin on Inflammatory Markers Study: A Substudy of Actfast", p. 560-563, vol. 74, 2008 International Society of Nephrology.
Frank E. Koehn et al., "The Evolving Role of Natural Products in Drug Discovery", Nature Reviews Drug Discovery, Mar. 2005, p. 206-220, vol. 4.
W.H. Hur et al., "An Examination of the Euphorbiaceae of Hong Kong", Aust. J. Chem, 1968, p. 1675-7, vol. 21.
Sara Gnecco et al., "Distribucion DE n-Alcanos En Especies Chilenas Pertenecientes A La Familia Euphorbiaceae", Bol. Soc. Chil. Quim., 1996, p. 229-233, vol. 41, No. 3.
B.I. Fozdar et al., "Aleuritin, A Coumarinolignoid, and a Coumarin From *Aleurites fordii*", Phytochemistry, 1989, p. 2459-2461, vol. 28, No. 9, Maxwell Pergamon Macmillam plc.
W. Stuppy et al., "Revision of the Genera Aleurites, Reutealis and Vernicia (Euphorbiaceae)", Blumea 44, 1999, p. 73, vol. 44.
Bradley E. Hope BA, et al., "Hawaiian material medica for asthma", Hawaii Medical Journal, Jun. 1993, p. 160, 162, 164-166, vol. 52, No. 6.
Diva Songaglio et al., "Desenvolvimento Technologico E Producao De Fitoterapicos", p. 221-258.
A. Sutaeg Hwang et al., Analgesic Properties of Intrathecally Administered Heterocyclic Antidepressants, Pain, 1987, p. 343-355, vol. 28, Elsevier Science Publishers B.V.
Tânia S.F . Saleh et al., "Pro-inflammatory Effects Induced by Bradykinin in a Murine Model of Pleurisy", European Journal of Pharmacology, 1997, p. 43-52, vol. 331, Elsevier Sciences B.V.
Mara Sueli Aparecida et al., "Universidade do Vale do Paraiba Instituto de Pesquisa e Desenvolvimento" 2002, São Jose dos Campos, SP.
J. Roth et al., "Fever Induction Pathways: Evidence from Responses to Systemic or Local Cytokine Formation", Brazilian Journal of Medical and Biological Research, 2001, p. 301-314, vol. 34, No. 3.
Rafael O.P. De Campos et al., "Antioedematogenic and Antinociceptive Action of NPC 18521, A Novel Bradykinin $B_2$ Receptor Antagonist", European Journal of Pharmacology, 1996, p. 227-286, vol. 316, Elsevier Science B.V.
Nara L.M. Quintão, et al., "The Effects of Diacerhein on Mechanical Allodynia in Inflammatory and Neuropathic Models of Nociception in Mice", Anesth Analg, 2005, p. 1763-9, vol. 101, International Anesthesia Research Society.
Nara L.M. Quintao., et al., "Long-Lasting Neuropathic Pain Induced by Brachial Plexus Injury in Mice: Role Triggered by the Pro-Inflammatory Cyctokine, Tumour Necrosis Factor x", Neuropharmacology, 2006, 9.614-620, vol. 50, Elsevier Ltd.

(Continued)

*Primary Examiner* — Amy L Clark
(74) *Attorney, Agent, or Firm* — Arent Fox LLP

(57) ABSTRACT

The present invention refers to a process for obtaining a standardized extract having antinociceptive, anti-inflammatory and antipyretic properties, from at least one part of a plant of genus *Aleurites*. Furthermore, the present invention provides a pharmaceutical composition comprising an active ingredient of a pharmaceutically efficient quantity of standardized extract from at least one part of the plant of genus *Aleurites*. Finally, the present invention describes a method of treatment and use of the said extract, isolated or in a pharmaceutical composition, for the prevention, control or treatment of painful, inflammatory or febrile affections.

13 Claims, 26 Drawing Sheets

PUBLICATIONS

Cal Kassuya et al., "Intraplantar $PGE_2$ Causes Nociceptive Behaviour and Mechanical Allodynia: The Role of Prostanoid E Receptors and Protein Kinases", British Journal of Pharmacology, 2007, p. 727-737, vol. 150.

Yu Qing Cao et al., "Primary Afferent Tachykinins are Required to Experience Moderate to Intense Pain", Nature, 1998, p. 390-394, vol. 392.

Juliano Ferreira, et al., "Evidence for the Participation of Kinins in Freund's Adjuvantinduced Inflammatory and Nociceptive Responses in Kinin $B_1$ and $B_2$ Receptor Knockout Mice", Neuropharmacology, 2001, p. 1006-1012, vol. 41, Elsevier Science Ltd.

Léslei B Bortalanza et al., "Anti-Allodynic Action of the Tormentic Acid, A Triterpene isolated from Plant. Against Neuropathic and Inflammatory Persistent Pain in Mice", European Journal of Pharmacology, 2002, p. 203-208, vol. 453, Elsevier Science B.V.

Paul I. Forster, "A Taxonomic Revision of Aleurites J.R. Forst & G. Frost. (Euphorbiaceae) in Australia and New Guinea", Muelleria, 1996, p. 5-13, vol. 9.

Brito, A.S., "Ensaios Toxicologicos in vivo", Unicamp, 1994, p. 41-121, vol. 199.

H.O.J. Collier, et al., "The Abdominal Constriciton response and Its Suppression by Analgesic Drugs in the Mouse", Br. J. Pharmac. Chemother., 1968, p. 295-310, vol. 32.

David Dubuisson et al., "The Formalin Test: A Quantitative Study of the Analgesic Effects of Morphine, Meperidine, and Brain Stem Stimulation in Rats and Cats", Pain, 1977, p. 161-174, vol. 4.

Ameenah Gurib-Fakim, "Medicinal Plants: Traditions of Yesterday and Drugs of Tomorrow", Molecular Aspects of Medicine, 2006, 9.1-93, vol. 27, 2005 Elsevier Ltd.

Farmacopeia Brasileira 5 edicao, vol. 1, Brasilia 2010, 2010 Agencia Nacional de Vigilancia Sanitaria.

V.2.17.6 Material Para Cromatografia. 1988, F.Bras. IV.

Bart C.J. M. Fauser, MD., et al., "Consensus on Woman's Health Aspects of Polycystic Ovary Syndrome (PCOS): The Amsterdam ESHRE/ASRM-Sponsored $3^{rd}$ PCOS Consensus Workshop Group", Fertility and Sterility, Jan. 2012, vol. 97 No. 1.

Leonardo Gobbo-Neto et al., "Plantas Medicinais: Factores De Influencia No Conteudo De Metabolitos Secundarios", Quim. Nova, 2007, p. 374-381, vol. 30, No. 2.

Christopher P. Locher et al., "Antiviral Activity of Hawaiian Medical Plants Against Human Immunodeficiency Virus Type-1 (HIV-1)", Phytomedicine, 1996, p. 259-264, vol. 2 (3), Gustav Fischer Verlag, Stuttgart•Jena•New York.

Christiane Meyre-Silva, et al., "Isolation of a C-Glycoside Flavonoid with Antinoceptive Action from Aleurites moluccana Leaves", Planta Med., 1999, p. 293-294, vol. 65.

D.R. Misra et al., "Terpenoids and Related Compounds—XI[1] Chemical Investigations of Aleurites montana and the Structure of Aleuritolic Acid—A New Triterpene Acid", Jan. 17, 1970, p. 3017-3021, vol. 26, Pergamon Press 1970.

M.J. Pascual Villalobos et al., "La familia Euphorbiaceae como fuente de aceites vegetales para la industria technoquimica", 1992, p. 39-49, vol. 43 Fasc. 1.

M. Pio Correa, "Dicionario Das Plantas Uteis Do Brasil E Das Exoticas Cultivadas", 1984, p. 294, vol. V.

Diario Oficial da Uniao—Secao 1, 2 de junho de 2003, p. 56-59, No. 104, segunda-feira.

Souze MM et al., "Metodos De Avaliacao De Atividade Biologica De Pro", Ciencias Farmaceuticas : Contribuicao Ao Desenvolvi, 2003, p. 108-166, Univali Editora Itajai, Santa Catarina.

\* cited by examiner

STANDARDIZED PLANT EXTRACT, PROCESS FOR OBTAINING THE SAME AND USES THEREOF

CROSS-REFERENCE TO RELATED APPLICATION

This application is a National Stage entry of International Application No. PCT/BR2008/000319, filed Oct. 24, 2008, which claims priority to Brazilian Application Number PI0703947-6, filed Oct. 26, 2007, the disclosure of the prior applications is hereby incorporated in their entirety by reference.

FIELD OF THE INVENTION

The present invention refers to a process for obtaining a standardized extract having antinociceptive, anti-inflammatory and antipyretic properties, from a plant of genus *Aleurites*. The invention further provides a pharmaceutical composition comprising the said standardzed extract, methods of treatment, prevention or control of painful, inflammatory or febrile affections and uses of the said extract.

BACKGROUND OF THE INVENTION

Pain is the most common symptomatic manifestation in humans. It is a complex condition, often of undefined aetiology. While acute pain is often the result of traumatism, visceral dyskinesia, acute inflammatory processes and infections, chronic pains are normally related to musculoskeletal, neuropathic and oncolytic affections and chronic inflammatory processes.

Several mechanisms are related to the occurrence of acute pains: traumatism of the musculoskeletal structures and soft tissues, dysfunctional anomalies, acute inflammatory processes, abdominal, thoracic or oropharyngeal visceral infections and dyskinesias may all trigger physical, mechanical, thermal and/or chemical stimuli that activate the nociceptors in the fibres of the peripheral nervous system. These transmit nociceptive information to the spinal medulla and subsequently to the hypothalamus and cortical areas involved in the processing of sensibility and originating in pain.

The more common chronic manifestations of pain are linked to chronic inflammatory processes normally seen in osteoarthritis, tendonitis, bursitis, spondylitis and other generally autoimmune degenerative processes. More than the actual pain, this process focuses the phenomenon of mechanical and thermal hyperalgesia related to decreased nociceptor thresholds which produce hypersensitivity to movement, mechanical deformation and heat. Hyperalgesia is caused by the action of numerous inflammatory mediators released in the painful regions, and more specifically bradykinin, acetylcholine, histamine and the cytokines, such as interleukins and tumour necrosis factors. The resulting hypersensitivity justifies the fact that inflamed tissues are pain free when at rest but become painful when stimulated.

The treatment and adequate control of pain and frequent inflammation is by pharmacotherapy, whereby several pharmacologic classes known in the state of the art are used for analgesic and anti-inflammatory purposes, with a large majority of these being obtained by means of chemical synthesis.

The most currently used analgesic and anti-inflammatory drugs are from the class of non-steroidal anti-inflammatory drugs (NSAID), such as salyclates, acetic acid derivatives, indolic derivatives and enol acid derivatives, amongst others.

However, the main problem related to the use of the anti-inflammatories specified above is due to their collateral effects, especially during prolonged administration. These effects include gastritis, ulceration, dyspepsia, nausea, vomiting, allergies, renal insufficiency, irreversible nephropathy, Reye's Syndrome, metabolic acidosis, hypertension and a risk of cardiovascular diseases.

In the case of non-selective NSAIDs, the non-specific inhibitors of the cyclooxygenase (COX) enzyme inhibit both COX-1, considered constitutive and responsible for the homeostasis of organs such as the stomach and kidneys, as well as COX-2, considered inductive and increasing in the organism at the genesis of the inflammatory process. COX-2 is responsible for the production of pro-inflammatory prostanoid mediators such as certain prostaglandin and leukotrienes. The inhibition of this enzyme (COX-2) is important for the reduction of the inflammatory process. However, the inhibition of COX-1 triggers the adverse effects described above and, more specifically, the gastrointestinal disorders because it is an important regulator of hydrochloric acid production as well as the production of the bicarbonate and mucous coating protecting the stomach from the acids and enzymes in the gastric juice.

The use of NSAIDs has been associated with serious complications. Such problems either impede adhering to the pharmacologic treatment per se, or render the treatment of chronic painful and/or inflammatory processes impossible.

In view of these limitations, it is understandable that the development of safer therapies or, in other words, with a better risk-benefit ratio, for the treatment of pain and inflammation is necessary, especially considering the risks associated to the pharmaceuticals currently in use.

In this context, phytotherapy presents itself as an appropriate alternative to the predominantly synthetic therapeutic arsenal.

The importance and chemical potentiality of medicinal plants can be ascertained from scientific research data results whereby approximately 50% of the medicines used clinically worldwide originate from natural products and derivatives (Gurib-Fakim, A., 2006, *Mol. aspects med.,* 27, 1-93).

Frequently, the pharmacologic effects of phytotherapeutic medicines does not occur through the action of a single compound but rather through the combined activity of the various active substances contained or associated to it. Generally, the active substance isolated presents a different activity or lesser potency than that presented by the phytocomplex.

Contrary to medicines of synthetic origin, the active substances of phytotherapeutic medicines are almost always found in low concentrations which, generally, result in a lower incidence of adverse effects.

Despite the limitations encountered when obtaining, purifying and identifying natural products, recent technological advances have enabled obtaining more powerful and enhanced products when compared to synthetic products. (Koehn, F. E. & Carter, G. T., 2005, *Nature,* 4, 206-220).

A common issue to the use and production of phytomedicines relate to the variations in the concentration(s) of the active ingredient(s) which are generally secondary metabolites. These metabolites represent an interface between the plants and their environment and their synthesis is frequently affected by ambient conditions (such as seasonality, circadian rhythm, plant development stage, plant age, temperature, availability of water, ultraviolet (UV) radiation, soil nutrients, altitude, atmospheric composition and plant tissue damage). Such factors, as well as others such as gathering conditions, stabilisation, storage and industrial processing may all have an effect on the content of the secondary metabolites of medicinal plants and thus may also have a major influence on the quality of the phytotherapeutics being prepared. Therefore, apart from quality control involving modern analytic techniques and the standardisation of the intermediary products, the source and quality of the raw materials have a preponderant role for obtaining products of constantly reliable composition and reproducible therapeutic properties (Gobbo-Neto, L. & Lopes, N. P., 2007, *Quím. Nova*, 30, 374-381).

The Euphorbiaceae family originated from tropical Asia and the Pacific islands that consist of herbaceous plants, shrubs or trees generally producing ligneous latex. In Brazil, they are found in tropical areas being widely cultivated in coastal regions but may also be found in temperate regions. This family includes approximately 7.000 species with 317 genus (Webster, G. L., 1994, *Annals of the Missouri. Botan. Garden*, 81, 1, 3-32). Former studies of this family revealed a predominant presence of lipids, terpenoids, alkaloids and hydrocarbons (Hui, W. H. & Hoi, C. T., 1968, *Aust. J. Chem.*, 21, 1675-7). Other studies also showed the importance of this family as food and in medicines as well as in industry (Gneco, S. et al., 1996, *Bol. Soc. Chil. Quim.*, 41, 229-233; Villalobos, M. J. P. & astellanos, E. C., 1992, *Grasas Y aceites*, 43, 1, 39-44).

Among the several genus of the Euphorbiaceae family, the following should be mentioned being of the most importance due to their diversity, applications and commercial interest: *Euphorbia, Croton, Phyllanthus, Jatropha, Sapium, Ricinus, Aleurites* (Webster, G. L., 1994, *Annals of the Missouri. Botan. Garden*, 81, 1, 3-32). The genus *Aleurites* is subdivided in *A. trisperma, A. cordata, A. montana, A. fordii, A. montance, A. rockinghamensis*, apart form *A. moluccana* (Villalobos, M. J. P. & Castellanos, E. C., 1992, *Grasas y aceites*, 43, 1, 39-44; Misra, D. R. e Khastgir, H. N., 1970, *Tetrahedron*, 26, 12, 3017-3021; Cruz, G. L. *Dicionário das plantas úteis do Brasil*. 4th ed. Rio de Janeiro: Bertrand, 1964; Pio Correia, M. *Dicionário das plantas úteis do Brasil e das exóticas cultivadas*. IBDF, Brasília—DF (1984)V:294-295; Fozdar, B. I. et al., 1989, *Phytochem.*, 28, 9, 2459-2461; Agarwal, R. et al., 1995, *Fett. Wissench. Technologie-Fat Science Technol.*, 97, 526-527; Forster, P. I., 1996, *Muelleria*, 9, 5-13).

The *Aleurites moluccana* L. Willd., having the synonyms *Aleurites triloba* J. R. & G. Forst, *Croton moluccanus* L., *Jatropha moluccana* is an exotic tree native of Indonesia having been broadly introduced to Brazil and spreading from the state of Sao Paulo through to the state of Rio Grande do Sul, being especially abundant in the state of Santa Catarina. It is popularly known locally as "Nogueira-de-Iguape", "Noz-da-Índia", "Nogueira-da-Índia" "Nogueira-de-Bancul", or simply "Nogueira" (Duke, J. A., *Handbook of medicinal herbs*. U.S.A.: CRC Press, 1991).

The use of *Aleurites moluccana* in traditional popular remedies is vast as is the case of most medicinal plants. It is used to control and as an empirical treatment for the following diseases or symptoms: fever, inflammations, asthma, conjunctivitis, hepatitis, headaches, ulcerations, diarrhoea, gonorrhoea and is also used against tumours, as a laxative stimulant, diaphoretic and anti-rheumatic. (Pio Correia, M. *Dicionário das plantas úteis do Brasil e das exóticas cultivadas*. IBDF, Brasília—DF, 1984, 294-295; Villalobos, M. J. P. & Castellanos, E. C., 1992, *Grasas Y aceites*, 43, 1, 39-44; Forster, P. I., 1996, *Muelleria*, 9, 5-13; Duke, James A. *Handbook of medicinal herbs*. *U.S.A.*: CRC Press, 1991; Stuppy, W. et al., 1999, *Blumea*, 44, 1, 73-98; Locher, C. P. et al., 1995, *J. Ethnopharmacol.*, 49, 23; Hope, B. E. et al., 1993, *Hawaii Med.*, 56, 6, 160-166). Nevertheless, very few studies able to systematically justify this broad therapeutic potential are described in the literature.

Certain prior studies by a Belgian research group demonstrated that the extracts of a plant collected in Hawaii showed antiviral activity, more specifically against the HIV virus (Locher, C. P. et al., 1996, *Phytomedicine*, 2, 259), as well as an antibacterial effect against *Staphylococus aureus* and *Pseudomonas aeruginosa* (Locher, C. P. et al., 1995, *J. Ethnopharmacol.*, 49, 23).

Other preliminary studies conducted by the present inventors and their collaborators further demonstrated that non-standard hydroalcoholic extracts of *Aleurites moluccana* as well as their hexanic fractions, presented analgesic potential in an acetic acid-induced pain model in mice. Furthermore, analysis of the active ingredients isolated led to the identification of n-hentriacontane, alpha-amyrin, beta-amyrin, alpha-amirinone, beta-amirinone, stigmasterol, beta-sitosterol, campesterol, acetil aleuritolic acid (AAA), swertisin and 2"-O-rhamnosylswertisin, with some of these substances having significantly inhibited the acetic acid induced abdominal contortions in mice (Meyre-Silva, C. et al., 1998, *Phytomedic.*, 5, 2, 109-113; Meyre-Silva, C. et al., 1999, *Planta Med.*, 65, 3, 293-294).

In 1999, the inventors and their collaborators also demonstrated that swertisin, a flavonoid isolated from the leaves of *Aleurites moluccana*, did not have an analgesic effect with the acetic acid induced abdominal contortion model in mice. However, its derivate 2"-O-rhamnosylswertisin presented analgesia approximately 16 times more powerful than aspirin with this model, thus suggesting that the ramnosil group has an important role in the analgesic action of these compounds (Meyre-Silva, C. et al., 1999, *Planta Med.*, 65, 3, 293-294).

Thus, former studies conducted by the inventors and their collaborators successfully identified potential use for the species in the development of new phytotherapeutic medicines.

The studies and research hereby presented by the inventors demonstrate new antinociceptive, anti-inflammatory and antipyretic activities related to the extracts of *A. moluccana* which are confirmed in the data and tests described below in the present report.

The inventors further identified a set of remarkable procedures, practices and conditions when compared to the current state of the art, as described below, that contribute to the use of *Aleurites moluccana* as a medicine/pharmaceutical input by guaranteeing that the specifications, safety and efficacy of its analgesic and anti-inflammatory properties remain reproducible and consistent.

In the light of the above, a process for obtaining a standardized extract from *Aleurites moluccana*, a process for isolating its marker and a process for preparing a phytotherapeutic pharmaceutical composition having analgesic, anti-inflammatory and antipyretic properties as well as a treatment method and its use as an alternative therapy to NSAIDs in view of its therapeutic potential and, possibly, better safety and tolerability characteristics are all obviously particularly interesting.

SUMMARY OF THE INVENTION

The present invention refers to a process for obtaining a standardized extract having antinociceptive, anti-inflammatory and antipyretic properties, from a plant of genus *Aleurites*, preferentially, *Aleurites moluccana* L. Willd, using, at least, one part of the plant, preferentially the leaves, with the said standardized extract being distinguished by the marker 2"-O-rhamnosylswertisin. The invention further provides a pharmaceutical composition comprising the said standardized extract, methods of treatment for prevention or control of painful, inflammatory or febrile affections and uses of the said extract.

The invention also refers to the pharmacological characterisation of the above mentioned standardized extracts, with reference to their antinociceptive, anti-inflammatory, antipyretic, antiedematogenic, anti-hypernociceptive activities and their acute toxicity evaluation.

The invention further provides a pharmaceutical composition comprising an active ingredient of as therapeutically efficient amount of a standardized extract of *Aleurites moluccana* containing at least one active ingredient selected from the group comprising of alpha-amyrin, beta-amyrin, alpha-amirinone, beta-amirinone or swertisin, with the said extract being standardized in relation to its marker 2"-O-rhamnosylswertisin. Preferentially, the pharmaceutical composition of the invention comprising the standardized extract of *Aleurites moluccana* contains a 2"-O-rhamnosylswertisin rate in the range between 0.05 to 15%.

Finally, as an additional embodiment, the present invention comprises a treatment method and use of said extract, isolated or within a pharmaceutical composition, to prevent, control ou treat conditions of pain, inflammation and/or fever.

BRIEF DESCRIPTION OF THE DRAWINGS

The following figures are part of the present report and are included here so as to illustrate determined aspects of the invention. The object of the present invention may be better understood referring to one or more of these figures, combined with the detailed description of the preferred mode presented herein.

DETAILED DESCRIPTION OF THE INVENTION

Figure 1B:
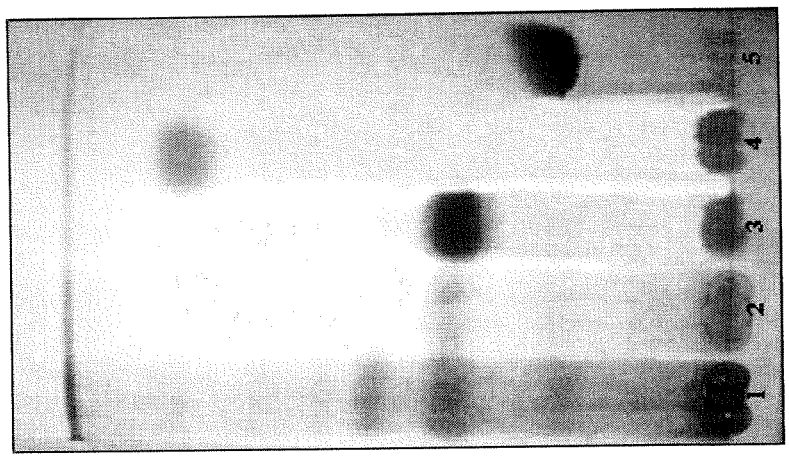
FIG. 1 shows a chromatography profile of the results obtained from the soft extract and dry extract of *Aleurites moluccana*, using a mixture of AcOEt:Acetone:$H_2O$ 25:8:2 as an eluant in (A) and using a mixture of hexane:AcOEt 85:15 as an eluant in (B).

To facilitate full comprehension of the present invention, it shall be explained in greater detail below by identifying its particularities and preferred modes. However, the present description shall not be taken as limiting the embodiments of the invention.

Processes for Obtaining Standardized Extracts

A process for obtaining a standardized extract is particularly useful to the development of a phytomedicine by guaranteeing its quality, its phytochemical constitution by the use of markers, its physicochemical characteristics, its pharmacological properties and, consequently, its therapeutic action in a reproducible manner.

Overall, the process for obtaining a standardized extract, from at least one part of a plant of the genus *Aleurites*, having antinociceptive, anti-inflammatory and antipyretic properties, in accordance with the present invention, comprises the following stages:
  collection, drying and subdivision of the plant material;
  pre-extraction; exraction with an extractor solvent;
  filtration of the extract;
  concentration of the extract
  pasteurisation;
  drying; and
  qualitative and quantitative analysis (standardisation) of the extract.

The stages of the process, in accordance with the present invention, are sufficient to ensure an adequate concentration of, at least, one of the following compounds: alpha-amyrin, beta-amyrin, alpha-amirinon, beta-amirinon, swertisin and 2"-O-rhamnosylswertisin. More specifically, the stages of the process are capable of providing the standardized extract with a total concentration of flavonoids attaining between 0.1 to 15% of its constitution. More preferentially, the stages of the process are capable to provide a standardized extract with a total concentration of 2"-O-rhamnosylswertisin attaining between 0.05 to 15% of its constitution.

In accordance with the present invention, the collection, drying and subdivision stage is performed with the plant material obtained from a part of a plant from the genus *Aleurites* which include: *A. trisperma, A. cordata, A. montana, A. fordii, A. montance, A. rockinghamensis* and *A. moluccana*. Preferentially, the plant material used is from a part of the species *Aleurites moluccana* L. Willd, and more specifically, from its leaves.

The plant material can be obtained advantageously from healthy individuals of the species *A. moluccana*, whether adult ($\geq$10 years), young (<10 years), intact or in shoot stage, and may be collected in any month of the year, any season and any hour or period of the day. However, the collection of the plant material is especially useful when undertaken in winter due to the better phytochemical profile of the species in this period.

In accordance with the present invention, the plant material may be used fresh, dried, whole, torn, chopped, shredded, ground, powdered or micronised. More specifically, the use of the plant material dried and shredded in particles with a size of 50 mm or less.

The process for obtaining the standard extract in accordance with the present invention requires a pre-extraction stage corresponding to washing the plant material with an adequate solvent, preferentially ethanol. The pre-extraction stage is especially advantageous for eliminating the contaminants or impurities adsorbed by the plant material, particularly heavy metals (eg. lead and mercury) adsorbed by the leaf, which may contaminate the final standard extract unless they are eliminated. In a preferred embodiment of the pre-extraction stage, the plant material is washed with a sufficient quantity of ethanol 96° GL, under constant agitation, at room temperature, for 15 to 30 minutes, with the solvent being drained and eliminated after this period.

The extraction stage of the process using extractor solvent in accordance with the present invention comprises an extraction procedure such as, but not limited to, maceration, percolation, decoction, infusion, lixiviation, distillation, turbo extraction, supercritical extraction or similar, using an adequate extractor solvent.

Examples of extractor solvents include, but are not limited to water, methanol, ethanol, propanol, isopropanol, propyleneglycol, acid solution, ethyl acetate, dichloromethane, chloroform, hexane, glycerine, acetone, petroleum ether, supercritical fluid, and a combination thereof and similar.

Preferentially, in accordance with the present invention, the extraction process consists in maceration and the extractor solvent is a hydro-alcoholic solution of water:ethanol, in which the ratio of water is less than the ratio of alcohol, i.e. using ratios of 1:9, 2:8, 3:7, 4:6 and 1:1. But, preferentially, the water:alcohol ratio is of 3:7. The extraction may occur in the presence or absence of light and/or oxygen, under agitation or not, for a period of approximately $\leq$10 days.

The extraction may occur in the presence or absence of light and/or oxygen, under agitation or not, for a period of approximately 10 days.

The ratio of extractor solvent:plant material used in the extraction procedure may vary from 1:1 to 20:1. More specifically, the extractor solvent:plant material is of 10:1.

In accordance with the present invention, the process for obtaining the extracts requires a filtration process for the elimination of the plant material residue. The filtration procedures include, but are not limited to deep or superficial filtration, using different types of filter materials.

The extract concentration process stage may be undertaken through the use of a procedure selected amongst techniques of reduced-pressure evaporation, heat-convection evaporation, heating, a combination thereof and similars.

More preferentially, the extract concentration procedure refers to the reduced-pressure evaporation technique, using a heating temperature of approximately $\leq$70° C. and a vacuum between 200 and 400 mmHg, which is capable of providing a concentration of approximately 20% to 50% solids in the extract and sufficient to eliminate 100% of the alcohol.

Following concentration of the extract, the pasteurisation stage of the soft extract aiming to extinguish eventual microbial contamination is especially useful to the process. The pasteurisation stage is particularly applicable when performed at a temperature of approximately 95° C. for 3 minutes, at least.

It is known that plant extracts generally contain pigments, such as chlorophyll and insoluble materials that may lead to an undesirable visual aspect of the extracts. Therefore, in accordance to a preferred aspect of the present invention, a stage for the elimination of these elements or depigmentation may optionally be used following the extract concentration stage in the process for obtaining a standard extract. Pigments and insoluble materials may be partly or totally removed from the extracts, for example, through treatment with active charcoal or adsorption resin, membrane ultrafiltration and the similar.

More specifically, the use of ultrafiltration through polymeric membranes with pore sizes between 5 and 100 kDa, under the impulse of gravity or pressure.

The membrane ultrafiltration may also be useful for removing oxidases from extracts, especially those with a high molecular weight, such as laccase. The elimination of oxidases may be especially desirable for the stabilisation of standard extracts.

Other processes are known in the state of the art for performing the extract stabilization stage. It is possible, for example, to stabilise an extract through the addition of a sufficient quantity of one or more stabilisation agents or antioxidants such as, but not limited to: butylhydroxytoluene, butylhydroxyanisol, ascorbic acid and its derivatives, octyldodecanol, cysteine, glutathione, and similars. Thus, optionally, it is possible to include an extract stabilisation stage, relating to the addition of a stabilising agent at a concentration of 0.01 to 5% and preferably of 0.2 to 1% based on the extract. In accordance with a preferred aspect, a stabilising agent may be added during or following the extraction process.

In accordance with an alternative mode of the present invention, a drying stage of the extract after the concentration stage may be used for obtaining a standard dry extract.

The drying procedure, in accordance with the present invention may be selected from a group comprising lyophilisation, drying by atomisation (spray-drying), evaporation under reduced pressure, drying by heat convection, or a combination thereof. More preferentially, the drying procedure in accordance with the present invention refers to the spray-drying technique.

Drying adjuvants may be used advantageously in the drying procedure by spray-drying. Examples of drying adjuvants include, but are not limited to: colloidal silicon dioxide, modified cassava starch, tricalcium phosphate, maltodextrin, cyclodextrins, microcrystalline cellulose, lactose, a combination thereof and similars. The use of drying adjuvants is especially useful in quantities of 10 to 40% in relation to the ratio of total solids in the final product.

In accordance with an optional aspect, an additional microbial decontamination stage may be performed after the drying stage. The techniques of gamma ray radiation, ultraviolet radiation and similars are particularly useful in this case.

The process for obtaining a standard extract in accordance with the present invention requires a qualitative and quantitative analysis stage by means of duly validated analytic methodologies associated to linearity, accuracy, precision, specificity and robustness.

In accordance with the present invention, the analytic methodologies particularly useful for the qualitative and quantitative characterisation include, but are not limited to Thin layer chromatography (TLC), paper chromatography, Gas Chromatography (GC), column chromatography (CC), high performance liquid chromatography (HPLC), mass spectrometry (MS), thermo-analytic techniques and the similar.

Figure 1A:
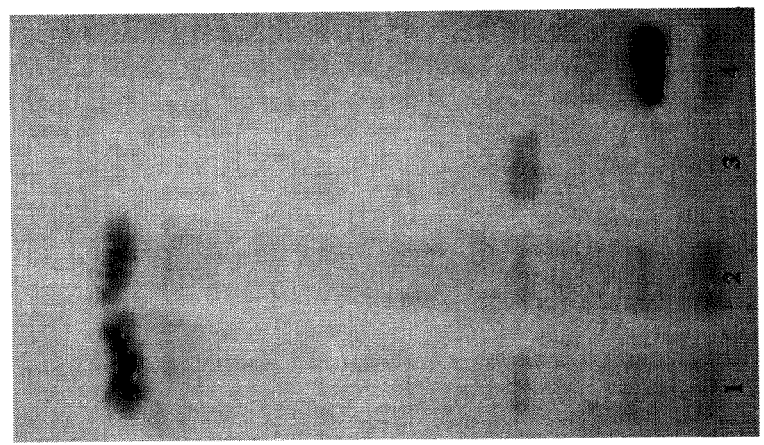
Figure 2A:
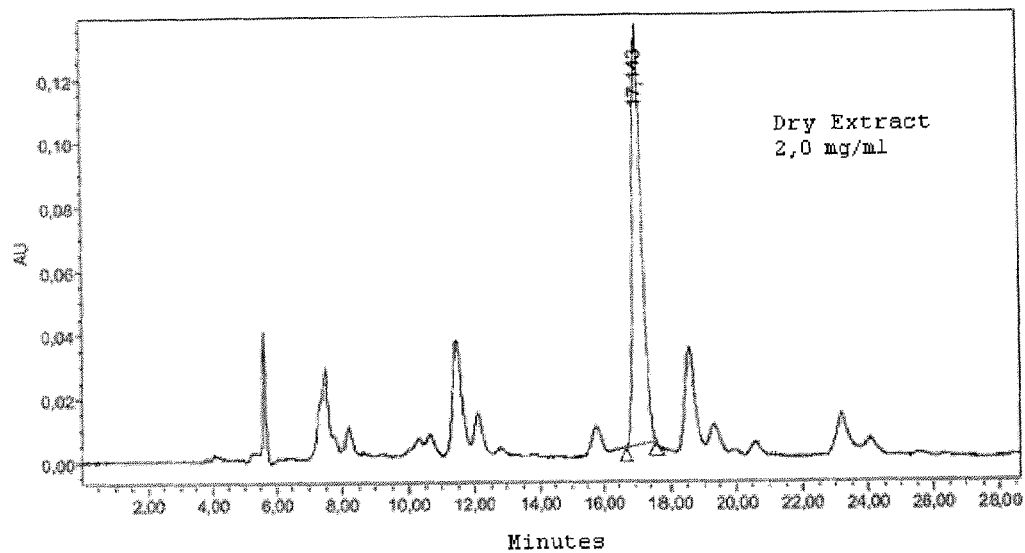
FIG. 2 shows the results obtained from the analysis of the extract of *Aleurites moluccana* by High Performance Liquid Chromatography (HPLC) with (A) being the dry extract and (B) being the soft extract.
Figure 2B:
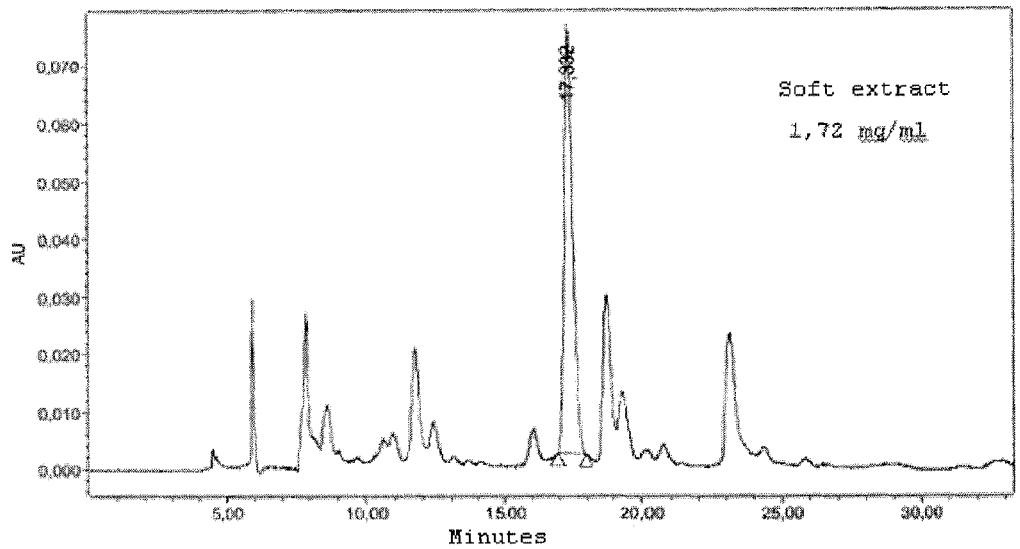

In accordance with the present invention, a standardized extract may be more particularly analysed by TLC, presenting a chromatographic profile that is peculiar such as that presented in FIG. 1 (A and B) and by HPLC as presented in FIG. 2 (A and B). FIG. 1 (A) shows the results of the chromatogaphic profile obtained for the soft extract and the dry extract of *Aleurites moluccana*, when assessed on a chromatographic plate, developed using a mixture of AcOEt:Acetone:$H_2O$ 25:8:2 as an eluant and revealed with a solution of ferric chloride 3%. The first stain refers to the soft extract (EtOH:$H_2O$ 9:1), the second stain to the dry extract, the third stain to the swertisin standard and the fourth to 2"-O-rhamnosylswertisin. FIG. 1 (B) shows the results of the chromatogaphic profile obtained for the soft extract and the dry extract of *Aleurites moluccana*, when assessed on a chromatographic plate, developed using a mixture of hexane:AcOEt 85:15 and revealed with a solution of hot sulphuric anisaldehyde. The first stain refers to the soft extract (EtOH:$H_2O$ 9:1), the second stain to the dry extract, the third stain to the alpha and beta-amyrin standard, the fourth to alpha and beta-amirinon standard and the fifth stigmasterol and beta-sitosterol standard. FIG. 2 (A) shows the results obtained for the dry extract of *Aleurites moluccana* when assessed by High performance liquid chromatography (HPLC). The extract was initially dissolved in methanol (20% of final volume), sonicated for 5 min, followed by the addition of water acidified to pH 3.57 (20% of final volume). The volume was then completed with a mixture of methanol/water acidified 50:50 to a concentration of 1 to 2 mg/ml. After filtration of the sample through a 0.22 μm membrane filter, 20 μL of the solution was injected by means of a reversed phase column, where groups $C_{18}$ are chemically linked to silica, presenting a length of 10 to 25 cm and an internal diameter of 4 to 6 mm. A PDA (diode array) type detector was used to monitor the chromatographic run at 254 and 338 nm. Separation was performed using a linear gradient mobile phase, composed initially of methanol/water acidified acidified to pH 3.57:acetonitrile (20:15:65) at a flow of 0.5 to 1 ml/min, to a proportion of 10:15:75, after 20 min, with a pressure variation of 2.000 to 3.000 psi. FIG. 2 (B) shows the results obtained for the soft extract of *Aleurites moluccana* when assessed by High performance liquid chromatography (HPLC) in the same manner used for FIG. 2 (A).

In accordance with the present invention, a standard dry extract or soft extract is particularly characterised by presenting a 2"-O-rhamnosylswertisin marker ratio of 0.05 to 15% of its composition.

In accordance with the present invention, a fractioning stage of the standard extract may be particularly useful for concentrating the substances potentially related to pharmacological activities of the species. Several fractioning processes are known in the state of the art. More particularly, the use of a column with different chromatographic supports (i.e. silica, Sephadex®, aluminum, cellulose and similars) and adequate eluents or liquid-liquid partition using hexane, dichloromethane, chloroform, ethyl acetate, butanol and similars is useful. More preferentially, hexane, dichloromethane, and chloroform may be used to obtain a concentrated fraction relating to the substances of non-polar character in the extract, such as beta-amyrin, alpha-amyrin; and ethyl acetate and butanol may be used to obtain a concentrated fraction relating to the substances of polar character in the extract, such as swertisin and 2"-O-rhamnosylswertisin.

The preferred embodiments of the present invention for obtaining and analysing a standard extract are described in detail in Examples I, II and III.

Isolation, Purification and Characterisation of the Marker

The selection, isolation, purification and characterisation of a constituent/marker of an extract are particularly necessary for the quantification and standardisation of the extracts.

In accordance with the present invention, the flavonoid 2"-O-rhamnosylswertisin was established as being the most appropriate marker for the process of obtaining a standard extract. This selection is justified because it constitutes a main compound of the plant, it is more discriminatory of the species, it is associated to the pharmacological properties of the extract and by the fact of being a flavonoid, which may be indicative of the extract's stability, during technological processing or storage. (Sonaglio, D. et al., *Desenvolvimento Tecnológico e Produção de Fitoterápicos*. In: SIMÕES et al. (Org.) *Farmacognosia: Da Planta ao Medicamento*. Porto Alegre: Editora da Universidade, 1999, 221-258).

These quantification and standardisation procedures of the extracts occur according to the following stages:

I. Isolation,
II. Purification, and
III. Characterisation of the Marker.

The isolation of the 2"-O-rhamnosylswertisin marker (Stage I) may be performed by techniques that include, but are not limited to, liquid-liquid partition, preparative TLC (PTLC), column chromatography, centrifuge chromatography, preparative or semi-preparative HPLC (PHPLC), a combination thereof and similars.

More preferentially, the isolation of the 2"-O-rhamnosylswertisin marker may be performed using, sequentially, the techniques of liquid-liquid partition, open column chromatography and preparative TLC (PTLC), using silica 60 as stationary phase for the two latter and a chloroform:methanol mixture as an eluant or preparative or semi-preparative HPLC using preparative or semi-preparative C18 type reversed phase columns with a particle size of 10 μm, using a linear gradient of methanol:acetonitrile:acidified water as a mobile phase, monitored at 254 to 338 nm.

The purification of 2"-O-rhamnosylswertisin marker (Stage II) may be performed by techniques that include, but are not limited to, preparative TLC and preparative or semi-preparative HPLC.

More preferentially, the purification of the 2"-O-rhamnosylswertisin marker may be performed using preparative TLC, using silica 60 as stationary phase and a chloroform:methanol mixture as an eluant. Alternatively, the preparative or semi-preparative HPLC technique may be used, using preparative or semi-preparative $C_{18}$ type reversed phase columns with a particle size of 10 μm, using a linear gradient of methanol:acetonitrile:acidified water as a mobile phase, monitored at 254 to 338 nm.

In accordance with the present invention, the use of the above mentioned procedures should achieve a purity rate equivalent to approximately >90%.

In accordance with the present invention, the qualitative and quantitative analysis of the isolated and purified 2"-O-rhamnosylswertisin marker, or in other words, its characterisation (Stage III) may be performed using techniques that include, but are not limited to hydrogen and carbon-13 nuclear magnetic resonance (NMR), infrared spectrophotometry (IV), ultraviolet spectrophotometry (UV), HPLC, TLC and thermal analysis.

Figure 3A:
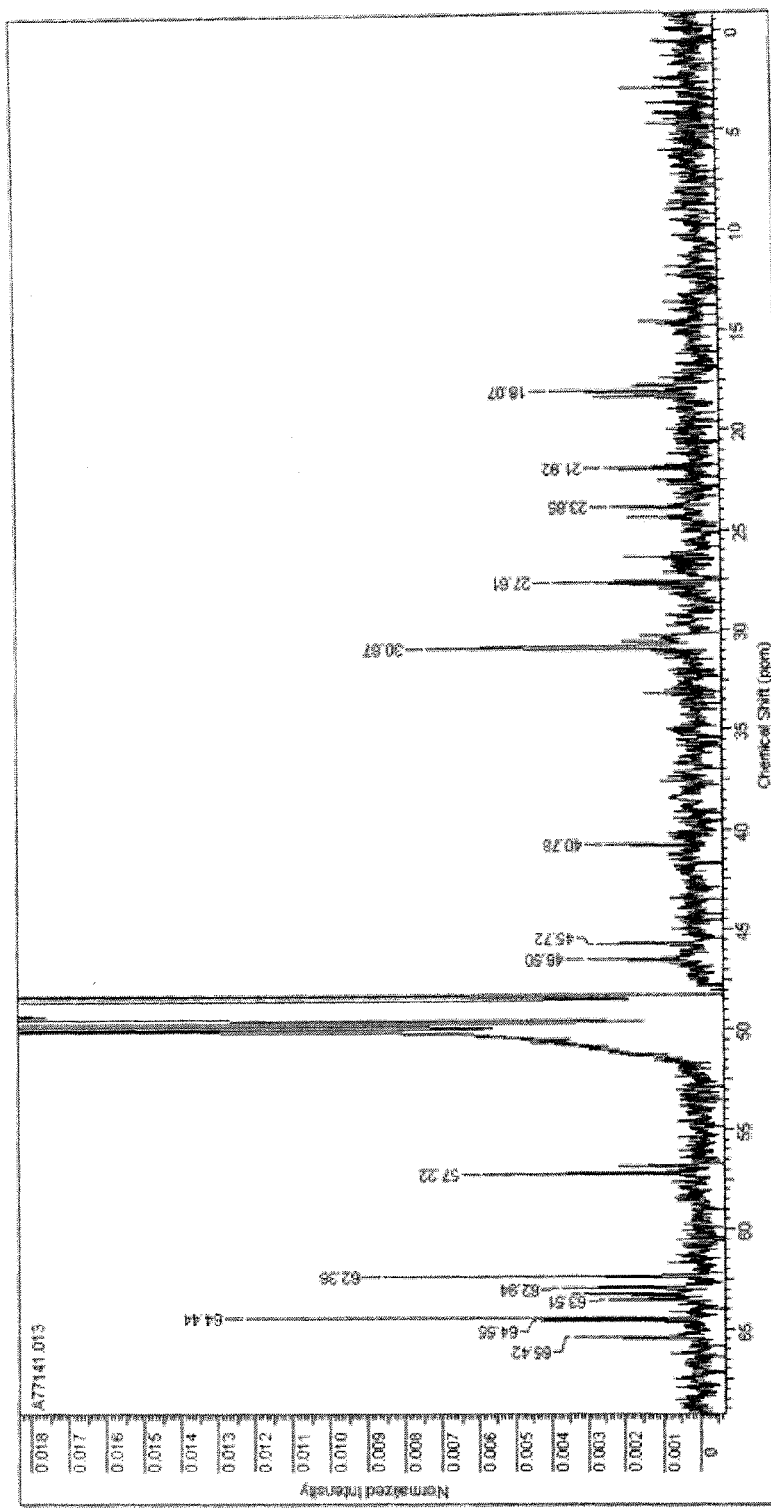
FIG. 3 shows the results obtained from the analysis of the marker 2"-O-rhamnosylswertisin by Carbon-13 Nuclear Magnetic Resonance (NMR $C^{13}$) (300 MHz) in deuterated methanol (MeOD), with (A) being in the region of 65 to 0 ppm (300 MHz); (B) being in the region of 86 to 54 ppm (300 MHz) and (C) being in the region of 205 to 85 ppm (300 MHz).
Figure 3B:
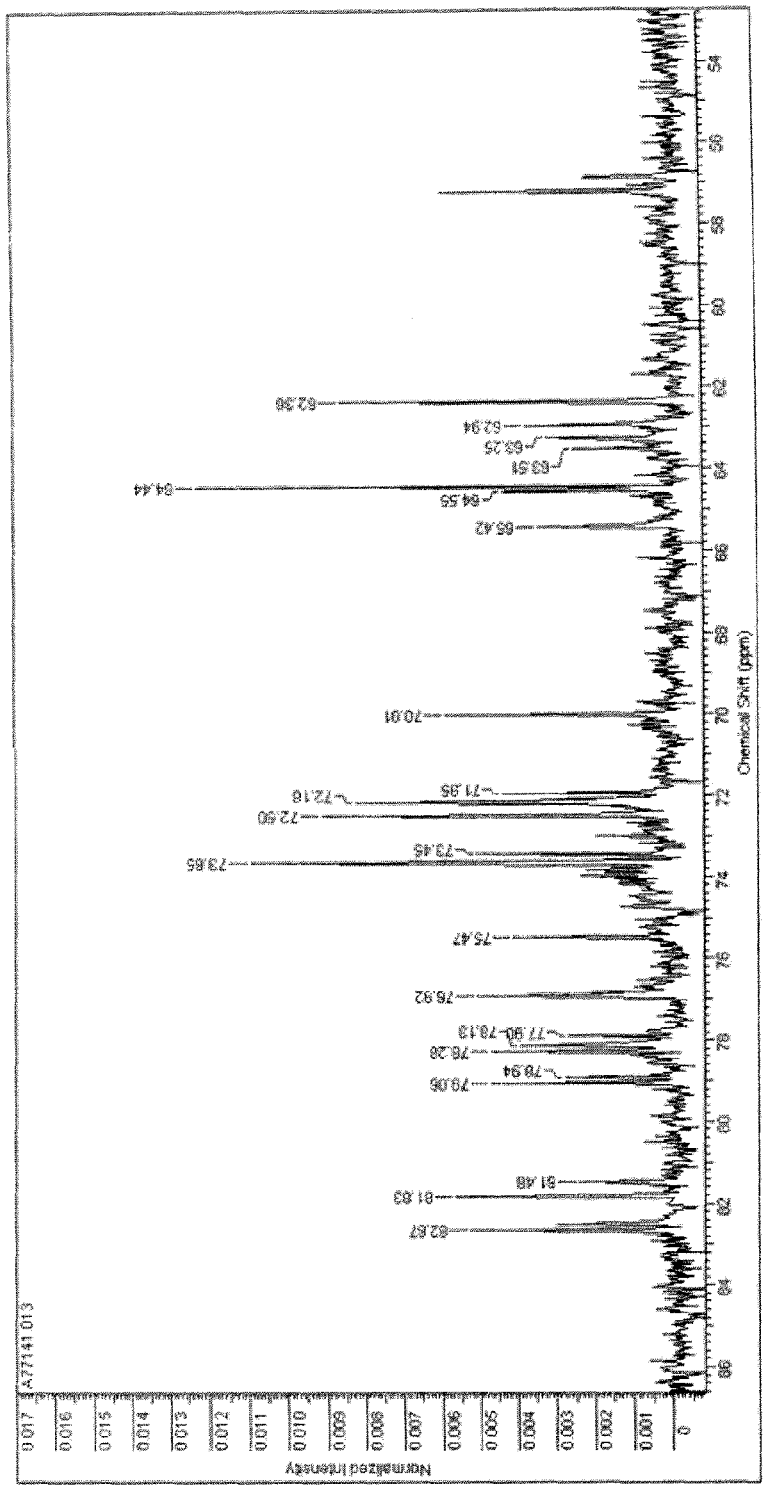
Figure 3C:
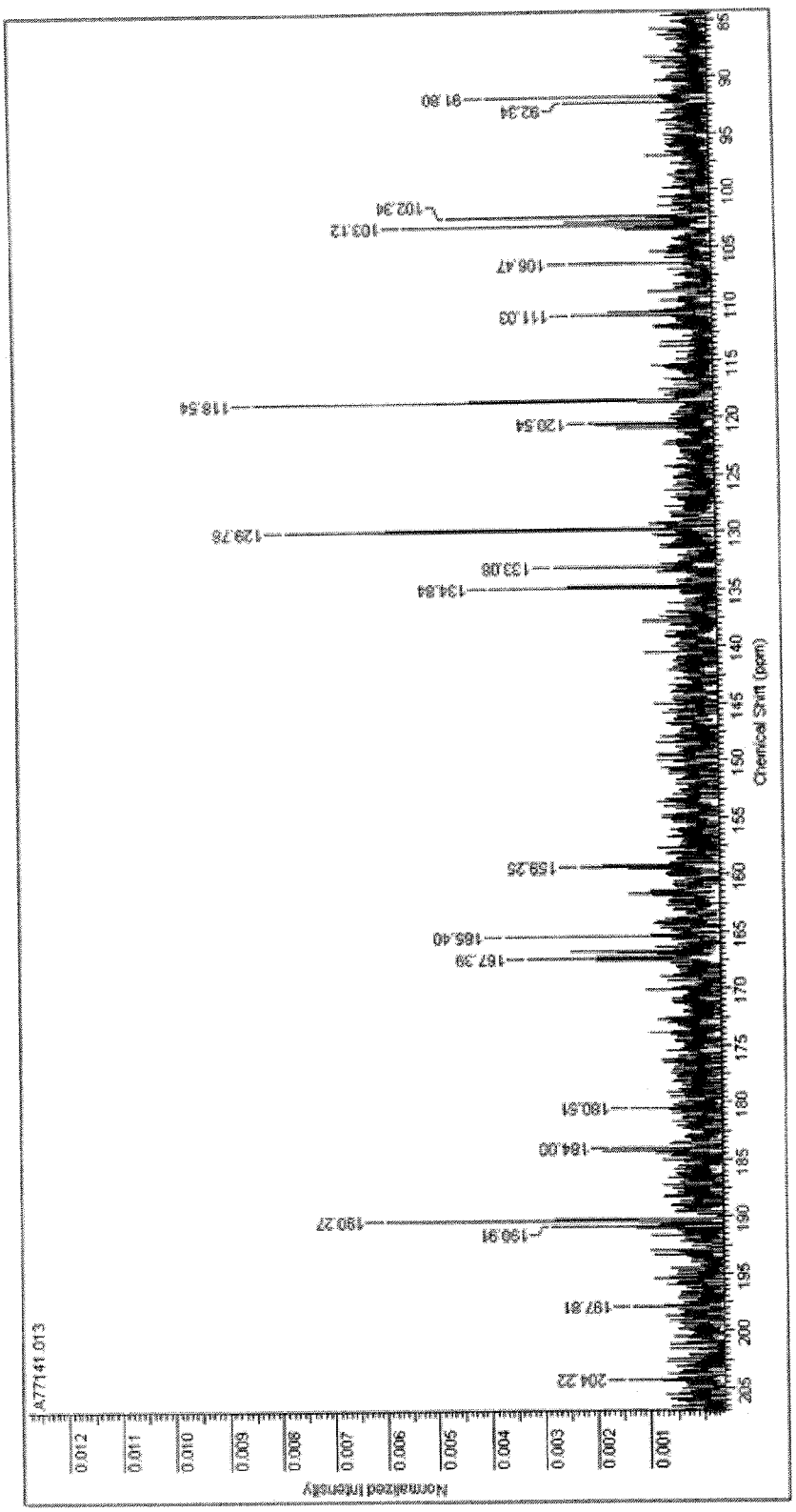
Figure 4A:
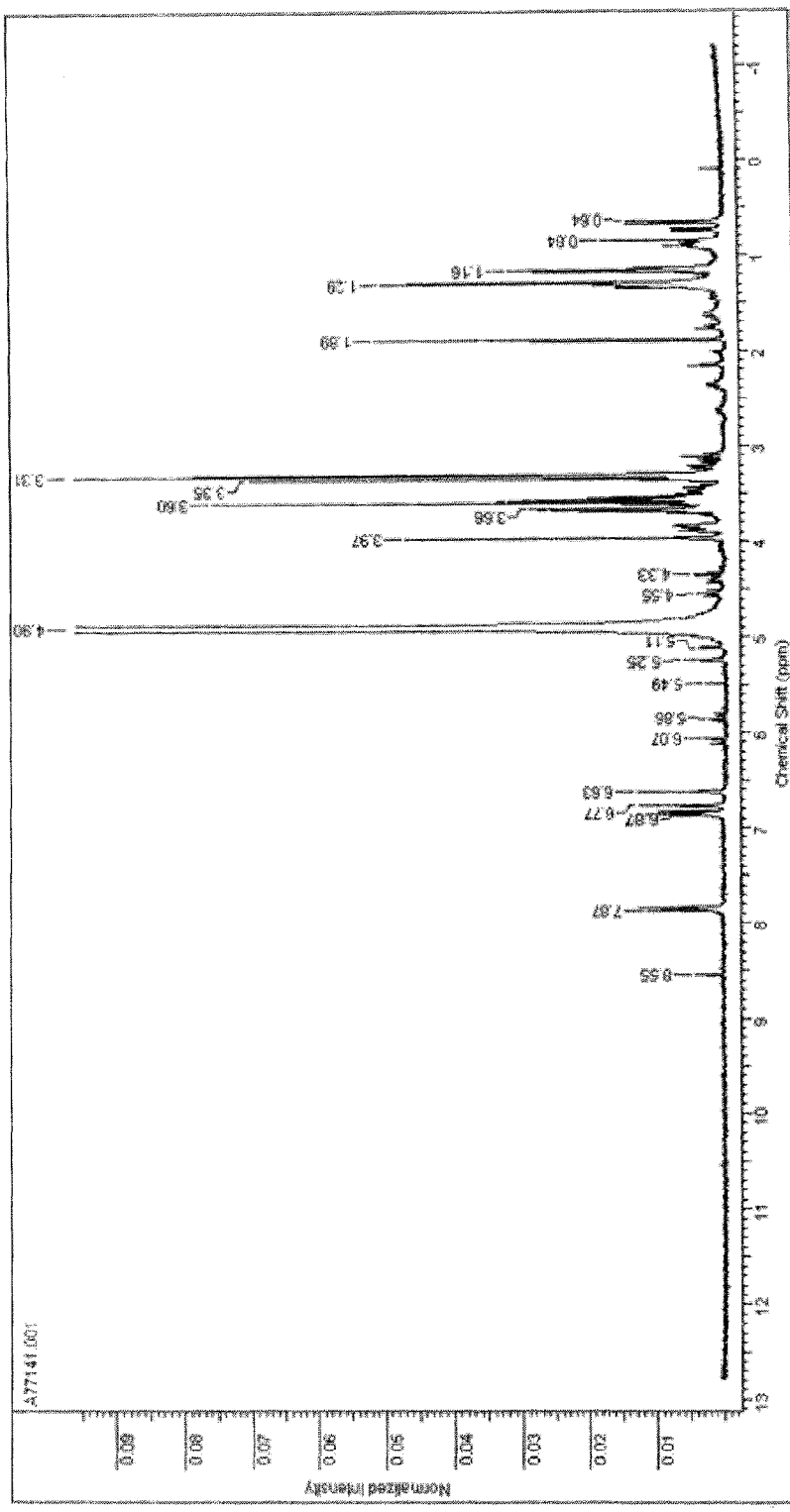
FIG. 4 shows the results obtained from the analysis of the marker 2"-O-rhamnosylswertisin by Hydrogen-1 Nuclear Magnetic Resonance (NMR $H^1$) (300 MHz) in deuterated methanol (MeOD), with (A) being in the region of 13 to 0 ppm (300 MHz); (B) being in the region of 8.5 to 5.5 ppm (300 MHz) and (C) being in the region of 4.5 to 0.5 ppm (300 MHz).
Figure 4B:
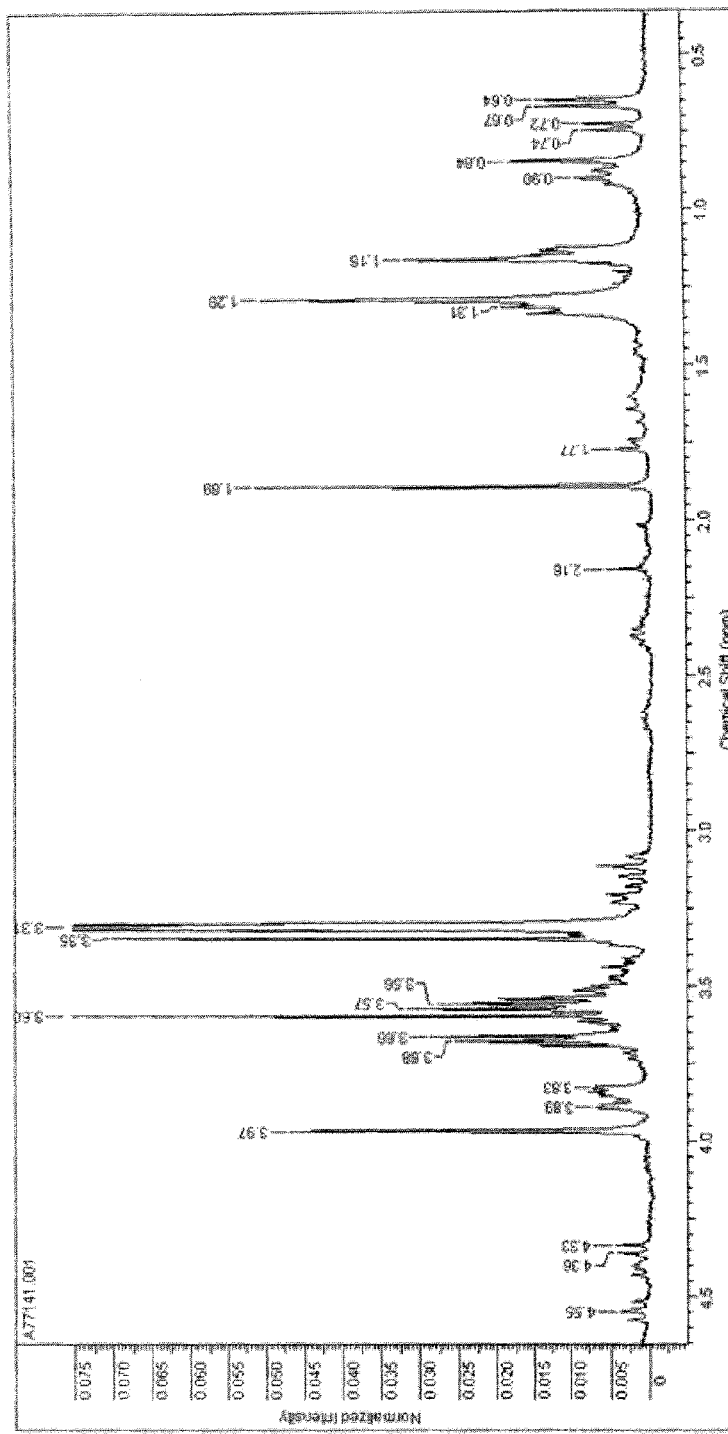
Figure 4C:
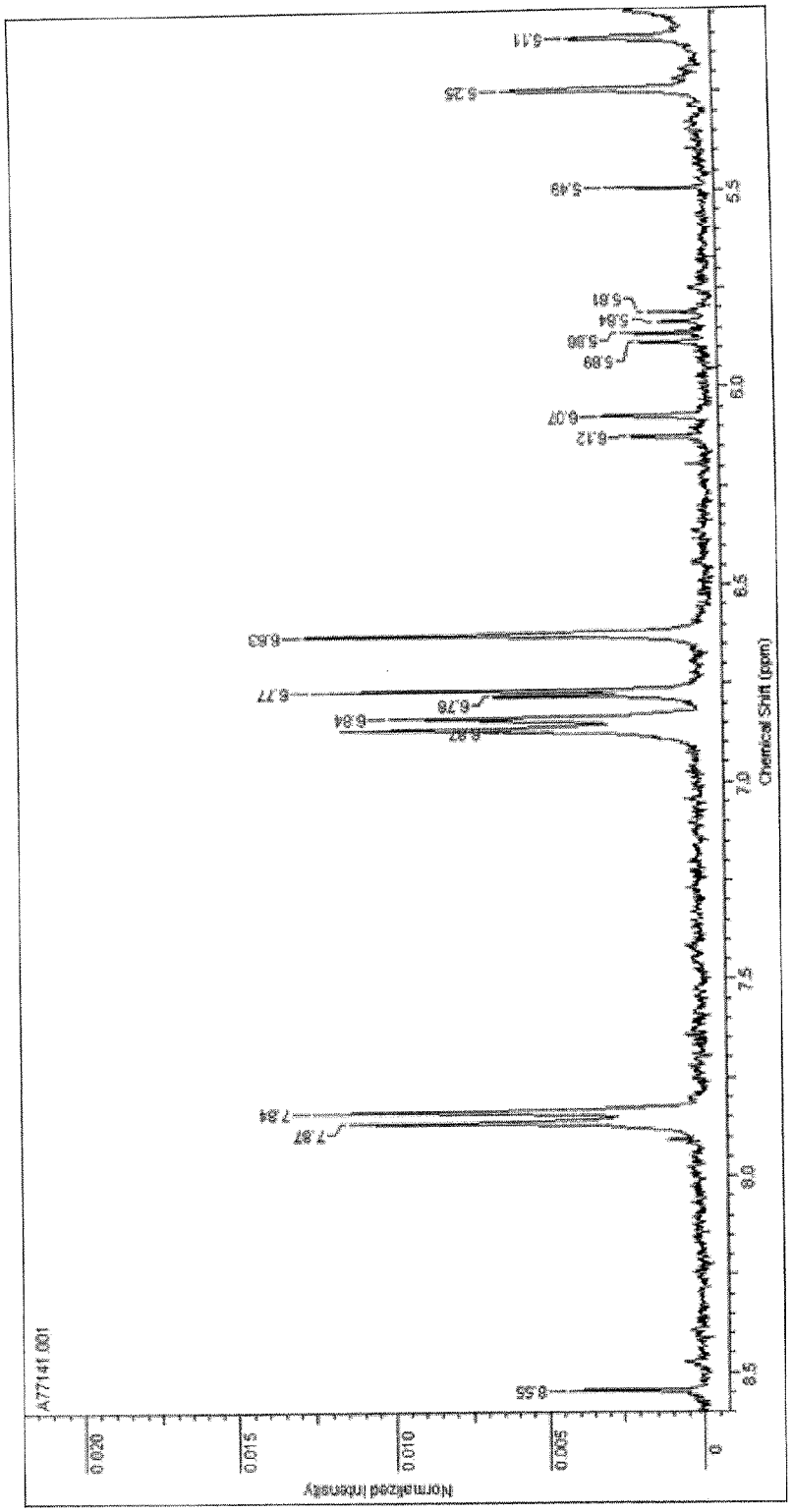
Figure 5A:
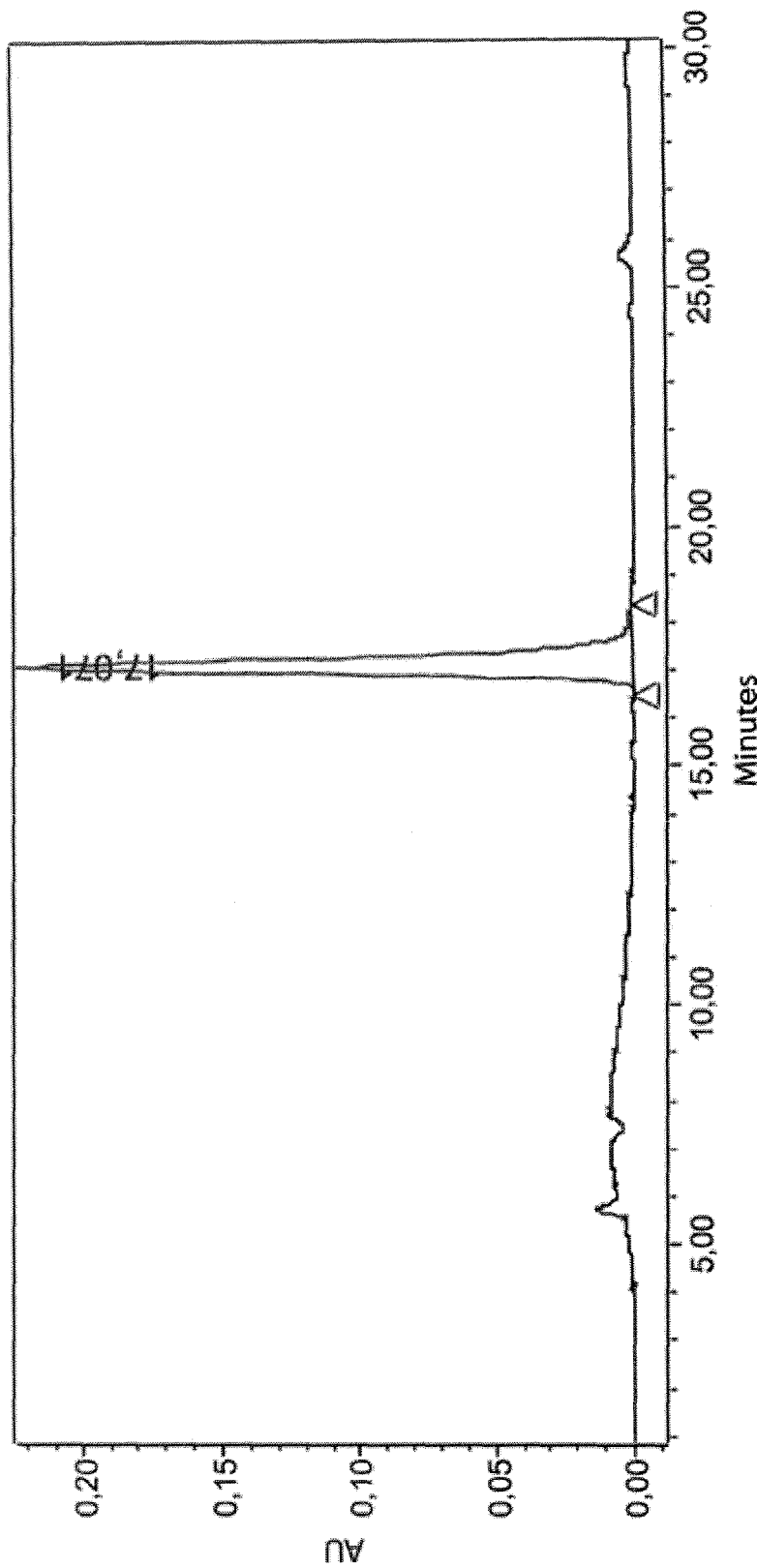
FIG. 5 shows the HPLC chromatogram of the standard 2"-O-rhamnosylswertisin purified by PTLC (AMSR170707) at 145 µg/ml, with (A) being at 338 nm, and (B) being in the ultraviolet region at 213.8, 270.3 and 336.8 nm.
Figure 5B:
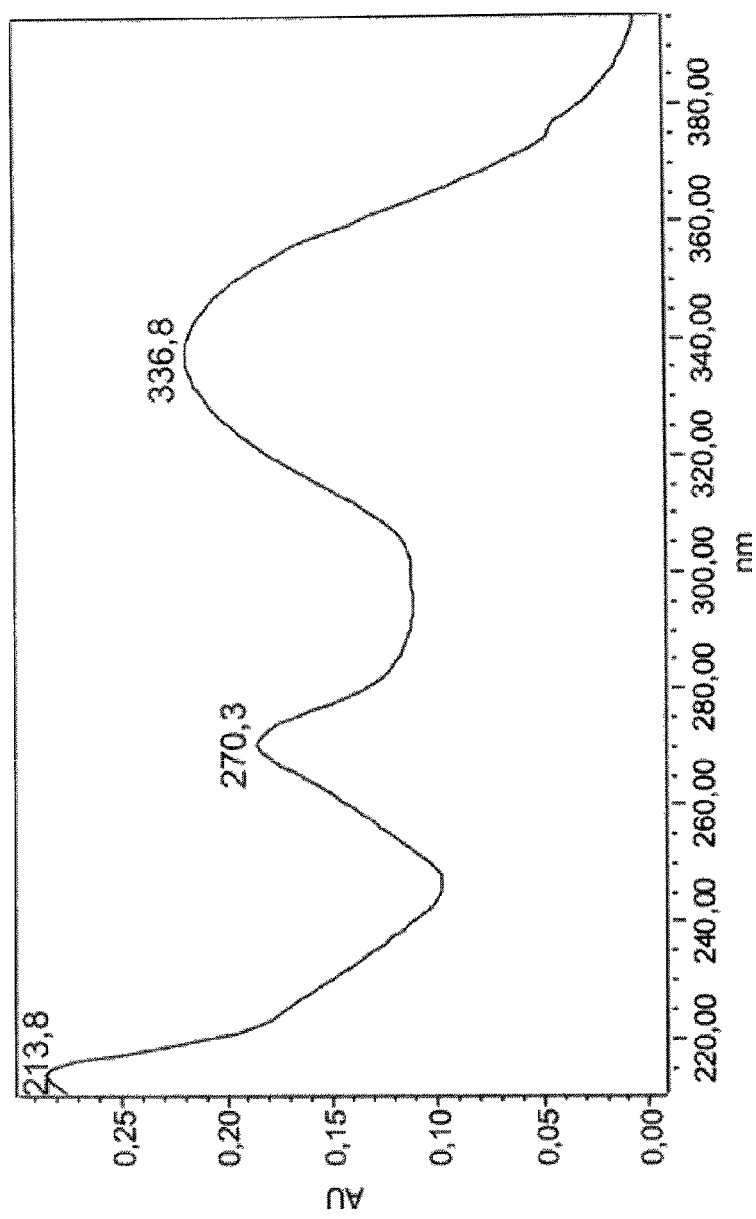
Figure 6:
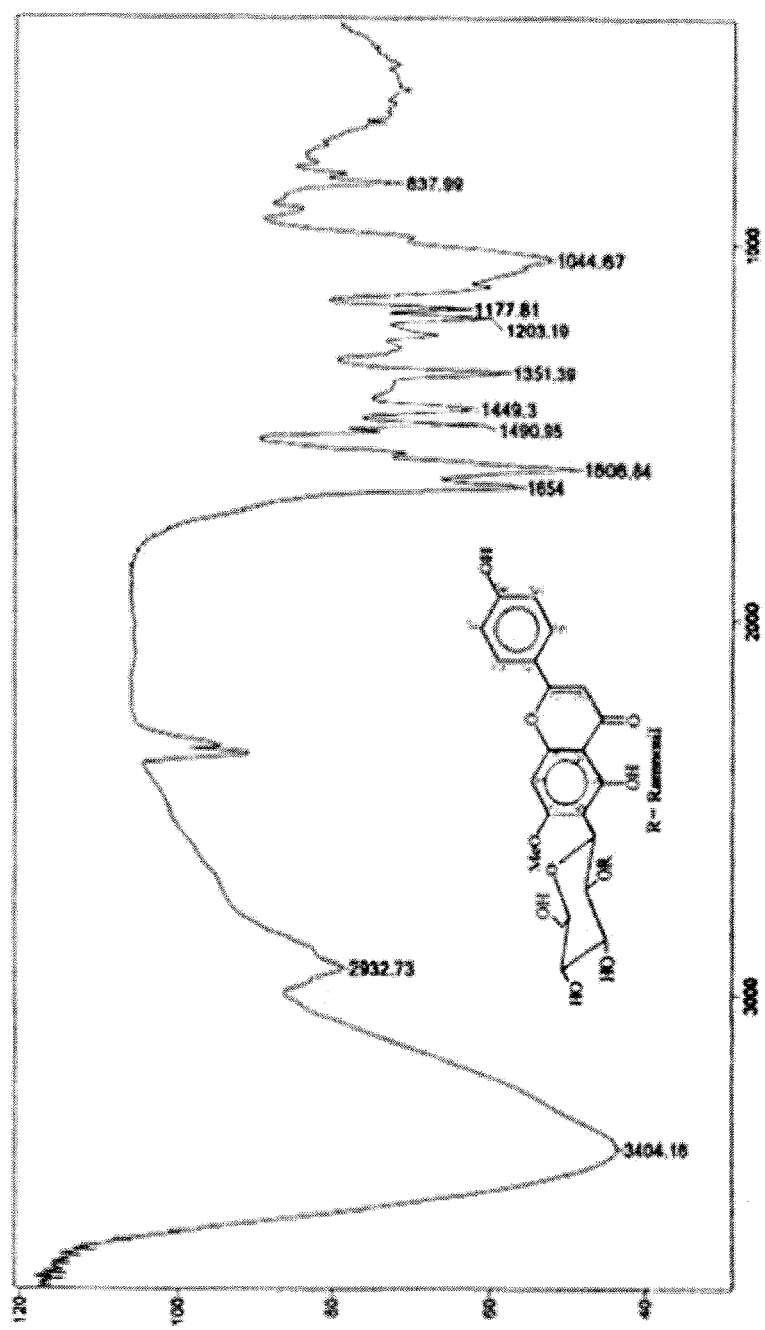
FIG. 6 shows the results obtained for the marker 2"-O-rhamnosylswertisin when assessed by Infrared Spectroscopy with a KBr pellet.

The isolated and purified 2"-O-rhamnosylswertisin marker is particularly characterised by NMR and HPLC. FIG. 3 shows the results obtained with the marker when assessed by Carbon-13 Nuclear Magnetic Resonance (NMR $C^{13}$), (300 MHz) in deuterated methanol (MeOD), with (A) being in the region of 65 to 0 ppm (300 MHz); (B) being in the region of 86 to 54 ppm (300 MHz) and (C) being in the region of 205 to 85 ppm (300 MHz). FIG. 4 shows the results obtained with the 2"-O-rhamnosylswertisin marker when assessed by hydrogen Nuclear Magnetic Resonance (NMR $H^1$), (300 MHz) in deuterated methanol (MeOD), with (A) being in the region of 13 to 0 ppm (300 MHz); (B) being in the region of 8.5 to 5.5 ppm (300 MHz) and (C) being in the region of 4.5 to 0.5 ppm (300 MHz). The characterisation of the marker by HPLC is shown in FIG. 5 which shows the chromatographic profile by means of a HPLC chromatogram of the standard 2"-O-rhamnosylswertisin purified by PTLC (AMSR170707) at 145 μg/ml, in 338 nm, which eluted in approximately 17 min, thus demonstrating success in purification of the marker, as indicated by the presence of a single peak on the chromatogram. FIG. 5 (B) shows the results and more specifically the absorption profile of a typical flavonoid peak, obtained with 2"-O-rhamnosylswertisin marker with maximum absorptions of 213.8, 270.3 and 336.8 nm when assessed by scanning the ultraviolet spectrum in the Photo Diode Array (PDA) of the Liquid Chromatograph, in the same manner as for FIG. 2 (A). FIG. 6 shows the infra-red absorption spectrum typical of flavonoids.

A preferred embodiment of the present invention for the isolation, purification and analysis of the marker is described in more detail in Example IV.

Pharmacological Characterisation of the Standard Extracts

The standard extracts, in accordance with the present invention, may be characterised as to their pharmacological activity in animal pain models by nociception, hypernociception, neuropathic pain, inflammation and fever.

Several animal models may be applied to the pharmacological characterisation of an extract with antinociceptive, anti-inflammatory and antipyretic properties, and these include: 1. Abdominal contortion tests induced by acetic acid; 2. Randal-Sellito Test; 3. Mechanical hypernociception models (of inflammatory and/or neuropathic origin); 4. Formalin test; 5. Hot plate assays; 6. Neuropathic pain assays; 7. Paw and ear edema trials in rats and/or mice, induced by different phlogistic agents; 8. Pleurisy model, induced by different phlogistic agents; 9. Arthritis models induced by Freund adjuvants; 10. Hyperthermia models induced by LPS; 11. Evaluation of undesirable effects; and similars.

The standard extracts, in accordance with the present invention, when characterised as to their pharmacological activity, demonstrate antinociceptive, anti-inflammatory and antipyretic properties, as described in greater detail below.

Antinociceptive Effects of the Extracts of *Aleurites moluccana* Using the Abdominal Contortion Model Induced by Acetic Acid.

Figure 7:
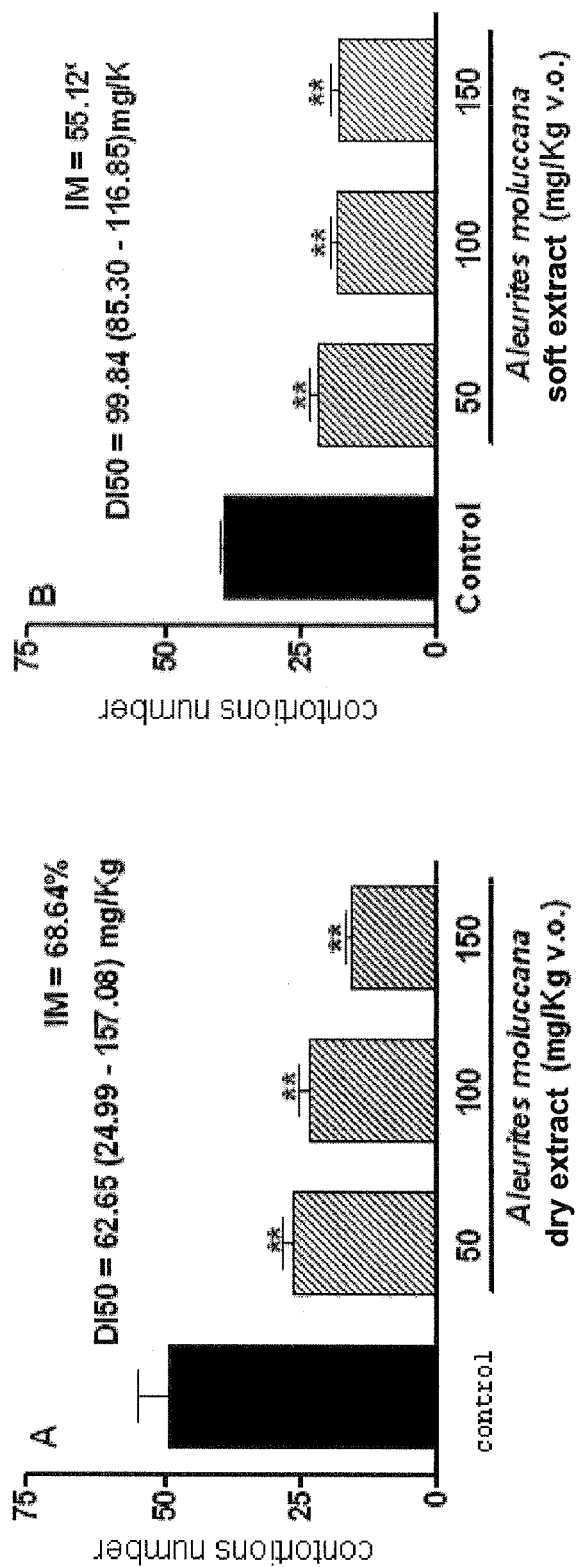
FIG. 7 shows the results obtained from the extract of *Aleurites moluccana*, with (A) being the dry extract, (B) being the soft extract and (C) being the control group.

The oral administration of the dry and soft extracts is capable of significantly inhibiting in a dose dependent manner the number of contortions induced by intraplantar injections of acetic acid in mice, and DI50s of 62.65 (24.99-157.64) mg/kg, 99.84 (85.30-116.85) mg/Kg, respectively. FIG. 7 shows the results obtained with the extracts of *Aleurites moluccana*, in (A) (dry extract) and in (B) (soft extract), administered orally, in the abdominal contortion model induced by acetic acid. Each column represents the average of 8 to 10 animals and the vertical bars indicate the ASEs. The results differ significantly in relation to the control group (see FIG. 7 (C)), **$P<0.01$. The inhibition values (IM) obtained are stipulated at 68.64±1.22%; 55.12±2.13% and 64.0±1.65%; 63.5%, and 96.9%, for the dry and soft extracts, respectively, as shown in Table 1 below, compared to the pharmaceuticals used in clinical practice.

TABLE 1

Comparative data of DI50 and IM in the abdominal contortion model induced by acetic acid: oral administration.

| Group | IM (%) | DI50 (mg/kg) |
|---|---|---|
| Dry Extract | 68.6 | 62.65 (24.99-157.08) |
| Soft extract | 55.12 | 99.84 (85.30-116.85) |

TABLE 1-continued

Comparative data of DI50 and IM in the abdominal contortion model induced by acetic acid: oral administration.

| Group | IM (%) | DI50 (mg/kg) |
|---|---|---|
| Indomethacin | 72.0 | 189.95 (142.51-253.17) |
| AAS | 64.5 | 364.1 (303.4-437.0) |
| Diclophenac | 51.6 | 443.07 (396.18-495.50) |

Antinociceptive Effects of the Extracts of *Aleurites moluccana* Using the Pain Model Induced by Formalin.

Figure 8:
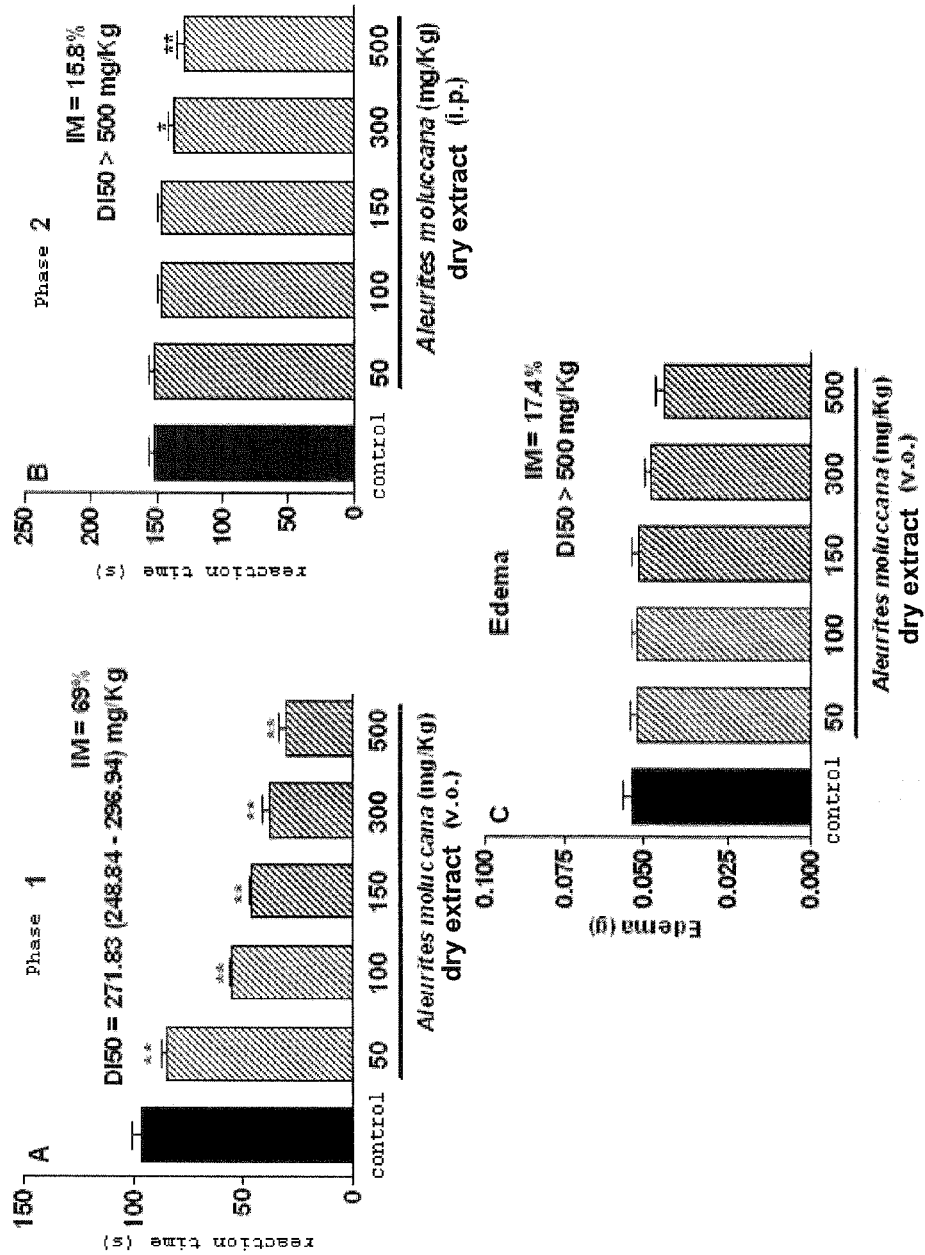
FIG. 8 shows the results obtained from the dry extract of *Aleurites moluccana*, with (A) being in Phase I, (B) being in Phase II and (C) being the Edema (control group).

The oral administration of the dry extract, in doses of 50 to 500 mg/kg, is capable of significantly inhibiting in a dose dependent manner both the neurogenic phase and the inflammatory phase of nociception induced by intraplantar injections of formalin, with an inhibition of 69±2.34% and 15.84±1.98% for the first and second phase of formalin, respectively, and DI50% of 271.83 (248.84-296.94) mg/kg for the first phase of the test. FIG. 8 shows the results of this experiment, with Phase I being in (A), Phase II being in (B) and the Edema being in (C). Each column represents the average of 8 to 10 animals and the vertical bars indicate the ASEs. The results differ significantly in relation to the control group (C), *$P<0.05$ and $P<0.01$ or, in other words, the same extract was not capable of reducing the edema of the paw induced by formalin (FIG. 8** (C)).

Figure 9:
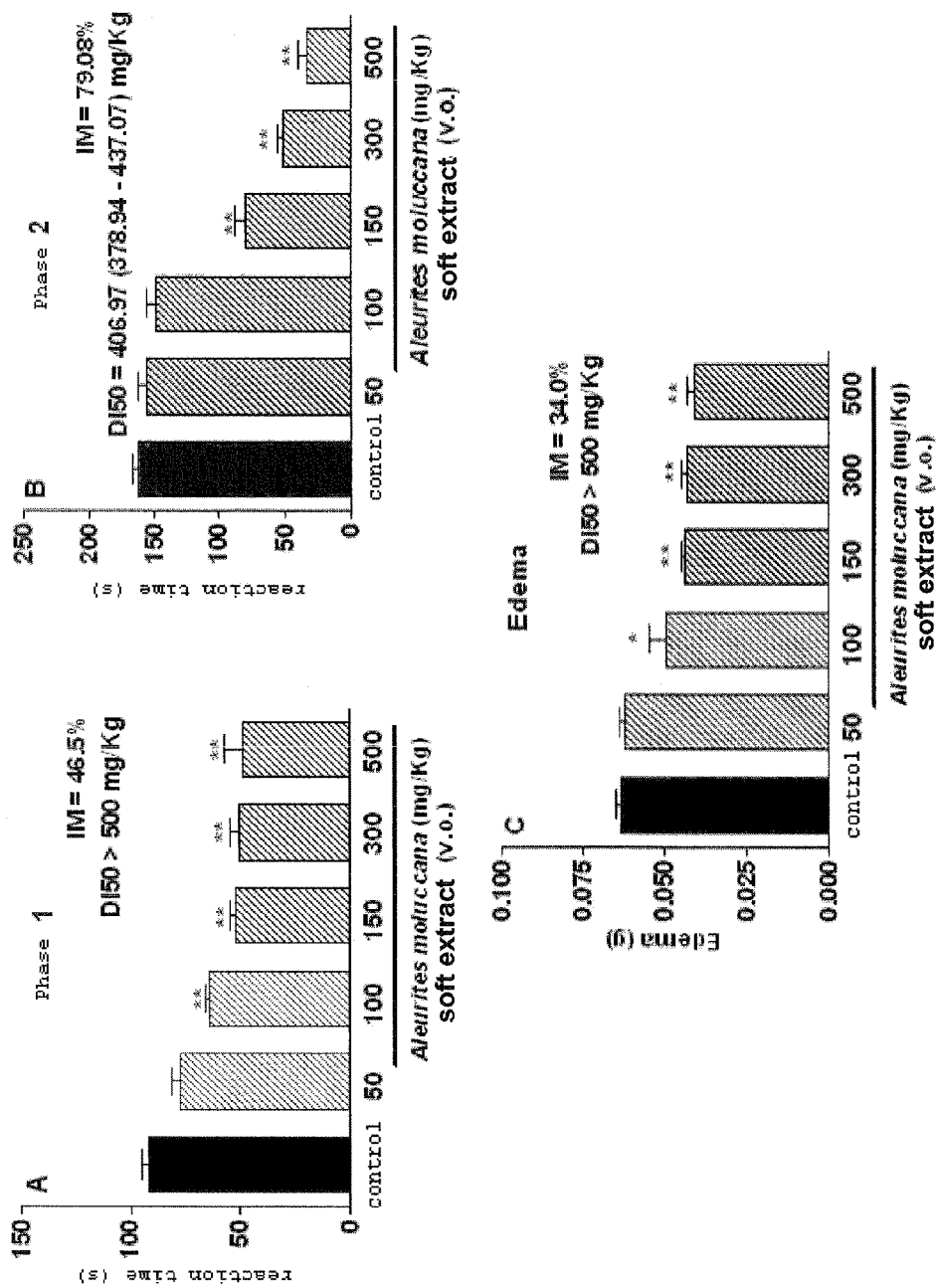
FIG. 9 shows the results obtained from the soft extract of *Aleurites moluccana*, with (A) being in Phase I, (B) being in Phase II and (C) being the Edema (control group).

The oral administration of the soft extract of *Aleurites moluccana*, in doses of 50 to 500 mg/kg administered orally, is capable of significantly inhibiting in a dose dependent manner both the neurogenic phase and the inflammatory phase of nociception induced by intraplantar injections of formalin, with an inhibition of 46.5±3.41% and 79.08±2.54% for the first and second phase of formalin, respectively, and DI50% superior to 500 mg/kg for the second phase of the test. FIG. 9 shows the results of this experiment in the formalin induced pain model, with Phase I being in (A), Phase II being in (B) and the Edema being in (C). Each column represents an average of 8 to 10 animals and the vertical bars indicate the ASEs. The results differ significantly in relation to the control group (C), *$P<0.05$ and $P<0.01$. The same extract was capable of reducing the edema of the paw induced by formalin with an inhibition of 34% (FIG. 9** (C)). The IM and DI50 values compared to the pharmaceuticals used in clinical practice are shown in Table 2 (Phase I) and Table 3 (Phase II) below.

TABLE 2

Comparative data of DI50 and IM - formalin induced pain model - Phase I: oral administration.

| Group | IM (%) | DI50 (mg/kg) |
|---|---|---|
| Dry Extract | 69.0 | 271.83 (248.84-296.94) |
| Soft extract | 46.5 | >500 |
| Indomethacin | 7.2 | >300 |
| AAS | 12.7 | >500 |
| Diclophenac | 68.8 | 407.48 (357.56-464.37) |

TABLE 3

Comparative data of DI50 and IM - formalin induced pain model - Phase II: oral administration.

| Group | IM (%) | DI50 (mg/kg) |
|---|---|---|
| Dry Extract | 15.8 | >500 |
| Soft extract | 79.1 | ~150 |
| Indomethacin | 53.1 | 263.42 (239.83-289.35) |

TABLE 3-continued

Comparative data of DI50 and IM - formalin induced pain model - Phase II: oral administration.

| Group | IM (%) | DI50 (mg/kg) |
|---|---|---|
| AAS | 65.7 | 408.87 (391.47-427.03) |
| Diclophenac | 82.5 | 279.69 (245.47-318.67) |

Table 4 below shows the IM and DI50 values—formalin induced pain model for evaluation of the Edema compared to the pharmaceuticals used in clinical practice.

TABLE 4

Comparative data of DI50 and IM - formalin induced pain model - Edema: oral administration.

| Group | IM (%) | DI50 (mg/kg) |
|---|---|---|
| Dry Extract | 17.4 | >500 |
| Soft extract | 34.0 | >500 |
| Indomethacin | 36.5 | >300 |
| AAS | 31.7 | >500 |
| Diclophenac | 33.7 | >500 |

Antinociceptive Effects of the Extracts of *Aleurites moluccana* Using the Hot Plate Model.

Figure 10:
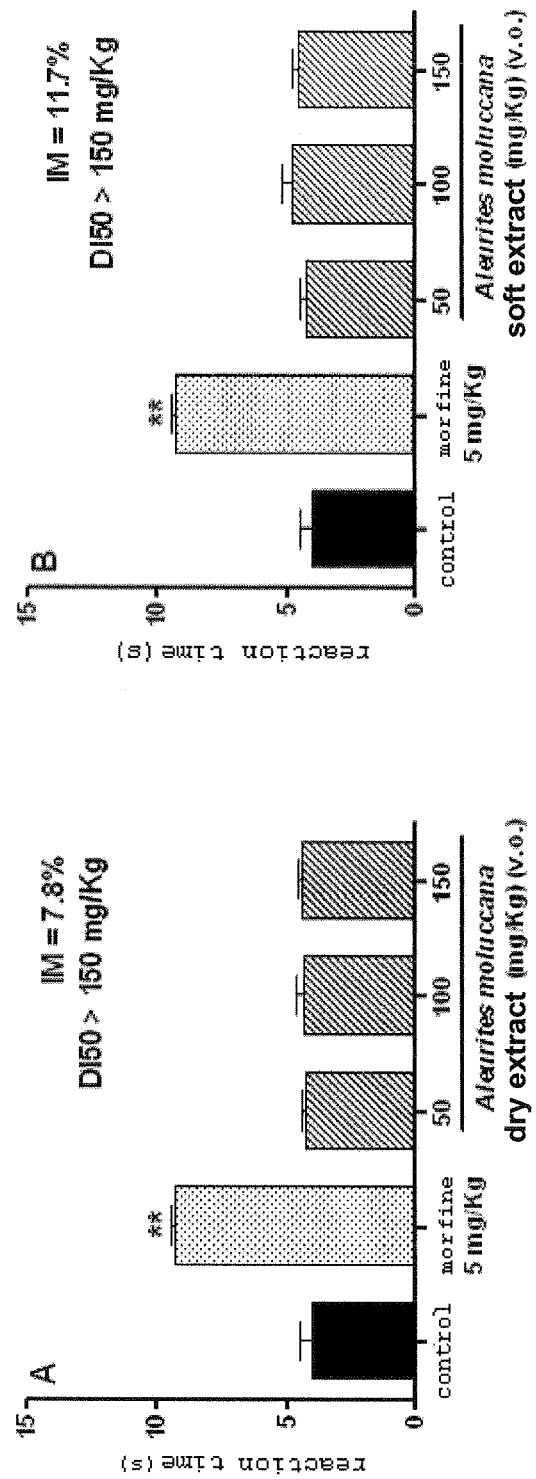
FIG. 10 shows the results obtained from the extracts of *Aleurites moluccana*, with (A) being with the dry extract (B) being the soft extract.

FIG. 10 represents the results obtained with the dry (A) and soft (B) extracts of *Aleurites moluccana*, administered orally, with the hot plate model. Each point represents the average of 8 to 10 animals and the vertical bars indicate the ASEs. The results differ significantly in relation to the control group (C), $P<0.01$. None of the extracts administered orally were capable of significantly altering the latency of the animals in the hot plate test compared to morphine, the pharmaceutical of choice for the positive control, as can be seen in FIG. 10**.

Anti-Inflammatory Effects of the Extracts of *Aleurites moluccana* Using the Paw Edema Model Induced by Phlogistic Agents.

Figure 11:
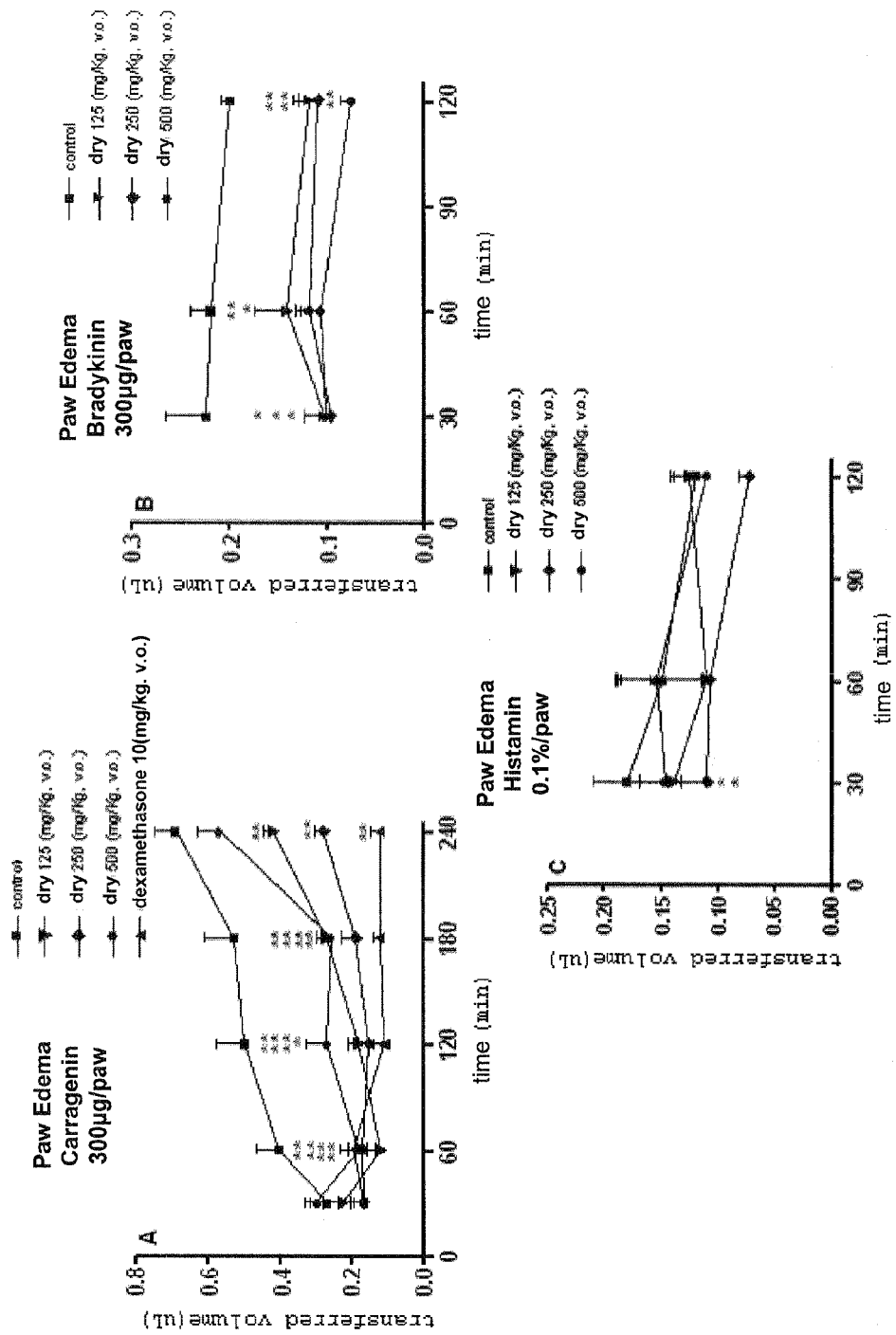
FIG. 11 shows the effects of the dry extract of *Aleurites moluccana* (125 to 500 mg/kg) and of dexamethazone, administered orally, with the paw edema model, being induced in (A) by carragenin, in (B) by bradykinin and in (C) by histamine.

As shown by FIG. 11 (A and B), the oral administration of the dry extract of *Aleurites moluccana* (125 to 500 mg/kg) is capable of significantly reducing paw edema induced by carragenine and bradycinin. However, the same extract is only capable of significantly reducing paw edema induced by histamine at one point (30 min) (FIG. 11 C).

Anti-Inflammatory Effects of the Dried Extract of *Aleurites moluccana* Using the Pleurisy Model Induced by the Intrapleural Injection of Phlogistic Agents.

Figure 12:
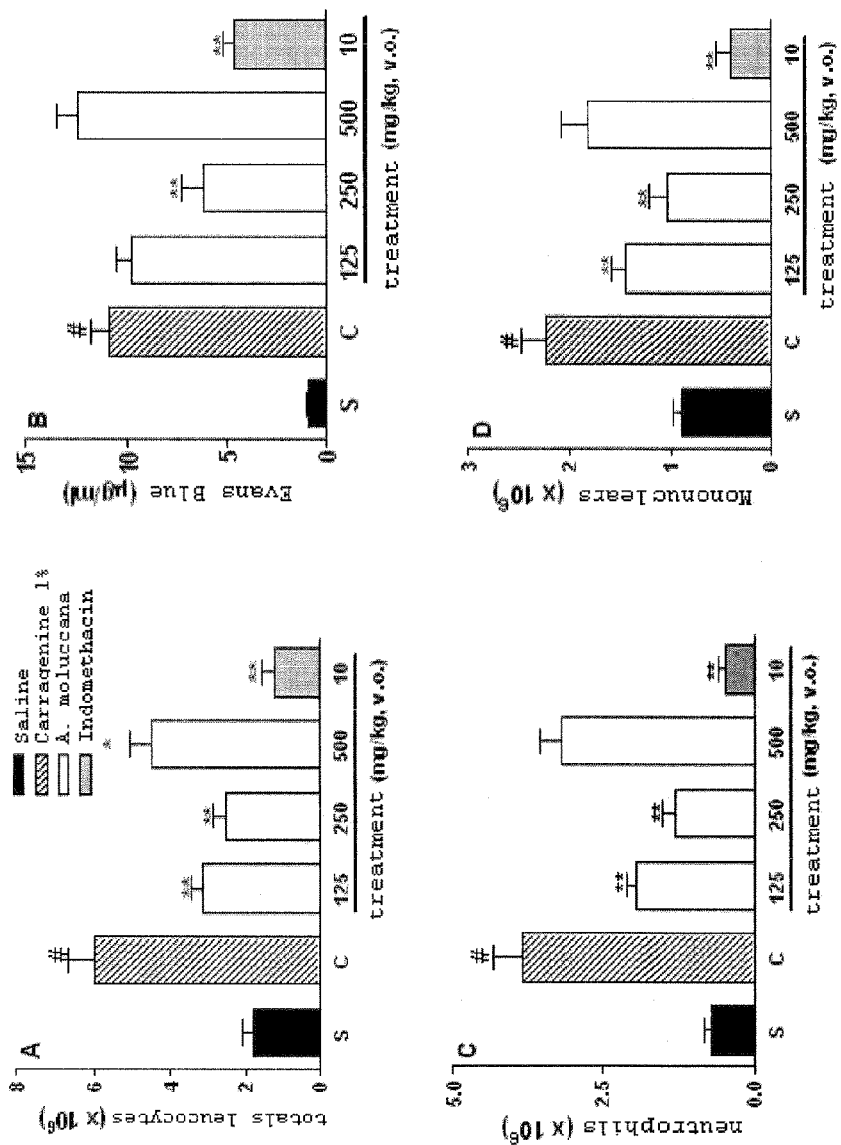
FIG. 12 shows the results obtained from the dry extract of *Aleurites moluccana* (125 to 500 mg/kg) and with Indomethacin (10 mg/kg), administered orally, with the carragenine induced pleurisy model in mice, using total leukocytes in (A); with exudation in (B); neutrophils in (C); and mononuclear cells in (D).

FIG. 12 represents the results obtained with the dry extract of *Aleurites moluccana* (125 a 500 mg/kg), and with Indomethacin (10 mg/kg), administered orally, in the pleurisy induced by carragenine model in mice. Each point represents an average of 8 to 10 animals and the vertical bars indicate the ASEs. The results differ significantly in relation to the control group (C), *$P<0.05$ and $P<0.01$. # represents the difference between the control group and the saline solution group. The total leukocytes are in (A); with exudation being in (B); neutrophils being in (C); and mononuclear cells being in (D). As can be seen in FIG. 12**, the pre-treatment with the dry extract of *Aleurites moluccana*, administered orally, in doses of 125-500 mg/kg, is capable of inhibiting exudation as well as the migration of inflammatory cells, represented by the count of total leukocytes, mononuclear cells and neutrophils, in the pleurisy induced by carragenine model in mice. However, the same is only capable of acting on the plasmatic outflow and on the migration of mononuclear cells in the pleurisy induced by substance P model (see FIGS. 13 A to D).

Figure 13:
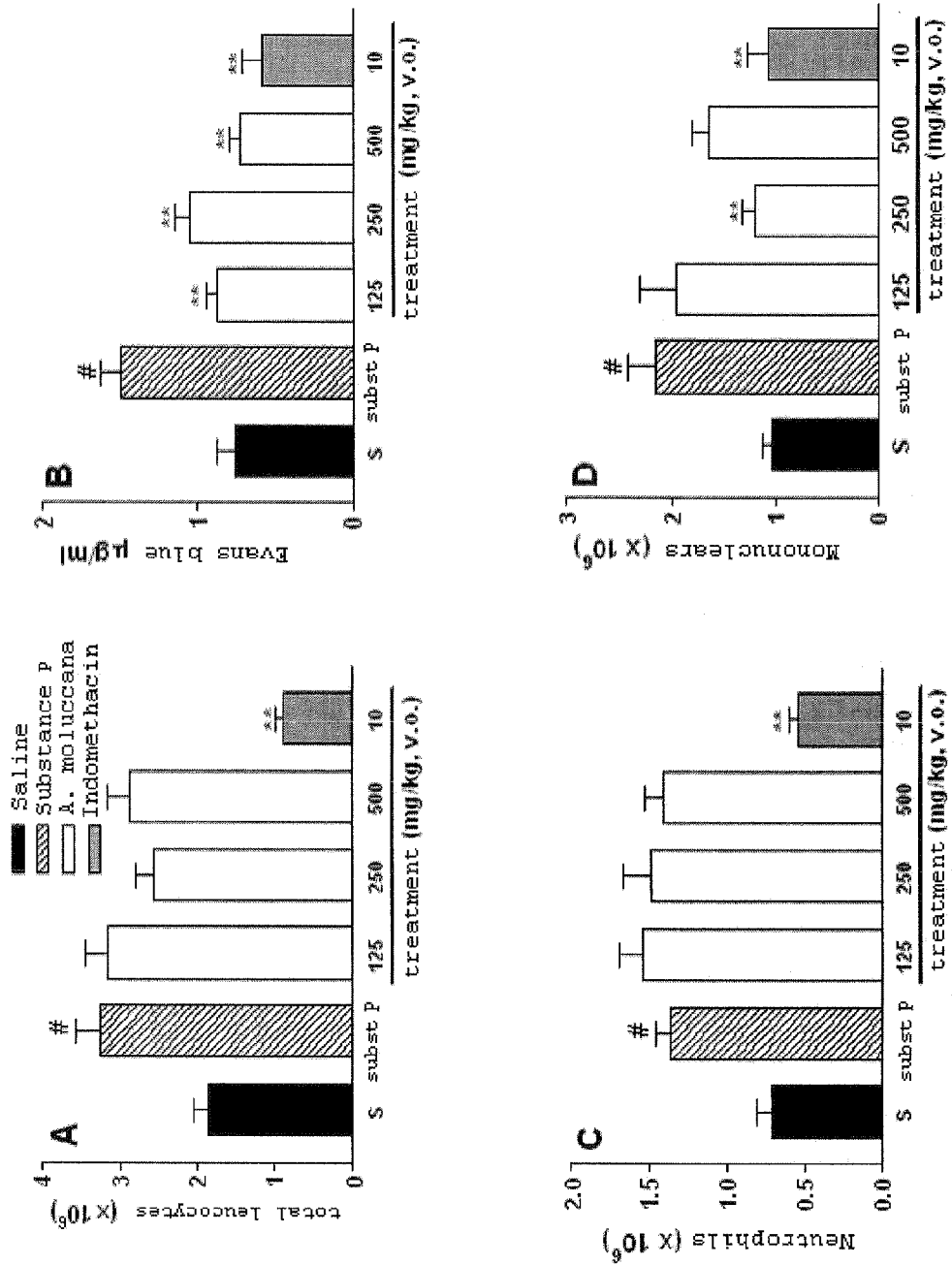
FIG. 13 shows the results obtained from the dry extract of *Aleurites moluccana* (125 to 500 mg/kg) and with Indomethacin (10 mg/kg), administered orally, with the substance P induced pleurisy model in mice, using total leukocytes in (A); with exudation in (B); neutrophils in (C); and mononuclear cells in (D).

FIG. 13 shows the results obtained with the dry extract of *Aleurites moluccana* (125 a 500 mg/kg), and with Indomethacin (10 mg/kg), administered orally, in the pleurisy induced by substance P model in mice. Each point represents an average of 8 to 10 animals and the vertical bars indicate the ASEs. The results differ significantly in relation to the control group (C), *P<0.05 and **P<0.01. # represents the difference between the control group and the saline solution group. The experiment was conducted with total leukocytes (FIG. 13(A)); by exudation (FIG. 13 (B)); with neutrophils (FIG. 13(C)); and with mononuclear cells (FIG. 13(D)).

Figure 14:
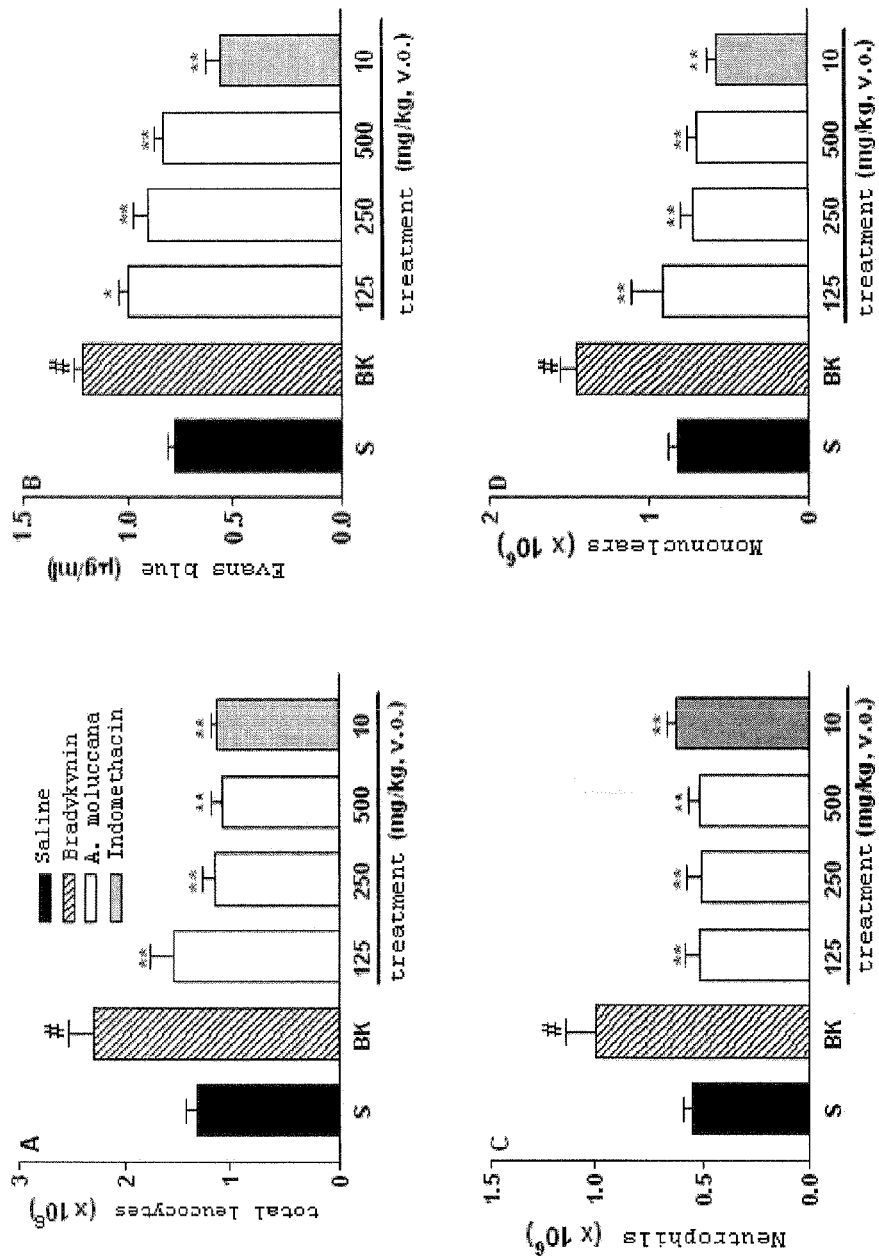
FIG. 14 shows the results obtained from the dry extract of *Aleurites moluccana* (125 to 500 mg/kg) and with Indomethacin (10 mg/kg), administered orally, with the bradicinine induced pleurisy model in mice, using total leukocytes in (A); with exudation in (B); neutrophils in (C); and mononuclear cells in (D).
Figure 15:
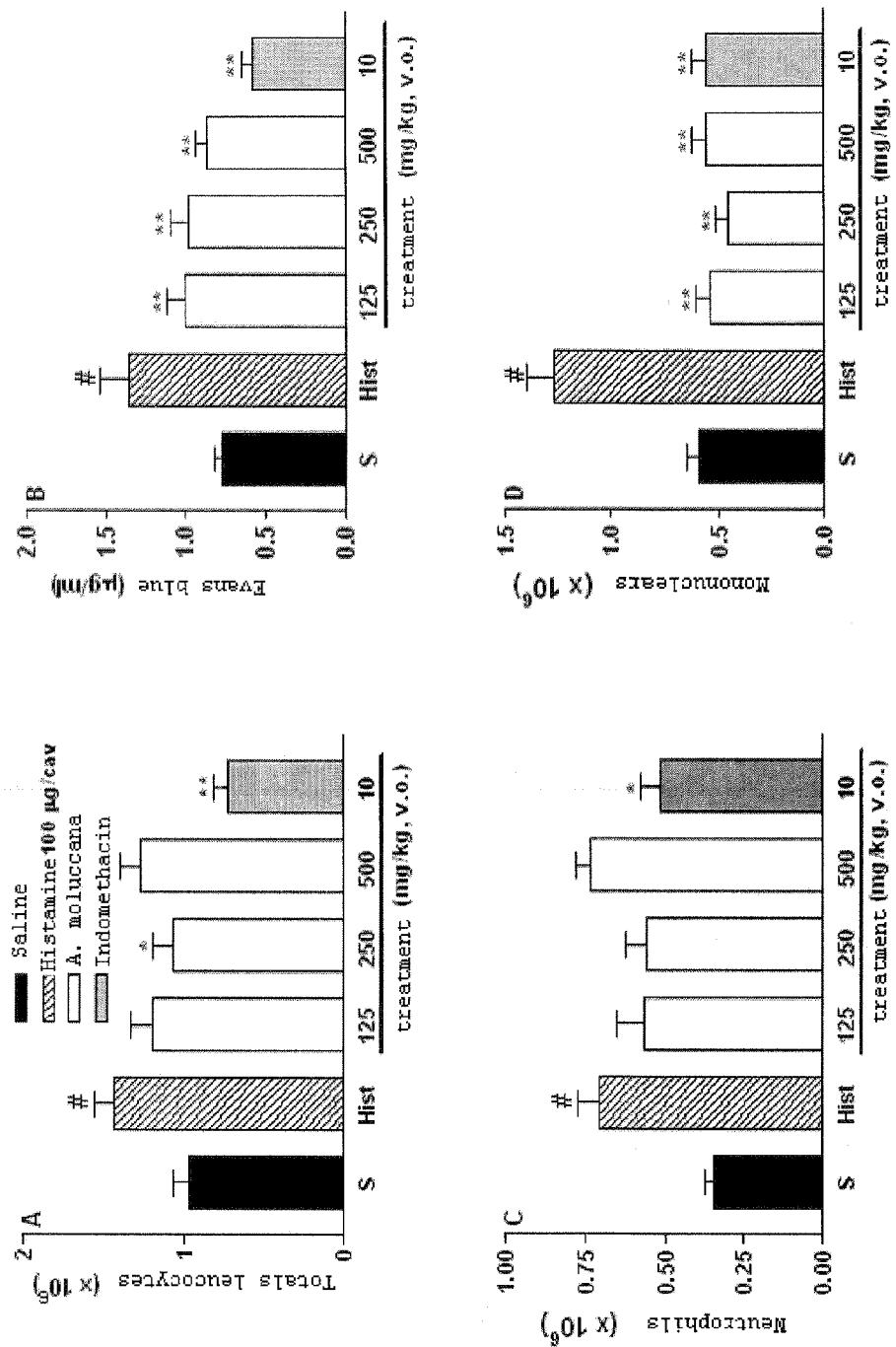
FIG. 15 shows the results obtained from the dry extract of *Aleurites moluccana* (125 to 500 mg/kg) and with Indomethacin (10 mg/kg), administered orally, with the histamine induced pleurisy model in mice, using total leukocytes in (A); with exudation in (B); neutrophils in (C); and mononuclear cells in (D).

FIG. 14 represents the results obtained with the dry extract of *Aleurites moluccana* (125 a 500 mg/kg), and with Indomethacin (10 mg/kg), administered orally, in the pleurisy induced by bradykynin model in mice. Each point represents an average of 8 to 10 animals and the vertical bars indicate the ASEs. The results differ significantly in relation to the control group (C), *P<0.05 and **P<0.01. # represents the difference between the control group and the saline solution group. The total leukocytes are in (A); with exudation being in (B); neutrophils being in (C); and mononuclear cells being in (D). As can be seen in FIG. 14, the pre-treatment with the dry extract of *Aleurites moluccana*, administered orally, in doses of 125-500 mg/kg, is capable of inhibiting exudation as well as the migration of inflammatory cells, represented by the count of total leukocytes, mononuclear cells and neutrophils in the pleurisy induced by bradykynin model in mice. However, the same is only capable of acting on the plasmatic outflow (in a dose dependant manner) and the migration of mononuclear cells in the pleurisy induced by histamine model (see FIGS. 13 B to D). FIG. 15 shows the results obtained with the dry extract of *Aleurites moluccana* (125 a 500 mg/kg), and with Indomethacin (10 mg/kg), administered orally, in the pleurisy induced by histamine model in mice. Each point represents an average of 8 to 10 animals and the vertical bars indicate the ASEs. The results differ significantly in relation to the control group (C), *P<0.05 and **P<0.01. # represents the difference between the control group and the saline solution group. The experiment was conducted with total leukocytes (FIG. 15(A)); by exudation (FIG. 15 (B)); with neutrophils (FIG. 15(C)); and with mononuclear cells (FIG. 15(D)).

Antiedematogenic Effects of the Dried Extract of *Aleurites moluccana* Using the Edema of the Ear Model Induced by Croton Oil.

Figure 16:
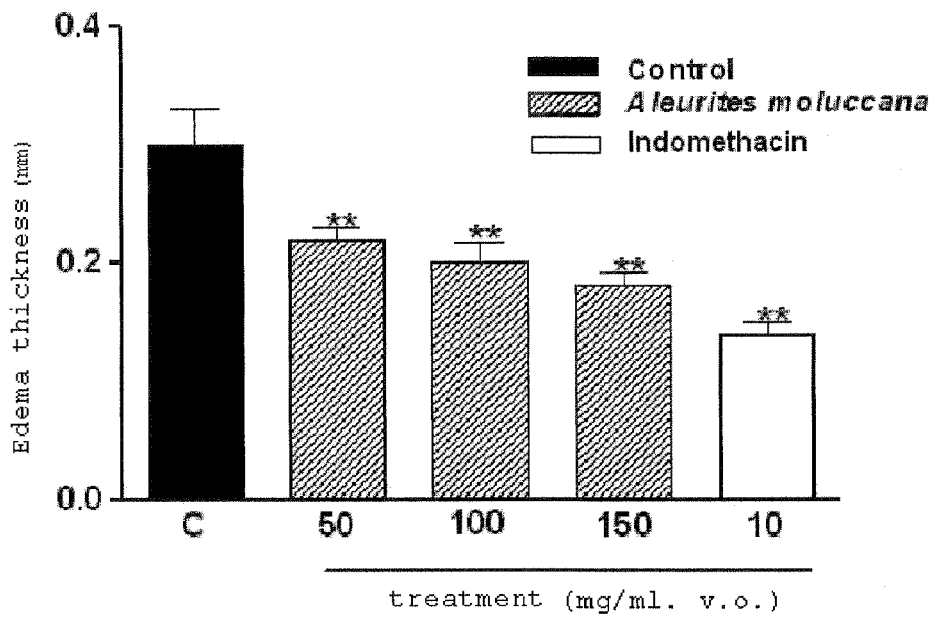
FIG. 16 shows the results obtained from the dry extract of *Aleurites moluccana* (125 to 500 mg/kg) and with Indomethacin (10 mg/kg), administered orally, with the croton oil-induced ear edema model.

FIG. 16 represents the results obtained with the dry extract of *Aleurites moluccana* (125 a 500 mg/kg), and with Indomethacin (10 mg/kg), administered orally, in the edema of the ear induced by croton oil model. Each point represents an average of 8 to 10 animals and the vertical bars indicate the ASEs. The results differ significantly in relation to the control group (black bar), *P<0.05 and **P<0.01. FIG. 16 demonstrates that the oral administration of the dry extract is efficient in reducing the edema of the ear induced by croton oil with an IM calculated at 43.75±2.47%.

Antipyretic Effects of the Extracts of *Aleurites moluccana* Using the Hyperthermia Model Induced by LPS in Rats.

Figure 17:
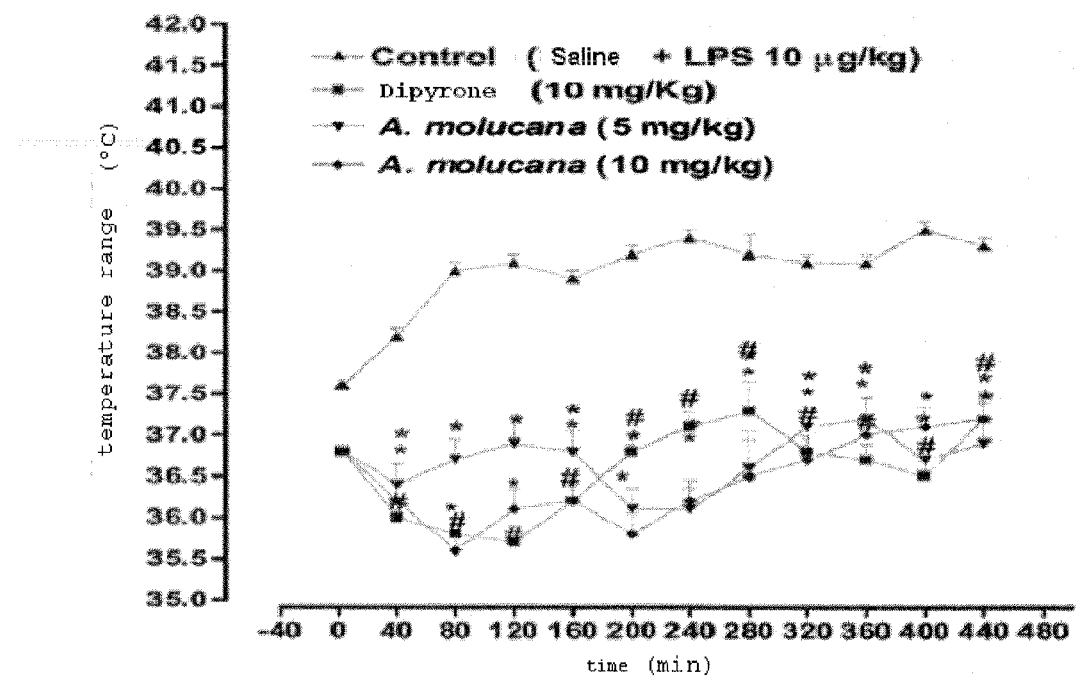
FIG. 17 shows the results obtained from the dry extract of *Aleurites moluccana* (5 to 10 mg/kg) and Dipyrone (10 mg/kg), administered orally, with the LPS induced hyperthermia model.

FIG. 17 shows the results obtained with the dry extract of *Aleurites moluccana* (5 a 10 mg/kg), and Dipyrone (10 mg/kg), administered orally, in the hyperthermia induced by LPS model. Each point represents an average of 8 to 10 animals and the vertical bars indicate the ASEs. The results differ significantly in relation to the control group, *P<0.05. # represents the difference between the control group and the saline solution group. FIG. 17 demonstrates that the oral administration of the dry extract promotes a reduction of the febrile response in the animals in a statistically significant manner when compared to the controls (Dipyrone, vehicle) and does not produce alterations to the gastric mucosa, normally present in antipyretic agents.

Effects of the Extracts of *Aleurites moluccana* in Inducing Lesions to the Gastric Mucosa in Rats.

Figure 18:
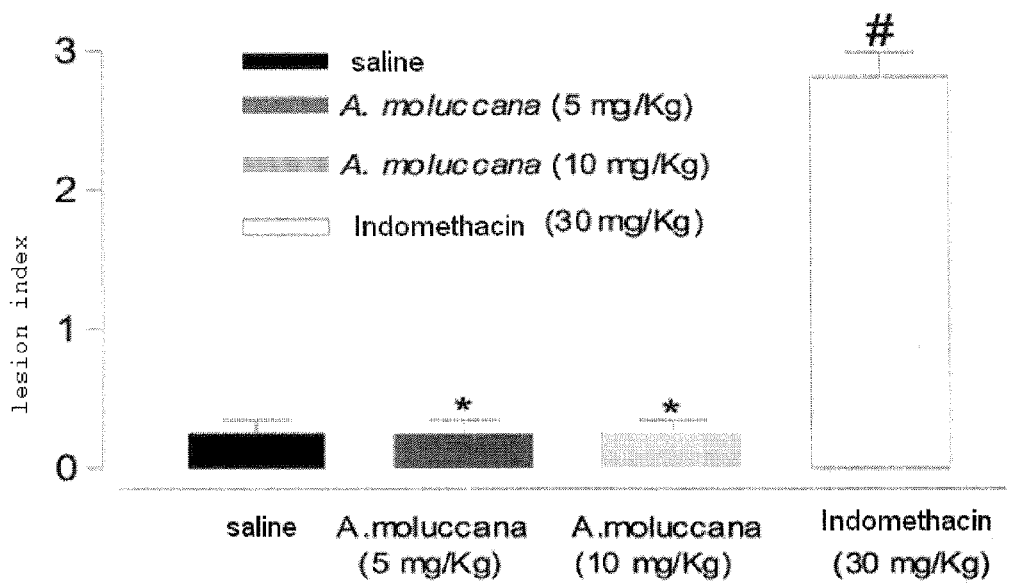
FIG. 18 shows the results obtained from the soft extract of *Aleurites moluccana* (5 to 10 mg/kg) and Indomethacin (10 mg/kg), administered orally, for verification of occurrence of a lesion to the gastric mucosa.

FIG. 18 shows the results obtained with the soft extract of *Aleurites moluccana* (5 a 10 mg/kg), and Indomethacin (10 mg/kg), administered orally, for verification of lesions to the gastric mucosa. Each point represents an average of 8 to 10 animals and the vertical bars indicate the ASEs. The results differ significantly in relation to the control group, *P<0.05. # represents the difference between the control group and the saline solution group. FIG. 18 demonstrates that the oral administration of the soft extract does not produce alterations to the gastric mucosa, normally present in antipyretic agents.

Effects of the Dry Extract of *Aleurites moluccana* on Mechanical Hypernociception Induced by the Intraplantar Injection of Carragenin.

Figure 19:
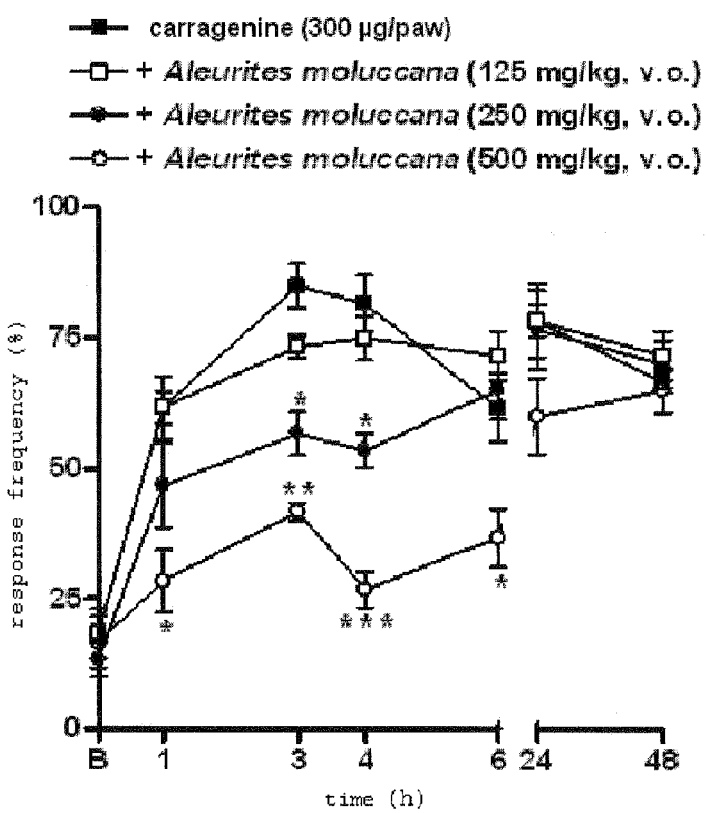
FIG. 19 shows the anti-hypernociceptive effects of the dry extract of *Aleurites moluccana* (125 to 500 mg/kg, administered orally) in the mechanical hypernociception model induced by the intraplantar injection of carragenine (300 µg/paw).

FIG. 19 shows the anti-hypernociceptive effect of the dry extract of *Aleurites moluccana* (125 a 500 mg/kg, v.o.) using the mechanical hypernociception induced by the intraplantar injection of carragenine model (300 μg/paw). Each point represents the average of 6 to 8 animals and the vertical bars indicate the ASEs. The results differ significantly in relation to the control group, *P<0.05, P<0.01 e *<0.001. As can be seen in FIG. 19, the oral treatment with the dry extract of *Aleurites moluccana*, when administered in doses of 125, 250 and 500 mg/kg, is capable of significantly reducing in a dose dependent manner the mechanical hypernociception induced by the injection of carragenin, with a DI50% of 433 (295 to 407) mg/kg. This inhibition is observed for up to 6 hours after the injection with carragenine. The inhibition observed in relation to the control response are stipulated at 33±5% and 51±2%, for the doses of 250 and 500 mg/kg, respectively.

Effects of the Dry Extract of *Aleurites moluccana* on Mechanical Hypernociception Induced by the Intraplantar Injection of Prostaglandin $E_2$ ($PGE_2$).

Figure 20:
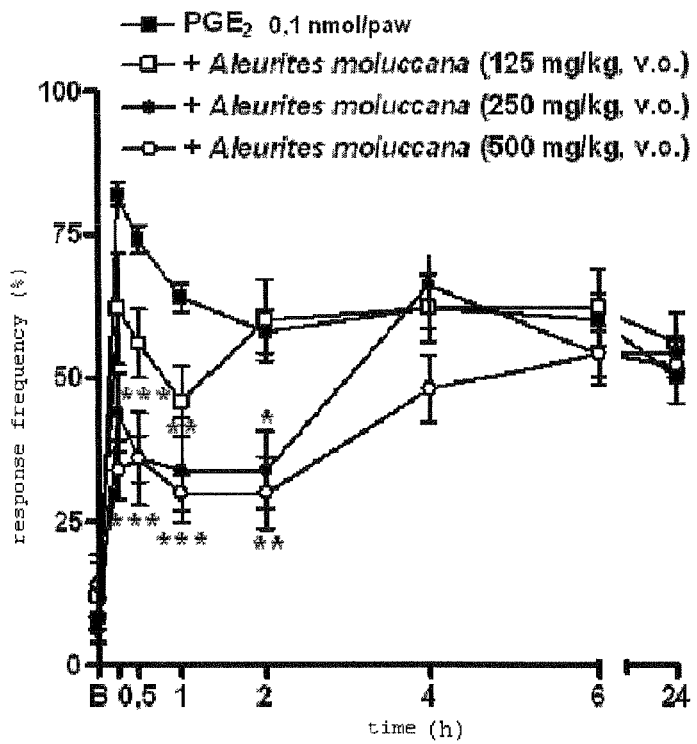
FIG. 20 shows the anti-hypernociceptive effects of the dry extract of *Aleurites moluccana* (125 to 500 mg/kg, administered orally) for the mechanical hypernociception model induced by the intraplantar injection of PGE2 (0.1 nmol/paw).

FIG. 20 shows the anti-hypernociceptive effect of the dry extract of *Aleurites moluccana* (125 a 500 mg/kg, v.o.) using the mechanical hypernociception induced by the intraplantar injection of PGE2 model (0.1 nmol/paw). Each point represents the average of 6 to 8 animals and the vertical bars indicate the ASEs. The results differ significantly in relation to the control group, *P<0.05, P<0.01 e *<0.001. FIG. 20 demonstrates that the oral treatment with the dry extract of *Aleurites moluccana*, (125, 250 and 500 mg/kg) is capable of significantly reducing in a dose dependent manner the mechanical hypernociception response induced by the intraplantar injection of $PGE_2$, (for up to 2 hours after the injection of $PGE_2$), with DI50% equal to 201 (91 to 445) mg/kg. Inhibitions of 8±6%, 11±8% and 63±7% were obtained for the doses of 125, 250 and 500 mg/kg, respectively.

Effects of the Dry Extract of *Aleurites moluccana* on Mechanical Hypernociception Induced by the Intraplantar Injection of the Complete Freund's Adjuvant (CFA).

Figure 21:
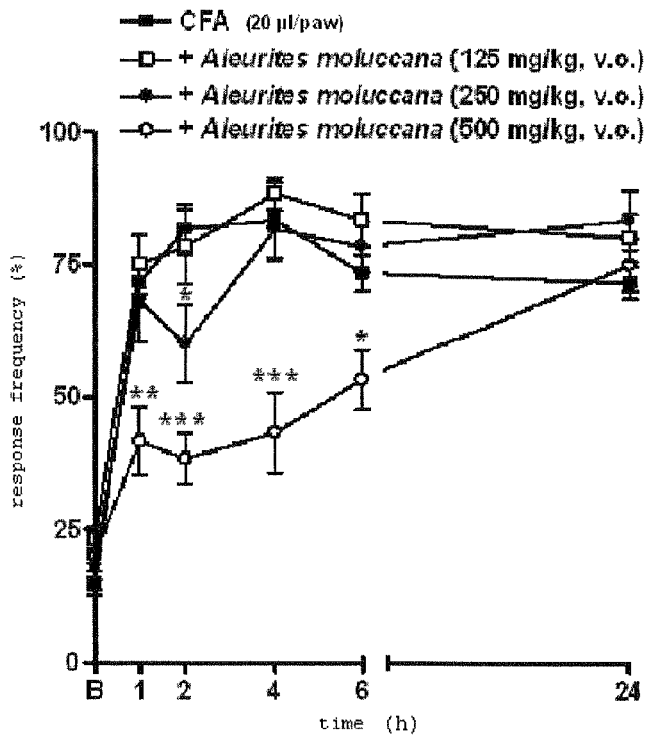
FIG. 21 shows the effect of preventive treatment using the dry extract of *Aleurites moluccana* (125 to 500 mg/kg, administered orally) for mechanical hypernociception induced by the intraplantar injection of CFA (20 µl/paw).

FIG. 21 shows the effect of the preventive treatment with the dry extract of *Aleurites moluccana* (125 a 500 mg/kg, v.o.) on the anti-hypernociceptive effect of using the mechanical hypernociception induced by the intraplantar injection of CFA model (20 μl/paw). Each point represents the average of 6 to 8 animals and the vertical bars indicate the ASEs. The results differ significantly in relation to the control group, *P<0.05, P<0.01 e *<0.001. FIG. 21 demonstrates that preventive oral administration with the dry extract of *Aleurites moluccana* (125, 250 e 500 mg/kg) is capable of significantly reducing the mechanical hypernociception induced by the intraplantar injection of CFA, for up to 6 hours after the inducement of hypernociception, with DI50% of 275 (239 to 316) mg/kg and inhibitions of 29±6% and 53±6% for the doses of 250 and 500 mg/kg, respectively.

For assessment of the effect of the dry extract of *Aleurites moluccana* on an existing condition of mechanical hypernociception, the animals were first administered an intraplantar injection of CFA, and after 24 h were treated with the extract in doses of 125, 250 and 500 mg/kg, 2 times a day during 5 consecutive days.

Figure 22A:
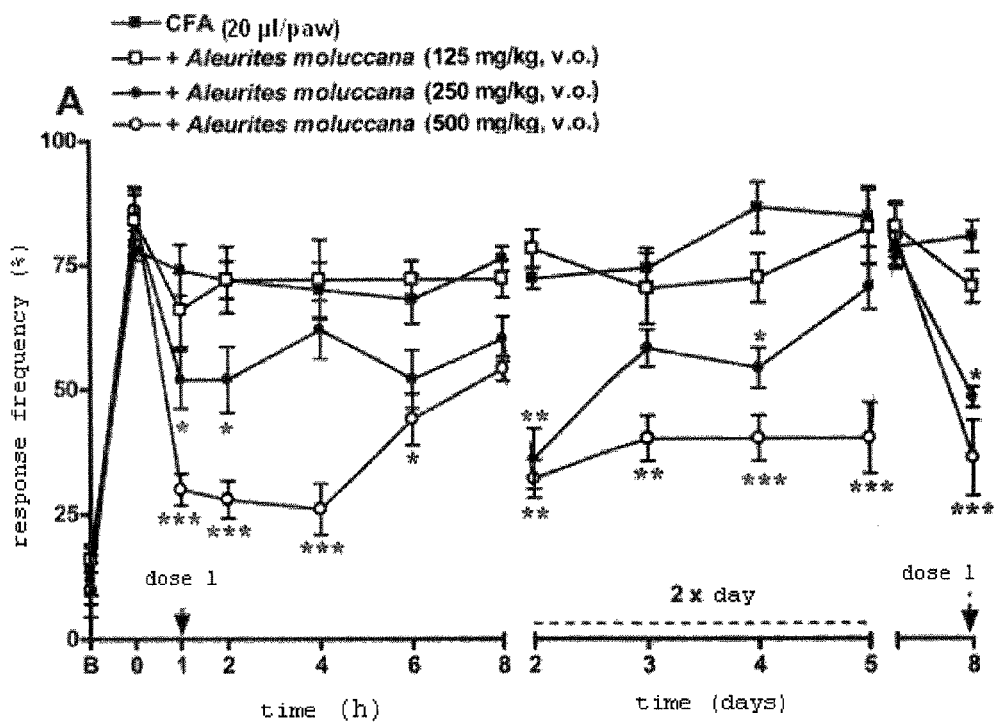
FIG. 22 shows the effect of curative treatment using the dry extract of *Aleurites moluccana* (125 to 500 mg/kg, administered orally) for mechanical hypernociception induced by the intraplantar injection of CFA (20 µl/paw) in the paw ipsilateral in (A) and contralateral in (B) to the injection.
Figure 22B:
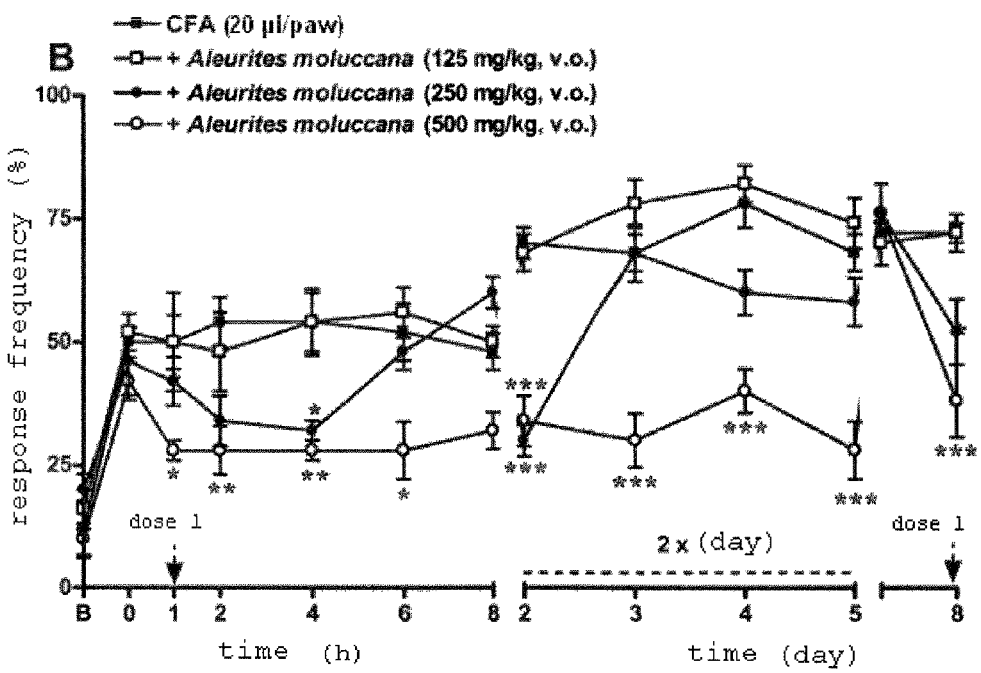

FIG. 22 shows the effect of curative treatment using the dry extract of *Aleurites moluccana* (125 to 500 mg/kg, v.o.) on the mechanical hypernociception induced by the intraplantar injection of CFA (20 μl/paw) in the ipsilateral (FIG. 16(A)) and contralateral (FIG. 16(B)) paw to the injection. Each point represents the average of 6 to 8 animals and the vertical bars indicate the ASEs. The results differ significantly in relation to the control group, *P<0.05, P<0.01 e *<0.001. FIG. 22 demonstrates that administration of the dry extract of *Aleurites moluccana* is capable of reverting an existing condition of mechanical hypernociception (125, 250 e 500 mg/kg) is capable of significantly reducing the mechanical hypernociception induced by the intraplantar injection of CFA, in the paw ipsilateral to the injection in a dose dependant manner, with DI50% of 272 (130 to 568) mg/kg. The inhibitions were of 8±6%, 11±8% e 63±7 for the doses of 125, 250 and 500 mg/kg, respectively (FIG. 22 A). Similarly, the same treatment is capable of preventing the occurrence of mechanical hypernociception in the paw contralateral to the injected paw, with an inhibition of 56±8% in a dose of 500 mg/kg (FIG. 22 B).

A preferred embodiment of the tests for the pharmacological characterisation of the antinociceptive, anti-inflammatory and anti-hypernociceptive activities of the standard extracts of *Aleurites moluccana* obtained in accordance with the processes described above are described in greater detail in the Examples V, VI and VII, below.

Toxicological Evaluation of the Soft Extract of *Aleurites moluccana*.

Preliminary studies with mice demonstrated that the oral administration of the soft extract of *Aleurites moluccana* in a dose of 5000 mg/kg (n=10, 5 males and 5 females), did not cause any death in a period of 3 to 24 hours. Furthermore, there were no signs of irritability, tachycardia, tremors or piloerection, as described in Tables 5 and 6.

TABLE 5

Evaluation of the behavioural parameters of male mice treated with the soft extract of *Aleurites moluccana* (5000 mg/Kg) using the hippocratic test.

| Evaluated Parameters | Dose g/kg | 0 to 10 min | 30 min | 60 min | 180 min | 1.440 min |
|---|---|---|---|---|---|---|
| Piloerection | Control | 1/5 | 1/5 | 0/5 | 0/5 | 0/5 |
|  | Treated | 0/5 | 0/5 | 0/5 | 0/5 | 0/5 |
| Cage corner movement | Control | 5/5 | 3/5 | 0/5 | 0/5 | 0/5 |
|  | Treated | 5/5 | 4/5 | 0/5 | 0/5 | 0/5 |
| Tremors | Control | 0/5 | 0/5 | 0/5 | 0/5 | 0/5 |
|  | Treated | 0/5 | 0/5 | 0/5 | 0/5 | 0/5 |
| Tachycardia | Control | 0/5 | 0/5 | 0/5 | 0/5 | 0/5 |
|  | Treated | 1/5 | 0/5 | 0/5 | 0/5 | 0/5 |
| Irritability | Control | 3/5 | 3/5 | 3/5 | 0/5 | 0/5 |
|  | Treated | 1/5 | 1/5 | 0/5 | 0/5 | 0/5 |
| Miction | Control | 5/5 | 5/5 | 5/5 | 0/5 | 0/5 |
|  | Treated | 1/5 | 1/5 | 2/5 | 2/5 | 0/5 |
| Defecation | Treated | 5/5 | 5/5 | 0/5 | 0/5 | 0/5 |
|  | Control | 4/5 | 2/5 | 0/5 | 0/5 | 0/5 |
| Ptosis | Control | 5/5 | 5/5 | 0/5 | 0/5 | 0/5 |
|  | Treated | 1/5 | 1/5 | 1/5 | 0/5 | 0/5 |

TABLE 5-continued

Evaluation of the behavioural parameters of male mice treated with the soft extract of *Aleurites moluccana* (5000 mg/Kg) using the hippocratic test.

| Evaluated Parameters | Dose g/kg | 0 to 10 min | 30 min | 60 min | 180 min | 1.440 min |
|---|---|---|---|---|---|---|
| Convulsion | Control | 0/0 | 0/0 | 0/0 | 0/0 | 0/0 |
|  | Treated | 0/0 | 0/0 | 0/0 | 0/0 | 0/0 |
| Deaths | Control | 0/0 | 0/0 | 0/0 | 0/0 | 0/0 |
|  | Treated | 0/0 | 0/0 | 0/0 | 0/0 | 0/0 |
| Ptosis | Control | 5/5 | 3/5 | 0/5 | 0/5 | 0/5 |
|  | Treated | 3/5 | 1/5 | 0/5 | 0/5 | 0/5 |
| Convulsion | Control | 0/0 | 0/0 | 0/0 | 0/0 | 0/0 |
|  | Treated | 0/0 | 0/0 | 0/0 | 0/0 | 0/0 |
| Deaths | Control | 0/0 | 0/0 | 0/0 | 0/0 | 0/0 |
|  | Treated | 0/0 | 0/0 | 0/0 | 0/0 | 0/0 |

TABLE 6

Evaluation of the behavioural parameters of female mice treated with the soft extract of *Aleurites moluccana* (5000 mg/Kg) using the hippocratic test.

| Evaluated Parameters | Dose g/kg | 0 to 10 min | 30 min | 60 min | 180 min | 1.440 min |
|---|---|---|---|---|---|---|
| Piloerection | Control | 3/5 | 2/5 | 0/5 | 0/5 | 0/5 |
|  | Treated | 0/5 | 0/5 | 0/5 | 0/5 | 0/5 |
| Cage corner movement | Control | 5/5 | 5/5 | 3/5 | 1/5 | 0/5 |
|  | Treated | 5/5 | 4/5 | 0/5 | 0/5 | 0/5 |
| Tremors | Control | 3/5 | 3/5 | 0/5 | 0/5 | 0/5 |
|  | Treated | 2/5 | 1/5 | 0/5 | 0/5 | 0/5 |
| Tachycardia | Control | 0/5 | 0/5 | 0/5 | 0/5 | 0/5 |
|  | Treated | 0/5 | 0/5 | 0/5 | 0/5 | 0/5 |
| Irritability | Control | 5/5 | 3/5 | 1/5 | 0/5 | 0/5 |
|  | Treated | 5/5 | 3/5 | 1/5 | 0/5 | 0/5 |
| Miction | Control | 5/5 | 3/5 | 1/5 | 1/5 | 1/5 |
|  | Treated | 5/5 | 4/5 | 0/5 | 0/5 | 0/5 |
| Defecation | Control | 5/5 | 3/5 | 2/5 | 1/5 | 0/5 |
|  | Treated | 5/5 | 4/5 | 1/5 | 0/5 | 0/5 |
| Deaths | Control | 0/0 | 0/0 | 0/0 | 0/0 | 0/0 |
|  | Treated | 0/0 | 0/0 | 0/0 | 0/0 | 0/0 |

A preferred embodiment of the tests for the pharmacological characterisation of the toxicological evaluation of the standard extracts of *Aleurites moluccana* obtained in accordance with the processes described above are described in greater detail in Example VIII, below.

Pharmaceutical Compositions

An extract of *Aleurites moluccana* obtained and characterised in accordance with the above description may be administered singly, but shall generally be administered in combination with one or more pharmaceutical vehicles or adjuvants, selected according to the route of administration and Galenic practices.

Pharmaceutical compositions having antinociceptive, anti-inflammatory and antipyretic properties, for use in mammals, comprising an active ingredient of an efficient dose of at least one standard extract, obtained and characterised in accordance with the processes described above, in combination with one or more pharmaceutical vehicles or adjuvants, also constitute aspects of the present invention.

More particularly, the object of the present invention is to provide a pharmaceutical composition incorporating at least one extract of *Aleurites moluccana* comprising the compounds alpha-amyrin, beta-amyrin, alpha-amirinon, beta-amirinon, stigmasterol, beta-sitosterol, campesterol, swertisin and standardised in relation to its 2"-O-rhamnosylswertisin marker having a ratio of 0.015 to 15%.

The pharmaceutical compound in accordance with the present invention may contain a standard extract as defined above, in a quantity representing between 5 and 90% of the total weight of the composition, but preferentially in a quantity representing between 20 and 80% of the total weight of the composition.

The pharmaceutical compound in accordance with the present invention may contain a standard extract as defined above, in a concentration of between 0.01 to 2000 mg per posological unit, but preferentially, in a concentration of 50 to 1000 mg per posological unit.

The standard extracts and compositions of the present invention may be administered orally, by means of oral pharmaceutical forms, such as tablets, capsules (hard or soft), tablets, powders, granules, simple pills, coated pills, chewable pills, effervescent pills, sublingual pills, controlled release pills, dragees, globules, elixirs, suspensions, syrups and emulsions, each of which may include formulatiuons for immediate, controlled, prolonged or delayed release.

The compositions containing the extract of the invention may also be administered via topical route, by means of pharmaceutical forms, such as ointments, unguents, creams, emulsions, gels, solutions, pastes, aerosols, transdermal systems and others known in the state of the art.

Intravenous (either bolus or infusion), subcutaneous or intramuscular administration is also possible, by means of pharmaceutical forms known in the state of the art.

Administration may also be intravaginal and rectal by means of the pharmaceutical forms: suppositories, ovules, ointments, creams and others known in the state of the art.

In accordance with the present invention, the solid pharmaceutical composition intended for oral administration should preferably be in the form of capsule or pill, containing at least one standard extract of *Aleurites moluccana*, which may be combined to one or more pharmaceutically acceptable inert vehicles, such as diluents, lubricants, anti-adherents, sliding agents, agglutinant agents, disaggregating agents, as well as conservatives, colourants, sweeteners, filmogen agents for coatings, plasticisers, opacifiers and the similar, as necessary. The quantities of these pharmaceutical vehicles or adjuvants may be equal to those conventionally used in the state of the art.

Examples of diluents include, but are not limited to starch, monohydrate lactose, spray-dried lactose, microcrystalline cellulose, dicalcium phosphate, mannitol, powdered cellulose and the similar.

Examples of lubricants and sliding agents include, but are not limited to: stearic acid, oxide of silicon, magnesium stearate, calcium stearate, talcum, stearile sodium fumarate, glyceryl triestearate, polyethylene glycol and the similar.

Examples of agglutinants include, but are not limited to pregelatinised starch, hydroxypropylcellulose, methylcellulose, sodium carboxymethylcellulose, hydroxypropylmethylcellulose, polyvinylpyrrolidone, starch, gelatine, natural sugars such as glucose, syrups, natural and synthetic gums, acacia, sodium alginate, polyethylene glycol, waxes and the similar.

Examples of desaggregating agents include, but are not limited to carboxymethylcellulose, reticulated sodium, sodic carboxymethylcellulose with a low substitution rate, sodic croscarmelose, sodium starch glycolate, cross linked polyvinylpyrrolidone and the similar.

Examples of sliding agents include, but are not limited to: colloidal silicon dioxide, hydrophobic colloidal silicon dioxide and the similar.

Examples of conservatives include, but are not limited to ascorbic acid, peroxy benzoic acid esters, chlorobutanol, benzylic alcohol, phenethyl alcohol, dehydroacetic alcohol and the similar.

Preferred examples of colorants include, but are not limited to hydro-unsoluble lacquer pigments, natural pigments, such as $\beta$-carotene and chlorophyll, iron oxide, yellow iron sesquioxide, black iron sesquioxide and the similar.

Examples of sweeteners include, but are not limited to: dextrose, mannitol, sorbitol, saccharose, glycerine, sodic saccharin, dipotassium glycyrrhizinate, aspartame, stevia and the similar.

Examples of film coating polymers include, but are not limited to hydroxypropylmethylcellulose (e.g. Opadry®), hydroxypropylcellulose, cellulose acetophthalate and derivatives of methacrylic and methacrylate acid (e.g. Eudragit®) and the similar.

Examples of plasticisers and opacifiers include, but are not limited to glycerine fatty acid esters, triethyl citrate, propyleneglycol, polyethylene glycol, titanium dioxide and the similar.

The preferred embodiments of the present invention for obtaining a pill and a capsule are described below in greater detail in Example IX and Example X, respectively.

Pharmaceutical compositions intended for oral administration in accordance with the present invention also include solutions, syrups, elixirs and suspensions that may contain, but are not limited to solubilizers, solvents, co-solvents, dissolution adjuvants, humidifier agents, suspension agents, conservatives, stabilisers, alkalisers, acidifiers, viscosity modification agents, sweeteners and flavourisers. Overall, water, ethylic alcohol, appropriate oils, saline solution, aqueous dextrose (glucose), saccharose, glycerine, sugar related solutions and glycols, such as propylenoglycol or polyethylene glycols, phosphate buffer, cyclodextrins, agar, bentonite, carbomer, methylcellulose and hydroxypropylmethylcellulose are appropriate vehicles for liquid pharmaceutical forms.

The preferred embodiments of the present invention for obtaining a suspension or a syrup are described below in greater detail in Example XI and Example XII, respectively.

Pharmaceutical compositions in accordance with the present invention may be pharmaceutical forms that propitiate modified, controlled, sustained, extended, prolonged, programmed, slow, delayed, enteric, colon-specific or site-specific release of the active ingredient. Examples of pharmaceutical forms with these features include, but are not limited to osmotic pump systems, matricial systems, reservoir systems, ionic exchange systems, enteric coating forms, pH-dependant coating forms, transdermal systems, pulsing devices, implants, liposomal systems, nano-structured systems, microstructures systems and the similar.

Pharmaceutical compositions in accordance with the present invention may be obtained by industrial pharmaceutical processes and unitary operations known in the state of the art, such as, but not limited to mixing, grinding, sieving, shredding, micronisation, lubrication, classification, wetting, drying, dry granulation, humid granulation, compression, encapsulation, coating, dissolution and homogenisation, or a combination of these.

Preferentially, in accordance with the present invention, a pharmaceutical composition intended for topical administration also include, but are not limited to emulsions, creams or ointments, may contain one or more pharmaceutically acceptable inert vehicles or adjuvants. These adjuvants may be components of the aqueous phase, components of the oleous phase, emollients, humidifiers, emulsifiers, tensoactives, conservatives, stabilisers, antioxidants, chelating agents, self-emulsifying waxes, bases for ointments, colorants, essences and the similar, when necessary. The quantities of these pharmaceutical vehicles or adjuvants may be equal to those commonly used in the state of the art.

Examples of components of the oleous phase, consistency agents, emulsifiers and self-emulsifying waxes include, but are not limited to stearic acid, cetyl alcohol, stearyl alcohol, cetostearyl alcohol, cetostearyl alcohol 20oe (20 moles of ethylene oxide), glyceryl monostearate, propylenoglycol monostearate, sorbitan monostearate, microcrystalline wax, anionic self-emulsifying wax (for example, Lanete), non-ionic self-emulsifying wax (for example, Cosmowax®), non-ionic self-emulsifying wax (for example, Polawax®), non-ionic self-emulsifying wax (for example, Crodabase®) and the similar.

Examples of emollients include, but are not limited to isopropyl myristolate, mineral oil, myristyl alcohol, cetyl palmitate, octyl palmitate, myristyl myristate, glyceryl stearate, polyoxyethylene stearate, coconut's hydrogenated glycerids, lanolin, lanolin alcohols, decyl oleate, other esters and fatty acids and the similar.

Examples of components of the aqueous phase, consistency agents, humidifiers and polymers include, but are not limited to carbomer (for example, Carbopol®), hydroxyethylcellulose (for example, Natrozol® and Cellosize®), polyacrylic acid (for example, Pemulem®), propylenoglycol, sorbitol, glycerin, dimethicone, urea and the similar.

Examples of tensoactives include, but are not limited to tween 20, tween 80, triethanolamin, polysorbate 80, octoxinol, sorbithane monopalmitate, sodium lauryl sulphate and the similar.

Examples of bases for ointments include, but are not limited to lanolin, vaseline, hydrophilic petrolate, yellow ointment, white ointment, hydrophilic ointment, polyethylene glycol ointment and the similar.

Examples of conservatives, stabilisers, antioxidants and chelating agents include, but are not limited to methylparaben (for example, Nipagin®), propylparaben (for example, Nipazol®), butylparaben, timerosal, benzalconic chloride, benzetonium chloride, phenoxyethanol, phenoxyethanol+parabenes (for example, Phenonip®), diazolidinyl urea (for example, Germall®), diazolidinyl urea+iodopropynyl butylcarbamate (Germall Plus®), edetic acid, disodic EDTA, ascorbic acid, sodium bisulphite, sodium metabisulphite and the similar.

With the purpose of complementing the therapeutic activity presented herein, the pharmaceutical compositions including at least one extract in accordance with the present invention may combine, furthermore, other pharmacologically active compounds such as synthetic and semi-synthetic substances, biological molecules (e.g. proteins) vitamins and other derivatives of plant origin, depending on the intended effect.

Method of Treatment

Another aspect of the present invention refers to a method to prevent, control or treat clinical conditions of pain, inflammation and fever, with some of these having been presented above, that comprises the administration, in mammals, of a therapeutically efficient dose of a standardized extract of *Aleurites moluccana*, or a pharmaceutical composition that contains the latter, for an adequate period of time.

The method, in accordance with the present invention, is related to the clinical effects of an efficient dose of a standardized extract of *Aleurites moluccana* on illnesses and symptoms in which the substances having antinociceptive, anti-inflammatory and anti-pyretic activity are particularly useful.

The method, in accordance with the present invention, is particularly useful in the control of painful symptomologies of nociceptive origin, in acute, sub-acute and chronic conditions.

According to one embodiment of the present invention, the dose should correspond to between approximately 0.01 to 100 mg of extract per kilogramme of the patient, preferentially between approximately 0.1 to 50 mg/kg, and more particularly between approximately 0.5 to 20 mg/kg.

The extracts and pharmaceutical compositions, in accordance with the present invention, may be advantageously administered in a single daily dose, or, alternatively, the total daily dose may be divided allowing administration in two, three or more times per day.

In accordance with one embodiment of the present invention, a dose of the extract or pharmaceutical composition may be advantageously administered for a period ranging from 1 day to several months.

For determined treatments, however, administration on alternate days is appropriate, either in a cyclical manner or not.

The dose regimen for the standardized extract or pharmaceutical composition in accordance with the present invention naturally varies in accordance with known factors, such as route of administration, species, age, sex, state of health, medical condition and weight of the patient, the nature and extent of the symptoms, the type of concurrent treatment, the intensity and degree of the illness, the frequency of the treatment, the patient's renal and hepatic functions, and the intended effect. A physician, dentist or veterinarian may determine and prescribe the efficient quantity of the medicine necessary to prevent, control or treat a clinical condition of pain, inflammation or fever.

Uses

One of the aspects of the invention refers to the use of the standardized extract for the preparation of a medicine for the treatment of clinical conditions of pain, inflammation or fever.

The invention also refers to the use of the standardized extract for the preparation of a medicine for the control of painful symptomologies of nociceptive origin, in acute, sub-acute or chronic conditions.

The invention also refers to the use of a pharmaceutical composition for the preparation of a medicine for the treatment of clinical conditions of pain, inflammation or fever.

Lastly, the invention also refers to the use of a pharmaceutical composition containing the standardized extract for the preparation of a medicine for the control of painful symptomologies of nociceptive origin, in acute, sub-acute or chronic conditions.

The following examples are more detailed descriptions of the preferred embodiments of the present invention. The procedures proposed and the data presented constitute representative examples of applications of the present invention and should not be construed as indicating limits to the uses of the product.

EXAMPLE I

Obtaining the Standardized Soft Extract from the Leaves of *Aleurites moluccana*

The leaves of *A. moluccana* are washed, dried, shredded and classified by passing through a sieve, thus providing shredded leaves under 20 mm in size. The plant material is then submitted to extraction with a hydroalcoholic solution of ethanol/water in a proportion of 7:3. The volume used for extraction corresponded to 10 parts of extractor liquid to 1 of plant material. Extraction was performed at room temperature by the maceration method, without agitation. After 5 days, the solution was percolated and filtered through a paper filter. The filtrate was concentrated at a maximum temperature of 70° C., in a specific evaporator (Bernhauer), under vacuum (400 mmHg), until a non-alcoholic soft extract was obtained with a total rate of solids between 20% and 40%.

Obtaining the Dry Extract from the Leaves of *Aleurites moluccana*

The soft extract was obtained as described above. In sequence, a variable quantity ranging from 10 to 40% of drying adjuvant is added to the extract in relation to the rate of solids of the final product. The mixture is dehydrated in a spray-drier using the centrifugal rotative disc, at a pump input speed of 45 Hz, generating an output of 6.5 litres of concentrate/hour, at an input temperature of 160 to 180° C. and output temperature of 90 to 110° C.

EXAMPLE II

Qualitative Analysis of the Standardized Extracts of *Aleurites moluccana*

Qualitative Analysis of the Extracts by TLC

Thin layer chromatography (TLC) was used to analyse the constituents of the extracts of *Aleurites moluccana*, in accordance with the present invention, using alpha-amyrin and beta-amyrin, alpha-amirinone and beta-amirinone, stigmasterol, beta-sitosterol, swertisin and 2"-O-rhamnosylswertisin standards, isolated from the actual plant.

For the identification of the polar compounds, with emphasis on swertisin and 2"-O-rhamnosylswertisinisin, 1 g of the fraction of ethyl acetate obtained from the extract EtOH:$H_2O$ 9:1 of the leaves of *A. moluccana*, solubilised with methanol was weighed. The swertisin and 2"-O-rhamnosylswertisin standards were then also weighed (1 mg each) and solubilised with 0.1 ml of methanol. This was followed by the application of 10 μL of each solution to a silica gel 60 plate (8 cm long by 5.5 cm wide) and after drying, the plate was eluted with AcOEt:Acetone:$H_2O$ (25:8:2). Elution was repeated three times. The plate was analysed in an UV chamber a subsequently revealed with a solution of ferric chloride 3% in EtOH, calculating the retention factor (Rf) of the compounds (Farmacopéia Brasileira, part II. 4. Ed. São Paulo: Atheneu, 1996, 200p).

A comparative of the results revealed the presence of these compounds in both the dry and soft extracts, as demonstrated by FIG. 1 (A).

For the identification of the non-polar compounds, with emphasis on alpha-, beta-amyrin, alpha-, beta-amirinone, stigmasterol, beta-sitosterol, 1 g of the fraction of dichloromethane obtained from the extract EtOH:$H_2O$ 9:1 of the leaves of *A. moluccana*, solubilised with dichloromethane was weighed. The alpha-, beta-amyrin, alpha-, beta-amirinone, stigmasterol, beta-sitosterol, standards were then also weighed (1 mg each) and solubilised with 0.1 ml of dichloromethane. This was followed by the application of 10 of each solution to a silica gel 60 plate and after drying, the plate was eluted with Hexane:AcOEt: (7:3). The plate was analysed in an UV chamber a subsequently revealed with a solution of sulphuric anisaldehyde and heated to 60° C. on a hot plate, calculating the retention factor (Rf) of the compounds (Farmacopéia Brasileira, part II. 4. Ed. São Paulo: Atheneu, 1996, 200p). A comparative of the results revealed the presence of these compounds in both extracts, as demonstrated by FIG. 1 (B).

Qualitative Analysis of the Extracts by Gas Chromatography (GC)

The analysis by gas chromatography was performed by a gas chromatograph equipped with a flame ionisation detector (CG-FID), with a DB1 type (Agilent) column having an internal diameter of 30 m×0.25μ.

Test Solution: Exactly 10 mg of the fraction of dichloromethane obtained from the extract EtOH:$H_2O$ 9:1 solubilised with 0.3 ml of HPLC grade dichloromethane was first weighed. A micro-syringe was then used to inject 1 μL of the dichloromethane fraction.

Reference Solution: A micro-syringe was used to inject 1 μL of α and β-amyrin (commercial reference standards—Sigma) at a concentration of 5 mg/ml.

Chromatography Conditions: Column temperature at 200° C. for 2 min, then rising at a rate of 10° C./min until attaining 290° C. and maintained at this temperature for 40 minutes. Injector and detector temperatures of 260° C. and 290° C., respectively. Split of 30 ml/min, with a septum purge of 10 ml/min. Hydrogen used as the mobile gas at a flow of 1 ml/min.

Figure 23:
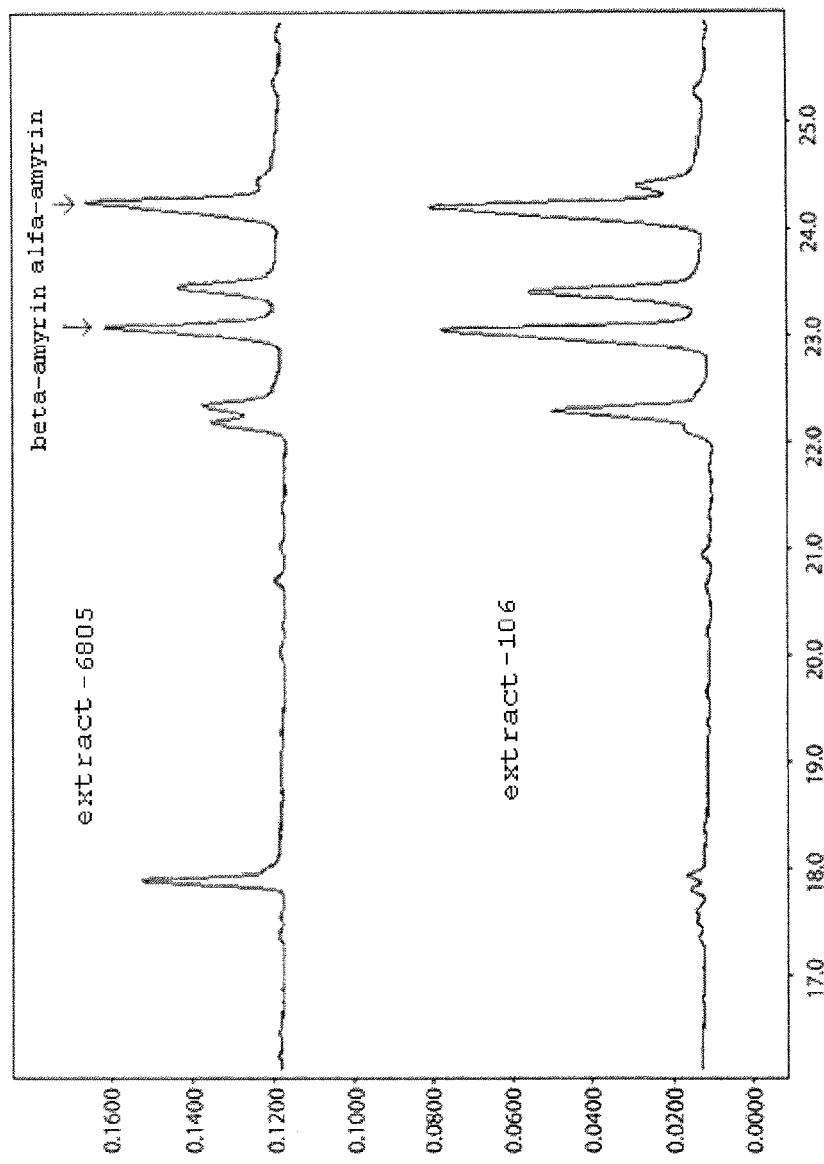
FIG. 23 shows the results obtained with a fraction of dichloromethane of *Aleurites moluccana* assessed by Gas Chromatography (GC).

FIG. 23 shows the results obtained with the fraction of dichloromethane from *Aleurites moluccana* when assessed by Gas Chromatography (GC), using a gas chromatograph equipped with a flame ionisation detector (CG-FID), with a DB1 type (Agilent) column having an internal diameter of 30 m×0.25 mm. The test solution (fraction of dichloromethane from the extract EtOH:$H_2O$=9:1) was solubilised with 0.3 ml of HPLC grade dichloromethane. A micro-syringe was used to inject 1 μL of the fraction of dichloromethane. The reference solution (β-amyrin, Sigma standard) was injected in a concentration of 5 mg/ml, by means of a micro-syringe. The chromatographic conditions were: Column temperature at 200° C. for 2 min, then rising at a rate of 10° C./min until attaining 290° C. and maintained at this temperature for 40 minutes. Injector and detector temperatures of 260° C. and 290° C., respectively. Split of 30 ml/min, with a septum purge of 10 ml/min. Hydrogen used as the mobile gas at a flow of 1 ml/min. As shown by FIG. 23, the chromatogram of the dry and soft extracts revealed the presence of the beta-amyrin standard (5.0 mg/ml) at the retention time of 19.2±0.2 min and alpha-amyrin at the retention time of 20.23±0.2 min.

EXAMPLE III

Quantitative Analysis and Standardisation of the Extracts by HPLC

An analysis by High performance liquid chromatography (HPLC) was performed by dissolving the extracts of *Aleurites moluccana* initially in methanol (20% of final volume), sonicating for 5 min, followed by the addition of water acidified to pH 3.57 (20% of final volume). The volume was then completed with a mixture of methanol/water acidified 50:50 at a concentration of 1 to 2 mg/ml. After filtering the sample through a 0.22 μm membrane filter, 20 μL of the solution was injected using a reversed phase analytical column, where the C18 groups are chemically linked to silica, with a length of 10 to 25 cm and an internal diameter of 4 to 6 mm. A photo diode array (PDA) type detector was used to monitor the chromatogrphic run at between 254 and 338 nm. Separation was performed using a mobile phase linear gradient, initially composed of methanol:water acidified to pH 3.57:acetonitrile (20:15:65) at a flow of 0.5 to 1 ml/min, as described below:

| Time | MeOH | ACN | H$_2$O (pH 3.57) |
|------|------|-----|------------------|
| 0    | 20   | 15  | 65               |
| 10   | 30   | 15  | 55               |
| 20   | 10   | 15  | 75               |
| 25   | 20   | 15  | 65               |

Pressure varied between 2.000 to 3.000 psi.

FIG. 5 (A) shows the HPLC chromatogram of the standard 2"-O-rhamnosylswertisin purified by PTLC (AMSR170707) at 145 µg/ml, in 338 nm, which eluted in approximately 17 min, thus demonstrating success in purification of the marker, as indicated by the presence of a single peak on the chromatogram.

FIG. 5 (B) shows the absorption profile of the 2"-O-rhamnosylswertisin standard, which is typical of flavonoids.

FIG. 2 (A) shows the chromatogram of the dry extract of *Aleurites moluccana* at 2 mg/ml, showing the peak resolution of the 2"-O-rhamnosylswertisin marker (at approximately 17 min) compared to the following peak (swertisin).

Apart from the coincidence in the retention time, the absorption profile at the UV of the peak that eluted in approximately 17 min on the chromatogram of the dry extract (FIG. 5 B) is identical to the 2"-O-rhamnosylswertisin standard.

FIG. 2 (B) shows the chromatogram of the soft extract of *Aleurites moluccana* at 1.72 mg/ml and reveals a very similar profile to that seen for the dry extract (FIG. 23 A), with the presence of a peak relating to 2"-O-rhamnosylswertisin (at approximately 17 min) compared to the following peak (swertisin).

It is therefore possible to confirm and quantify the presence of 2"-O-rhamnosylswertisin in the extracts, observing a variation of 0.05 to 15% of this marker in the extracts.

The method for quantifying 2"-O-rhamnosylswertisin in the extractys is valid, in accordance with the official local regulation (Brazil. National Health Surveillance Agency, (Agência Nacional de Vigilância Sanitária). RE 899, 29th May, 2003).

EXAMPLE IV

Process for the Isolation, Purification and Analysis of the 2"-O-Rhamnosylswertisin Marker from the Extract of *Aleurites moluccana* Using Preparative TLC As the selected marker is not a commercial product, it was isolated and purified from a fraction of ethyl acetate of the hydroalcoholic extract of *A. moluccana*.

Taking the soft extract, as described above, a liquid-liquid partition was performed, initially using dichloromethane and, later, ethyl acetate. A fraction of acetyl previously concentrated until drying in a rota-evaporator at 50° C. was submitted to open column chromatography using a silica gel 60 support, by taking 5 to 20 g of the fraction of the concentrated ethyl acetate prepared in pellet form through mixture with silica gel 60. Chloroform was initially used as the mobile phase with a gradual increase in polarity, using increasing proportions of methanol (from 9:1 to 5:5 of CHCl$_3$:methanol, ending with 100% methanol). The isolation of 2"-O-rhamnosylswertisin was monitored by TLC, as described below (TLC profile of the extracts of *Aleurites moluccana*).

The final purification of the semi purified fractions obtained in accordance with the above methodology was performed by means of Preparative Thin Layer Chromatography (PTLC). The PTLC was performed using a F254 silica gel 60 plate (1 mm thick, Merck), which received a solution of the semi purified fraction dissolved in methanol (10 mg in 0.5 to 1.0 ml) and eluted with a mixture of chloroform:methanol 7:3. The plate was then dried at room temperature before being analysed by UV and the stain corresponding to 2"-O-rhamnosylswertisin (identified by partial plate revelation using ferric chloride 3%) was removed and solubilised with methanol, followed by filtration in paper to finally obtain the marker. The filtrate containing the isolated marker was then dried at room temperature.

The referred standard obtained was then analysed by means of analytic TLC (in accordance with the methodology described in Example II above), HPLC (in accordance with the methodology described in Example III above), infra-red spectrum with a KBr pellet, NMR H$^1$ and NMR C$^{13}$, so as to ascertain purity and establish the standard batch number on a specific form. The results of the analyses performed should be annexed to this form to render the process for obtaining the standard traceable.

The NMR C$^{13}$, NMR H$^1$ and IR spectrums of the marker (batch AMSR170707), mentioned above, are to be found in the FIGS. 3 (A, B, C), 4 (A, B, C) and 6, respectively.

The elution profile by HPLC and the UV absorption profile (batch AMSR170707) are to be found in the FIGS. 5 A and B, respectively.

EXAMPLE V

Tests for Determining the Antinociceptive Activity of the Extract of *A. moluccana* in Acute Nociception Models Assessment of the Antinociceptive Effect of the Extracts of *Aleurites moluccana* Using the Acetic Acid Induced Abdominal Contortion Model.

The experimental acetic acid induced abdominal contortion model allows assessment of the antinociceptive activity of various substances that act both at central and peripheral levels. Nociceptive response is induces by the intraperitonal injection of acetic acid (0.6%) diluted in saline solution (0.9%). The abdominal contortions consist in the contraction of the abdominal muscles combined with the extension of one of the rear paws. The antinociception rate is assessed by the reduction in the number of abdominal contortions compared to the group of animals having received the vehicle (negative control) (Collier, H. D. J. et al., 1968, *Br. J. Pharmacol.*, 32, 295-310).

Each analysis was performed using 8 to 10 male animals (Swiss Webster mice) weighing between 25 and 30 g. The dose was calculated individually for each animal with the quantity in mg/kg (mg/1.000 g) of the substance to be administrated being in accordance to its weight. The injected volume of the solutions followed the rule of 0.1 ml/10 g of the animal's weight.

After treatment with the compounds and the injection of acetic acid, the animals were placed under glass domes and observed individually, with the number of abdominal contortions being cumulatively quantified during a period of 20 minutes. The results were quantified according to the arithmetical average of the number of contortions observed in the animals (all the animals of a specific treatment) followed by the ASEs (average standard errors).

Assessment of the Antinociceptive Effect of the Extracts of *Aleurites moluccana* Using the Formalin Induced Pain Model.

This model is more specific than the acetic acid induced abdominal contortion model. It allows the assessment of two distinct types of pain: the pain of neurogenic origin (direct stimulation of the nociceptive neurons) and of inflammatory origin, representing the tonic response to pain, accompanied by an inflammatory response related to the release of chemical inflammation mediators. The nociceptive response was induced using 20 µL of formalin, that consists of a formaldehyde solution at 0.92% (2.5%, via intraplantar), injected in the dorsal region of the animal's rear right paw with the vehicle being injected in the dorsal region of the rear left paw. Immediately after the formalin injection, the animals were placed under a glass dome surrounded by mirrors in order to facilitate observation of the ensuing behaviour. Observation commenced immediately, initially timing the reaction to pain during the first 5 minutes after the formalin injection (corresponding to the period of neurogenic pain). Following an interval of 10 minutes, the licking times were recorded for a further 15 minutes (corresponding to the inflammatory pain). Total test time was of 30'.

At the end of this observation period, the animals were sacrificed by cervical displacement and the rear paws were removed at the tibiotarsal region and weighed on an analytical balance to quantify the edema induced by the formalin. The difference in weight (in mg) between the right paw (injected with formalin) and the left paw (injected with saline) was considered the rate of edema. (Dubuisson, D. et al., 1977, Pain., 4, 161-174; Hunskaar, S. and Hole, K., 1987, Pain, 28, 343-355). Each analysis was performed using 8 to 10 male animals (Swiss Webster mice) weighing between 25 and 30 g.

The dose was calculated individually for each animal with the quantity in mg/kg (mg/1.000 g) of the substance to be administrated being in accordance to its weight. The injected volume of the solutions followed the rule of 0.1 ml/10 g of the animal's weight.

The animals were observed after the intraplantar injection of formalin for a period of 30 minutes. The reaction time (time in which the animal remains licking the injected paw) is then quantified in each of the phases: phase I (neurogenic pain—5 min observation) and phase II (inflammatory pain—15 min observation).

Assessment of the Antinociceptive Effect of the Extracts of *Aleurites moluccana* Using the Hot Plate Model.

The hot plate model is normally used for verification of analgesic medicines having an action mechanism that may involve the opioid route. The animals are placed on a hot plate (UGO BASILE, model L1912-06), programmed to a temperature of 56° C. (±1) and the time (in seconds) that each animal takes to lick, bite or lift its paws is considered indicative of pain. The maximum permissible time for the animals to remain on the plate is 30 seconds in order to prevent tissue damage caused by the heat. In this model, the animals are pre-selected 24 hours before the test so as to ascertain their pain threshold without being submitted to any treatment. The animals with a pain threshold under 10 s (observed in the pre-test) were submitted to the test. A positive control for the test was also performed, with the animals being submitted to treatment with morphine (5 mg/kg) administered subcutaneously (Souza, M. M. et. al. Métodos de avaliação de atividade biológica de produtos naturais e sintéticos. In Cechinel Filho, V., Bresolin, T. M. B. Ciências Farmacêuticas: Contribuição ao desenvolvimento de novos fármacos e medicamentos, 2003, 108-166).

Each analysis was performed using 8 to 10 male animals (Swiss Webster mice) weighing between 25 and 30 g. The results were quantified according to the arithmetical average of the reaction time in seconds after being placed on the hot plate (the time span before the animals presented thermal sensitivity which was expressed by licking the rear paws and an attempt to escape the pain by rearing), followed by the ASEs (average standard errors).

Statistical Analysis:

Parametric statistical tests were performed on the models described above. The results were submitted to ANOVA variance analysis followed by appropriate post hoc tests. In the case of the pain and inflammation models, the results were presented as average±average standard error (ASEs), except for DI50 (the dose that reduces response by 50% in relation to the control group), which was presented as a geometric average accompanied by its respective reliability limit at 95% level. The statistical analyses of the results were performed by means of variance analysis followed by the multiple comparison test using the Dunnett method, when appropriate. Values of $p<0.05$ were considered to indicate significance. The DI50 was estimated by means of individual experiments using GraphPad Instat statistical software.

EXAMPLE VI

Tests for Determining the Anti-Inflammatory Activity of the Extract of *A. moluccana*

Assessment of the Anti-Inflammatory Effect of the Dry Extract of *Aleurites moluccana* Using the Phlogistic Agent Induced Edema of the Paw Model.

The edema of the paw pharmacological model is not considered as an inflammation model per se, but rather as a model of antiedematogenic activity since it merely assesses one of the parameters of the inflammatory process, namely, the formation of the edema. The phlogistic agent used in the experiment is generally carragenine. Several stages of the process may be assessed during the "inflammation" induced by this agent. The histamine, serotonin and substance P mediators are released between 0 and 2 hours after administration of the carragenine, prostaglandins, nitric oxide and several tachykinins are released at the peak of the maximum response to the inflammation (following the fourth hour of the experiment).

In this manner, it is possible to ascertain in which phase of the inflammatory process a compound acts, and, later, induce the edema with that specific mediator. Therefore, it is possible to characterise both the antiedematogenic effect and also the mechanism of action of the compound undergoing study, or, in other words, which mediators of the inflammatory process are supposedly inhibited by the compound.

Edema of the paw induced by carragenine—During the trials, the animals received intraplantar injections of the phlogistic agent, carragenine, at a concentration of 300 ug/paw diluted in saline solution in the right paw (0.025 ml/paw), and physiological solution in the left paw (0.025 ml/paw). The several concentrations of the dry extract and the negative control (physiological solution) were administered orally (0.3 ml/100 g of the animal's weight) 1 hour before the injection with carragenine. The positive control (dexamethazone 0.5 mg/kg) was administered subcutaneously 4 hours before. The edema of the paw was measured plethysmometrically (plethysmometer Ugobasile, Italy) at time intervals of 0.5, 1, 2, 3 and 4 hours after injection of the phlogistic agent. The variance in paw volume was expressed in ml and the difference between the volume of the right and left paws is considered as being the edema rate (Souza, M. M. et al. (2003)).

Edema of the paw induced by bradykinin—During the trials, the animals received intraplantar injections of the phlogistic agent, bradykinin, at a concentration of 300 ug/paw diluted in saline solution in the right paw (0.025 ml/paw), and physiological solution in the left paw (0.025 ml/paw). The several concentrations of the dry extract and the negative control (physiological solution) were administered orally (0.3 ml/100 g of the animal's weight) 1 hour before the injection with bradykinin. The positive control (dexamethazone 0.5 mg/kg) was administered subcutaneously 4 hours before. The edema of the paw was measured plethysmometrically (plethysmometer Ugobasile, Italy) at time intervals of 0.5, 1 and 2 hours after injection of the phlogistic agent. The variance in paw volume was expressed in ml and the difference between the volume of the right and left paws is considered as being the edema rate (Souza, M. M. et al. (2003)).

Edema of the paw induced by histamine—During the trials, the animals received intraplantar injections of the phlogistic agent, histamine, at a concentration of 0.1%/paw diluted in saline solution in the right paw (0.025 ml/paw), and physiological solution in the left paw (0.025 ml/paw). The several concentrations of the dry extract and the negative control (physiological solution) were administered orally (0.3 ml/100 g of the animal's weight) 1 hour before the injection with histamine. The positive control (dexamethazone 0.5 mg/kg) was administered subcutaneously 4 hours earlier. The edema of the paw was measured plethysmometrically (plethysmometer Ugobasile, Italy) at time intervals of 0.5, 1 and 2 hours after injection of the phlogistic agent. The variance in paw volume was expressed in ml and the difference between the volume of the right and left paws is considered as being the edema rate (Souza, M. M. et al. (2003)).

Each of the analyses described above required 8 to 10 male animals (Wistar Rats) weighing between 200 and 300 g.

The results were quantified through the arithmetical average obtained for the edemas of the paws from each treatment group, followed by the SEAs (standard errors of average), across the measurement times during each experiment: carragenine (6 measurements in 4 hours of experiment), bradykinin and histamine (3 measurements in 2 hours of experiments).

Assessment of the Anti-Inflammatory Effect of the Dry Extract of *Aleurites moluccana* through the Pleurisy Induced by the Intrapleural Injection of Phlogistic Agents Model Among the animal models available for assessing the anti-inflammatory activity of substances, the pleurisy model is considered to be one of the more complete because the drained fluids from the pleural cavity allow the analysis and quantification of the cellular and humoral components of the inflammation without resorting to meticulous extraction and quantification procedures. (Saleh T. S. F., Calixto, J. B. Medeiros, Y. S., 1997, Eur J. Pharmacol., 331, 43-52). Pleurisy may be induced in animals by phlogistic agents such as carragenine, bradykinin, Substance P, prostaglandin $E_2$ etc. and, as before in the edema of the paw model, the process is first induced using carragenin. The animals were treated with different concentrations (125, 250, 500 mg/kg) of the dry extract of *A. moluccana*, and the vehicle, (saline solution) administered orally. They then received an endovenous injection (0.2 ml) of Evans blue solution (25 mg/Kg). The phlogistic agent (carragenine 1.0%, Substance P (20 nmol), and bradykinin (10 nmol), histamine (100 µg/cavity) was administered intrapleurally one hour after injection of the above treatments. This provides a group treated with the extract and with the phlogistic agent, a negative control group (pre-treated with saline solution v.o. and receiving saline solution i.pL.) and another control group (pre-treated with saline solution v.o. and receiving the phlogistic agent i.pL.) Four hours after treatment with the phlogistic agent, the animals were sacrificed and their abdominal region was opened rupturing the diaphragm. The pleural cavity was rinsed with a heparinised (20 UI/ml) saline solution (1.0 ml). The drained pleural fluid was then collected with an aliquot (10 µL) of the latter being added to a Turk solution (2% acetic acid) at a proportion of 1:20. Part of this material (10 µL) was transferred to a Neubauer chamber for a total cell count. The remaining pleural wash was centrifuged (10.000 rpm×10 min). The supernatant was removed and used for an ELISA reading (620 nm) with the purpose of measuring the plasma outflow (edema) after the inflammatory stimulus. The pellet was resuspended with 100 µL egg albumin (3%) and 10 µL was added to a slide covered in perforated filter paper which was then left to dry before staining using the May-Grunwald-Giemsa method for differential cell count by microscopy (enlarged 100 times).

Assessment of the Anti-Inflammatory Effect of the Extracts of *Aleurites moluccana* Using the Croton Oil Induced Ear Edema Model The ear edema model is specific and broadly used to research the activity of anti-inflammatory agents of topical use. The irritant agent used is croton oil and the extent of the edema is measured by the difference in the thickness of the ear before and after treatment (Montello, M. S. A. G., Efeito da terapia com laser de baixa potência (HeNe e AsGa) na dermatite induzida por óleo de cróton na orelha de camundongo. São José dos Campos, 2002. 82p. Dissertação Mestrado em Engenharia Biomédica—Instituto de pesquisa e desenvolvimento—Universidade do Vale do Paraíba).

A "basal" measurement of the ear thickness of the animal was performed, immediately followed by application of the control substance or the extract to the right inner ear. After 30 minutes, croton oil was applied to the outer part of the same ear. The ear was then measured again 4 hours after treatment with croton oil.

Each analysis was performed using 8 to 10 male animals (Swiss Webster mice) weighing between 25 and 30 g. The results were quantified according to the arithmetical average obtained for the ear edemas for each treatment group over the measurement times during the experiment (2 measurements in 6 hous of experiment run time) followed by the ASEs (average standard errors).

Assessment of the Antipyretic Effect of the Extracts of *Aleurites moluccana* Using the LPS Induced Hyperthermia Model in Rats.

Antipyretic properties are also observed in NSAIDs and, the assessment of this pharmacological property is also important when assessing analgesic and anti-inflammatory substances. The onset of the febrile process involves mediators such as prostaglandins and interleukins, amongst others, whose activities are associated to the processes of analgesia and inflammation. Generally, the pharmaceuticals that interfere with the activities of these mediators exhibit all three pharmacologic properties. The LPS induced hyperthermia model was used to verify the antipyretic effect of the soft extract of *A. moluccana*. Groups of animals were treated the soft extract of the plant in two doses (5.0 and 10 mg/kg), with a positive control (sodium dipyrone, 10 mg/kg) and/or negative (vehicle) by intraperitoneal route. The basal temperatures of all groups were recorded after 60 minutes, following which the groups (treated and control) received an intraperitoneal injection of LPS (10 µg/Kg, diluted in physiological solution). The temperatures were verified by carefully inserting veterinary thermometers in the rectal canal of each animal and maintaining it there for approximately 1 minute. The temperatures were recorded 40 minutes after injecting the LPS and at intervals of 40 minutes thereon for a period of 7 hours and 20 consecutive minutes, or, in other words, at 40, 80, 120, 160, 200, 240, 280, 320, 400 and 1.440 minutes. Results were expressed as the difference between the final temperatures and the basal temperature as described by Roth and De Souza (Roth, J. De-Souza, G. E. P., 2001, Brazilian Journal of Medicinal and Biological Research 34, 301-314).

Male Wistar rats (250 to 300 g) were pre-treated with *A. moluccana* (5 to 10 mg/Kg), and/or vehicle and dipyrone (10 mg/Kg) and, after 1 hour, submitted to the LPS induced fever model (10 µg/Kg). The temperature variations were verified at intervals of 40 minutes, over a period of 8 hours. Possible alterations to the gastric mucosa of the animals caused by the plant were also assessed by means of the above treatment but with the additional of indomethacin (30 mg/Kg).

Statistical Analysis:

Statistical analysis of the data was performed by means of one-way ANOVA variance analysis followed by the Dunnett test. Values of $p<0.05$ were considered to indicate significance. The DI50 (the dose that reduces response by 50% in relation to the control group), which was presented as a geometric average accompanied by its respective reliability limit at 95% level and was estimated by means of individual experiments by the linear regression method using Graph-Pad® software. The DI50 calculation is used for potency comparison between the test-substance and traditional pharmaceuticals. The inhibition percentages were stated as the average±the average standard error of the difference (in percentage) for each individual experiment in relation to the corresponding control group.

EXAMPLE VII

Tests for Determining the Anti-Hypernociceptive Activity of the Extract of *A. moluccana* in Persistent Pain Models Assessment of the Effect of the Dry Extract of *Aleurites moluccana* on Mechanical Hypernociception Induced by the Intraplantar Injection of Carragenine.

The mice had inflammatory hyper-nociception induced by an intraplantar injection of 50 µl of carragenine (300 ug/site) on the plantar surface of the right rear foot. This dose is capable of producing an edema, hyper-nociception and significant swelling of the injected paw but, however, the animals continue to present normal behaviour. (De Campos et al., 1996, Eur J Pharmacol., 316, 2-3, 277-86; Bortolanza et al., 2002, Eur. J. Pharmacol., 453, 2-3, 203-8; Quintão et al., 2005, *Anesth Analg.*, 101, 6, 1763-9; Quintão et al., 2006, Neuropharmacol., 50, 5, 614-620). The animals were initially pre-treated with the dry extract of *A. moluccana*, administered orally, (125-500 mg/kg; v.o.), 1 h prior to inducing hypernociception. The animals then received an intraplantar injection of carragenine (300 µg/paw) and were assessed for mechanical hypernociception using the von Frey filament, as described below in item (e), at different times (1, 3, 4, 6, 24 and 48 h). The control group was treated with the vehicle (10 ml/kg) used for dilution of the extract (saline 0.9%).

Assessment of the Effect of the Dry Extract of *Aleurites moluccana* on Mechanical Hypernociception Induced by the Intraplantar Injection of Prostaglandin $E_2$ ($PGE_2$).

The animals were initially pre-treated with the dry extract of *A. moluccana*, administered orally, (125-500 mg/kg; v.o.), 1 h prior to inducing hypernociception. At the end of the treatment time, the animals received injections i.pl. of $PGE_2$ (0.1 nmol/paw) (Kassuya et al., 2007, Br J Pharmacol., 150 (6), 727-737) after which they were assessed for mechanical hypernociception using the von Frey filament 0.6 g, as described below in item (e), at different times (0.5, 1, 2, 4, 6 and 24 h). The control group was treated with the vehicle (10 ml/kg) used for dilution of the extract (saline 0.9%).

Assessment of the Preventive and Curative Effect of the Dry Extract of *Aleurites moluccana* on Mechanical Hypernociception Induced by the Intraplantar Injection of the Complete Freund Adjuvant (CFA).

In order to induce a persistent inflammatory response, the animals received an injection i.pl of 20 µl of complete Freund adjuvant (CFA; 1 mg/ml of mycobacterium tuberculosis bacillum inactivated by heat; with each mililitre (ml) of the vehicle containing 0.85 ml of paraffin oil+0.15 ml of manide monooleate) on the plantar surface of the rear right paw (Cao et al., 1998, Nature, 392, 390-394; Ferreira et al., 2001, Neuropharmacol., 41, 8, 1006-1012). Mechanical and thermal hypernociception were assessed using the von Frey filament 0.6 g, as described in below in item (e). In order to assess the preventive effect on mechanical hypernociception, the animals were initially pre-treated with the dry extract of *A. moluccana*, administered orally, (125-500 mg/kg) or the vehicle (1.0 ml/kg). After 1 h of treatment, the animals received an injection i.pl CFA, and mechanical hypernociception was assessed at different time intervals (1, 2, 4, 6, 8, 12, 24 and 48 h).

With the intent of verifying the curative treatment, the animals received an intraplantar injection of CFA and after 24 h were then treated orally with the dry extract of *A. moluccana* (125-500 mg/kg) or vehicle (10 ml/kg), twice a day (12 in 12 h) for 5 consecutive days with the mechanical hypernociception of the ipsilateral and contralateral paws to the injection of CFA being assessed 6 h after administration of the first daily dose, as described above. In order to investigate the extent of the antinociceptive effect of *A. moluccana* in the experiments using CFA, the treatment was interrupted 5 days after administration of the first dose and then renewed after 2 days to investigate any possible tolerance development.

Assessment of the Preventive and Curative Effect of the Dry Extract of *Aleurites moluccana* on Mechanical Hypernociception Induced by the Partial Constriction of the Sciatic Nerve (PCSN).

The procedure used was similar to the one described for rats by Seltzer et al. (1990) and modified for use with mice by Mamberg and Basbaum (1998). The mice were anaesthetised with chloral hydrate 7% (8 ml/kg; i.p.). Constriction of the sciatic nerve was acheived tying ⅓ to ½ of the dorsal part of the sciatic nerve with 8-0 stitching thread (Ethicon®). A group of animals had the sciatic nerve exposed without, however, any tying process (false operated group). On the fourth post-operatory day, the animals were assessed for mechanical hypernociception using the von Frey monofilament, as described below in item (e) and were then treated orally with the dry extract of *A. moluccana* (125-500 mg/kg) or vehicle (10 ml/kg), twice a day (12 in 12 h) for 5 consecutive days with the mechanical hypernociception being assessed 6 h after administration of the first daily dose.

Analysis of the Mechanical Threshold Using the von Frey Filament Technique.

To assess the mechanical hypernociception, the animals subjected to the carragenin, CFA or PCSN induced hypernociception models were placed singly in transparent acrylic individual compartments (9×7×11 cm) located on a raised wireframe platform to allow access to the plantar surface of the rear paws. The animals were acclimatised for at least 30 minutes before initiating the behavioural tests. The frequency of the withdrawal response was obtained using 10 applications (each lasting 1 s) of the von Frey filament 0.6 g (VFH, Stoelting, Chicago, USA). The stimuli were applied to the plantar surface of the animal's rear right paw (Quintão et al., 2005, *Anesth Analg.*, 101, 6, 1763-9; Quintão et al., 2006, Neuropharmacol., 50, 5, 614-620). In order to determine the basal mechanical threshold (B), all the groups of animals were submitted to prior assessment a then newly assessed at different times after the carragenine or CFA injections, or after the PCSN.

Statistical Analysis:

The statistical analysis of the data was performed by means of the variance analysis (two-way ANOVA) followed by the Bonferroni test. Values of p<0.05 were considered to indicate significance. The DI50s (the dose that reduces response by 50% in relation to the control group) were presented with geometric averages accompanied by their respective reliability limit at a 95% level and were estimated by means of individual experiments using the linear regression method of the Graphpad® software. The DI50 calculation is used for potency comparison between the test-substance and traditional pharmaceuticals. The inhibition percentages were stated as the average±the average standard error of the difference (in percentage) between the areas under the curves plotted for each individual experiment in relation to the corresponding control group.

EXAMPLE VIII

Assessment of Pharmacological Effect of the Dry Extract of A. moluccana Neuropathic Pain Test in Mice by The pharmacological assayes were performed with Swiss mice (n=8 to 10 animals), female, weighing between 25 to 30 g, maintained under controlled temperature and lighting, with feed and water "ad libitum", except during the experiment period. Each experiment used from 8 to 10 animals in each treatment group and after weighing, these were identified with sequential numbers using a marker-pen.

Partial Sciatic Nerve Constriction (PSNC) Inducement

The procedure used was similar to the one described for rats by Seltzer et al. (1990) and modified for use with mice by Mamberg and Basbaum (1998). The mice were anaesthetised with 7% chloral hydrate (8 ml/kg; i.p.). Constriction of the sciatic nerve was acheived tying ⅓ to ½ of the dorsal part of the sciatic nerve with 8-0 stitching thread (Ethicon®). A group of animals had the sciatic nerve exposed without, however, any tying process (false operated group). On the fourth post-operatory day, the animals were assessed for mechanical hypernociception using the von Frey monofilament, as described below in item (e) and were then treated orally with the dry extract of A. moluccana (125-500 mg/kg) or vehicle (10 ml/kg), twice a day (12 in 12 h) for 5 consecutive days with the mechanical hypernociception being assessed 6 h after administration of the first daily dose.

Analysis of the Mechanical Threshold Using the von Frey Filament Technique.

To assess the mechanical hypernociception, the animals subjected to PCSN induced hypernociception models were placed singly in transparent acrylic individual compartments (9×7×11 cm) located on a raised wireframe platform to allow access to the plantar surface of the rear paws. The animals were acclimatised for at least 30 minutes before initiating the behavioural tests. The frequency of the retrieval response was obtained using 10 applications (each lasting 1 s) of the von Frey filament 0.6 g (VFH, Stoelting, Chicago, USA). The stimuli were applied to the plantar surface of the animal's rear right paw (Quintão et al., 2005, *Anesth Analg.*, 101, 6, 1763-9; Quintão et al., 2006, Neuropharmacol., 50, 5, 614-620). In order to determine the basal mechanical threshold (B), all the groups of animals were submitted to prior assessment a then newly assessed at different times after the PCSN.

The statistical analysis of the data was performed by means of the variance analysis (two-way ANOVA) followed by the Bonferroni test. Values of p<0.05 were considered to indicate significance.

Effect of the Dry Extract of *Aleurites moluccana* on Mechanical Hypernociception Induced by the Partial Constriction of the Sciatic Nerve The oral treatment of the dry extract of *Aleurites moluccana* (industrial batch) when administered in doses of 125 to 500 mg/kg, was capable of significantly reducing the mechanical hypernociception induced by PSNC. This inhibition was significant for up to 8 days, when the treatment was interrupted, as seen in FIG. 24.

Figure 24:
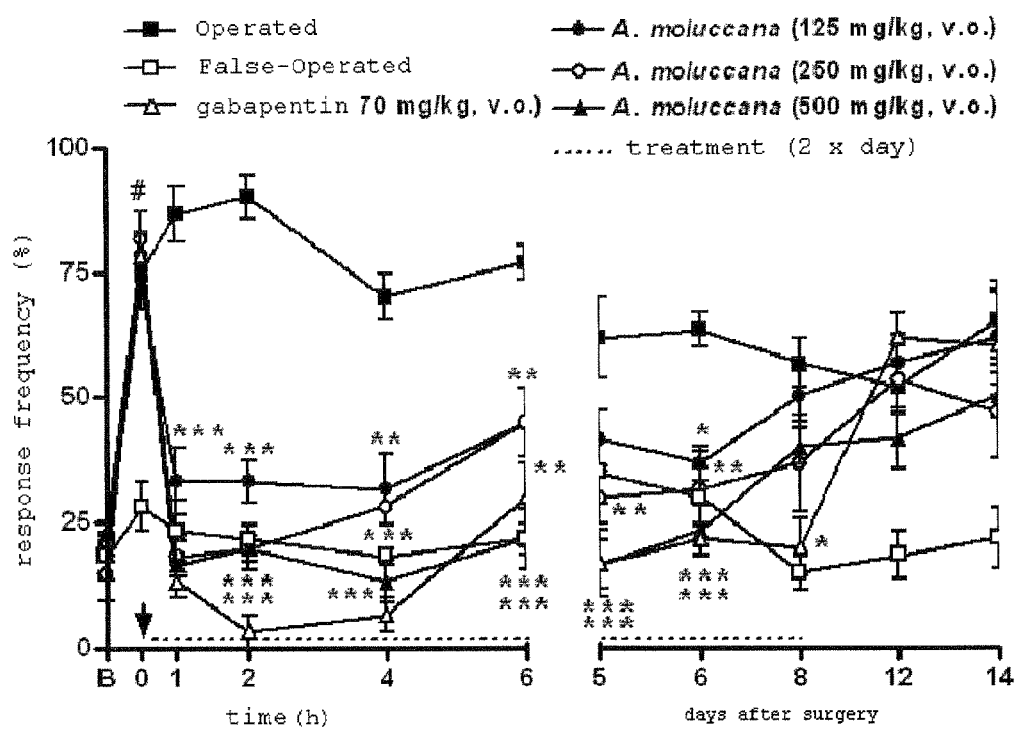
FIG. 24 shows the effect of treatment using the dry extract of *Aleurites moluccana* (125 to 500 mg/kg, administered orally) for mechanical hypernociception induced by PSNC.

FIG. 24 shows the effect of the treatment using the dry extract of *Aleurites moluccana* (125 to 500 mg/kg, administered orally) for mechanical hypernociception induced by PSNC. Each point represents the average of 6 to animals and the vertical bars indicate the ASEs. The results differ significantly in relation to the control group (C), *P<0.05, P<0.01 e *<0.001.

EXAMPLE IX

Acute Toxicity Trial of the Extract of *Aleurites moluccana*

This study refers to an estimate and preliminary assessment of the toxic properties of a test-substance, providing information relating to the risks to health resulting from an exposure of short duration by the chosen route of administration. The acute toxicity further serves as a basis for determining a dose regimen for the research relating to subchronic, chronic and repeated dose toxicity, as well as providing initial information concerning the toxic action mode of the test-substance.

The experiment used 10 male mice and 10 female mice, divided in 4 groups: a) male group treated with the vehicle (saline solution), b) male group treated with the soft extract of *A. moluccana* (5000 mg/Kg); c) female group treated with the vehicle, and d) female group treated with the extract (5000 mg/Kg). Food was withheld for 6 hours, following which the animals received a force-feeding treatment and were immediately transferred to individual boxes for observation using the hippocratic test as described by Brito (1994) (Brito, A. S. *Manual de Ensaios toxicológicos in vivo*. Campinas: UNICAMP, 199, 41-121). The animals were observed individually and systematically for 24 hours after treatment for intervals of (0 to 10 min, 30 min, 60 min, 180 min and 1.440 min). The supply of water and feed was restricted during the first 4 hours of observation. The behaviours and/or manifestations to be noted were: piloerection, salivation, cage corner movement, tremors, tachycardia, irritability, miction, defecation, ptosis, convulsions and the number of deaths. Special attention was given to symptoms such as: tremors, convulsions, salivation, diarrhoea, irritability, lethargy and coma. In the course of the experiment, any deaths and their times of occurrence are registered and, whenever possible, the causes are investigated. At the end of the experiment the animals were weighed and later sacrificed. The results were quantified on average in terms of the appearance of the behavioural response being observed at the specific time of observation. For example, if only 3 out of the 5 animals of the experiment were observed to defecate, the table will record ⅗. The largest dose used was of 5000 mg and as no deaths were verified, a DL50 (consisting of a value statistically derived from the administration of a single dose capable of causing the death of 50% of the animals of an experiment) couldn't be calculated.

The test-substance with a DL50 over 5 g has a great possibility of not exhibiting toxic effects.

The statistical analysis of the data was performed by means of the variance analysis followed by the T test. Values of $p<0.05$ were considered to indicate significance.

EXAMPLE X

An example of a pharmaceutical composition in the form of a coated pill may be obtained by the following formulation 1:

| Ingredients | Contribution % | Code |
|---|---|---|
| Nucleus: | | |
| Dry extract of *Aleurites* | 40% | A |
| Spray-dried lactose | 28% | B |
| Crospolyvinylpirrolidone | 10% | C |
| Microcrystalline cellulose | 8 | D |
| Ascorbic acid | 1% | E |
| Sodic croscarmelose | 2% | F |
| Magnesium stearate | 1.5% | G |
| Coating: | | |
| Eudragit ® | 7% | H |
| Propylenoglycol | 1% | I |
| Titanium Dioxide | 0.07% | J |
| Yellow iron oxide | 0.01% | K |
| Triethylcitrate | 0.20% | L |
| TOTAL | 100% | |

Preparation Method: The nucleus is prepared by first individually weighing and sieving the components. Following which, the components A, B, C and D are mixed in a "v" type mixer for 20 minutes. Components F and G are then added and mixed for a further 5 minutes. In sequence, the mixture is submitted to direct compression to form the compressed nuclei. The latter are then coated with a solution containing components H, I, J, K and L by atomisation (aspersion) to form a coating film.

EXAMPLE XI

An example of a pharmaceutical composition in the form of a capsule may be obtained by the following formulation 2:

| Ingredients | Contribution % | Code |
|---|---|---|
| Dried extract of *Aleurites* | 30% | A |
| Mannitol | 50% | B |
| Microcrystalline cellulose | 10% | C |
| Ascorbic acid | 1% | D |
| Pregelatinised starch | 8% | E |
| Talcum | 1% | F |
| TOTAL | 100% | |

Preparation Method: The capsules are prepared by first weighing, mixing and sieving the components A, B, C and D and in sequence, the mixture is submitted to a wet granulation process in adequate equipment by gradually adding a solution containing the agglutinat E. Following which, the granules are immediately submitted to drying in an oven at 30 a 40° C., until attaining a humidity rate of approximately 2%. In sequence, the dry granules are submitted to classification and mixed with lubricant F for 5 minutes. The classified dry granules are then encapsulated.

EXAMPLE XII

An example of a pharmaceutical composition in the form of a suspension may be obtained by the following formulation 3:

| Components | Contribution % | Code |
|---|---|---|
| Dry extract of *Aleurites* | 30% | A |
| Citric acid | 1.00% | B |
| Sodium citrate | 1.00% | C |
| Carboxymethylcellulose | 5.00% | D |
| Glycerine | 3.00% | E |
| Propylenoglycol | 5.00% | F |
| Sorbitol | 40.00% | G |
| Essence | 0.01% | H |
| Methylparaben | 0.10% | I |
| Propylparaben | 0.01% | J |
| Deionised water | QSP 100.0% | K |
| TOTAL | 100% | |

Preparation Method: The suspension is prepared by first weighing and mixing components A and F in a homogenising tank. In sequence, part of component K and the remaining components are gradually added to the mixture under constant agitation. The remainder of component K is then added to make up the intended volume. Finally, the mixture is submitted to mechanical agitation until complete homogenisation of the solution is attained.

EXAMPLE XIII

An example of a pharmaceutical composition in the form of a syrup may be obtained by the following formulation 4:

| Components | Contribution % | Code |
|---|---|---|
| Soft extract of *Aleurites* | 30% | A |
| Citric acid | 1.00% | B |
| Sodium citrate | 1.00% | C |
| Essence | 0.10% | D |
| Methylparaben | 0.10% | E |
| Propylparaben | 0.01% | F |
| Glycerine | 5.00% | G |
| Colorant | 0.01% | H |
| Sucrose | 50.00% | I |
| Deionised water | QSP 100.0 | J |
| TOTAL | 100% | |

Preparation Method: The suspension is prepared by first weighing and mixing components A and F in a homogenising tank. In sequence, part of component K and the remaining components are gradually added to the mixture under constant agitation. The remainder of component K is then added to make up the intended volume. Finally, the mixture is submitted to mechanical agitation until complete homogenisation of the solution is attained.

All publications mentioned in the above specification, and cited references therein are incorporated by reference. Several modifications and changes of process, extracts, compositions, methods and uses described in the present invention will be obvious to be practiced within the scope of this invention by those skilled in the art.

The invention claimed is:
1. A method of obtaining a standardized extract of leaves of *Aleurites moluccana*, wherein the standardized extract is standardized to 2″-O-rhamnosylswertisin and wherein the standardized extract is obtained by the following steps:
- (i) collecting, drying and subdividing leaves of *Aleurites moluccana*;
- (ii) pre-extracting the leaves of step (i) with ethanol to provide a first extract;
- (iii) extracting the first extract obtained in step (ii) with water and ethanol to provide a second extract;
- (iv) filtering the second extract obtained in step (iii) to provide a third extract;
- (v) concentrating the third extract obtained in step (iv) to provide a concentrated extract;
- (vi) pasteurizing the concentrated extract at a temperature of approximately 95 degrees C. for approximately 3 minutes to provide a pasteurized extract; and
- (vii) drying the pasteurized extract to provide a dried extract; wherein the dried extract is then qualitatively and quantitatively analyzed to determine the amount of 2″-O-rhamnosylswertisin by comparison with a marker, wherein the marker 2″-O-rhamnosylswertisin.

2. The method of claim 1, wherein the leaves are collected in dry weather.

3. The method of claim 1, wherein the pre-extracting step is performed by agitation at room temperature.

4. The method of claim 1, wherein the ratio of water:ethanol in step (iii) is 2:8.

5. The method of claim 1, wherein the ratio of water:ethanol in step (iii) is 3:7.

6. The method of claim 1, wherein the ratio of water and ethanol:leaves of *Aleurites moluccana* in step (iii) is between approximately 1:1 and 20:1.

7. The method of claim 1, wherein the ratio of water and ethanol:leaves of *Aleurites moluccana* in step (iii) is 10:1.

8. The method of claim 1, wherein the concentrated extract obtained in step (v) contains approximately 20% to 50% of solids.

9. The method of claim 8, wherein the drying step (vii) is performed by spray-drying, and wherein the spray-drying is performed in the presence of a drying adjuvant.

10. The method of claim 9, wherein the drying adjuvant is selected from the group consisting of colloidal silicon dioxide, modified cassava starch, tricalcium phosphate, maltodextrin, cyclodextrins, microcrystalline cellulose, lactose or a combination thereof, and wherein the drying adjuvant is added in a proportion of approximately 10 to 40% in relation to the ratio of total solids in the concentrated extract.

11. The method of claim 1, wherein the method optionally comprises a depigmentation step, step (viii), wherein the depigmentation is performed with active charcoal, adsorption resin or membrane ultrafiltration.

12. The method of claim 1, wherein the ratio of water:ethanol in step (iii) is 4:6.

13. The method of claim 1, wherein the ratio of water:ethanol in step (iii) 1:1.

* * * * *